United States Patent
Hoseini et al.

(10) Patent No.: US 11,529,371 B2
(45) Date of Patent: Dec. 20, 2022

(54) ANTI-CD33 ANTIBODY AGENTS

(71) Applicant: Memorial Sloan Kettering Cancer Center, New York, NY (US)

(72) Inventors: Sayed Shahabuddin Hoseini, New York, NY (US); Nai-Kong V. Cheung, New York, NY (US)

(73) Assignee: Memorial Sloan Kettering Cancer Center, New York, NY (US)

( * ) Notice: Subject to any disclaimer, the term of this patent is extended or adjusted under 35 U.S.C. 154(b) by 219 days.

(21) Appl. No.: 16/607,426

(22) PCT Filed: Apr. 24, 2018

(86) PCT No.: PCT/US2018/029191
§ 371 (c)(1),
(2) Date: Oct. 23, 2019

(87) PCT Pub. No.: WO2018/200562
PCT Pub. Date: Nov. 1, 2018

(65) Prior Publication Data
US 2020/0297764 A1  Sep. 24, 2020

Related U.S. Application Data

(60) Provisional application No. 62/489,269, filed on Apr. 24, 2017.

(51) Int. Cl.
| | |
|---|---|
| *C07K 16/28* | (2006.01) |
| *A61K 35/17* | (2015.01) |
| *A61P 35/02* | (2006.01) |
| *A61K 38/20* | (2006.01) |
| *C12N 15/63* | (2006.01) |
| *A61K 39/00* | (2006.01) |

(52) U.S. Cl.
CPC .......... *A61K 35/17* (2013.01); *A61K 38/2013* (2013.01); *A61P 35/02* (2018.01); *C07K 16/2809* (2013.01); *C12N 15/63* (2013.01); *A61K 2039/505* (2013.01)

(58) Field of Classification Search
None
See application file for complete search history.

(56) References Cited

U.S. PATENT DOCUMENTS

| | | | |
|---|---|---|---|
| 2008/0160018 A1* | 7/2008 | Queen | C07K 16/249 424/133.1 |
| 2008/0213256 A1 | 9/2008 | Kufer et al. | |
| 2009/0162931 A1 | 6/2009 | Bristol et al. | |
| 2013/0164295 A1 | 6/2013 | Gurney et al. | |
| 2013/0216528 A1 | 8/2013 | Cheung et al. | |
| 2015/0337048 A1 | 11/2015 | Stull et al. | |
| 2016/0347838 A1 | 12/2016 | Francis et al. | |

FOREIGN PATENT DOCUMENTS

| | | |
|---|---|---|
| WO | WO-2013/123061 A1 | 8/2013 |
| WO | WO-2015/150526 A2 | 10/2015 |
| WO | WO-2016/014942 A1 | 1/2016 |
| WO | WO-2016/086196 A2 | 6/2016 |
| WO | WO-2016/123143 A1 | 8/2016 |
| WO | WO-2016/150899 A2 | 9/2016 |
| WO | WO-2017/055318 A1 | 4/2017 |

OTHER PUBLICATIONS

Klinger et al. (Immunological Reviews 2016, vol. 270: 193-208). (Year: 2016).*
Xu et al. (Cancer Immunol Res; 3(3); 266-77, and Supplemental pp. 1-6. (2014)). (Year: 2014).*
Cho et al. (Nature. Feb. 13, 2003;421(6924):756-60, Supplemental p. 1-6). (Year: 2003).*
Perez-Oliva et al. (Glycobiology vol. 21 No. 6 pp. 757-770, 2011). (Year: 2011).*
Co et al. (J Immunol 1992; 148:1149-1154). (Year: 1992).*
Vajdos et al. (J Mol Biol. Jul. 5, 2002;320(2):415-28). (Year: 2002).*
Bedouelle et al. (FEBS J. Jan. 2006;273(1):34-46). (Year: 2006).*
Brown et al. (J Immunol. May 1, 1996;156(9):3285-91). (Year: 1996).*
Colman (Research in Immunology, 145:33-36, 1994). (Year: 1994).*
Rudikoff et al. (Proc. Natl. Acad. Sci. USA, 79: 1979-1983, Mar. 1982). (Year: 1982).*
Cheng, M., et. al., Structural design of disialoganglioside GD2 and CD3-bispecific antibodies to redirect T cells for tumor therapy, International Journal of Cancer, 136(2):476-486, (2015).
Hoseini, S.S., et. al., A potent tetravalent T-cell-engaging bi-specific antibody against CD33 in acute myeloid leukemia, Blood Advances, 2(11):1250-1258, (2018).
Arndt, C. et al., Costimulation improves the killing capability of T cells redirected to tumor cells expressing low levels of CD33: description of a novel modular targeting system, Leukemia, 28(1): 59-69 (2014).
International Search Report for PCT/US18/29191 (ANTI-CD33 Antibody Agents, filed Apr. 24, 2018), issued by ISA/US, 8 pages (dated Sep. 27, 2018).
Written Opinion for PCT/US18/29191 (ANTI-CD33 Antibody Agents, filed Apr. 24, 2018), issued by ISA/US, 19 pages (dated Sep. 27, 2018).

(Continued)

*Primary Examiner* — Zachary S Skelding

(74) *Attorney, Agent, or Firm* — Choate, Hall & Stewart LLP; Brenda Herschbach Jarrell; Tracy L. Vrablik

(57) ABSTRACT

Provided are anti-CD33 antibody agents, including anti-CD33 antibody agents in an IgG-scFv format. Various methods and reagents related thereto are also provided, including for example for the detection, prevention, and/or therapeutic treatment of CD33-related diseases, in particular, leukemias such as AML.

19 Claims, 18 Drawing Sheets
Specification includes a Sequence Listing.

(56) References Cited

OTHER PUBLICATIONS

Aigner, M. et al., T lymphocytes can be effectively recruited for ex vivo and in vivo lysis of AML blasts by a novel CD33/CD3-bispecific BiTE antibody construct, Leukemia, 27(5):1107-1115, (2013).

Klinger, M. et al., Harnessing T cells to fight cancer with BiTE® antibody constructs—past developments and future directions, Immunol. Rev., 270(1):193-208, (2016).

Reusch, U. et al., Characterization of CD33/CD3 Tetravalent Bispecific Tandem Diabodies (TandAbs) for the Treatment of Acute Myeloid Leukemia, Clin. Cancer Res., 22(23):5829-5838 (2016).

* cited by examiner

Modular IgG-scFv

SEQUENCE LISTING

```
<160> NUMBER OF SEQ ID NOS: 29

<210> SEQ ID NO 1
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 1

Glu Val Gln Leu Gln Gln Ser Gly Pro Glu Val Val Lys Pro Gly Ala
1               5                   10                  15

Ser Val Lys Ile Ser Cys Lys Ala Ser Gly Tyr Thr Phe Thr Asp Tyr
            20                  25                  30

Asn Met His Trp Val Lys Gln Ala His Gly Gln Ser Leu Glu Trp Ile
        35                  40                  45

Gly Tyr Ile Tyr Pro Tyr Asn Gly Gly Thr Gly Tyr Asn Gln Lys Phe
    50                  55                  60

Lys Ser Lys Ala Thr Leu Thr Val Asp Asn Ser Ala Ser Thr Ala Tyr
65                  70                  75                  80

Met Glu Val Arg Ser Leu Thr Ser Glu Asp Thr Ala Val Tyr Tyr Cys
                85                  90                  95

Ala Arg Gly Arg Pro Ala Met Asp Tyr Trp Gly Gln Gly Thr Leu Val
            100                 105                 110

Thr Val Ser Ser
        115

<210> SEQ ID NO 2
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2

Glu Val Gln Leu Val Gln Ser Gly Pro Glu Val Val Lys Pro Gly Ala
1               5                   10                  15

Ser Val Lys Ile Ser Cys Lys Ala Ser Gly Tyr Thr Phe Thr Asp Tyr
            20                  25                  30

Asn Met His Trp Val Arg Gln Ala His Gly Gln Ser Leu Glu Trp Ile
        35                  40                  45
```

-continued

```
Gly Tyr Ile Tyr Pro Tyr Asn Gly Gly Thr Gly Tyr Asn Gln Lys Phe
            50                  55                  60

Lys Ser Arg Ala Thr Leu Thr Val Asp Asn Ser Ala Ser Thr Ala Tyr
 65                  70                  75                  80

Met Glu Val Ser Ser Leu Arg Ser Glu Asp Thr Ala Val Tyr Tyr Cys
                 85                  90                  95

Ala Arg Gly Arg Pro Ala Met Asp Tyr Trp Gly Gln Gly Thr Leu Val
            100                 105                 110

Thr Val Ser Ser
        115

<210> SEQ ID NO 3
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 3

Glu Ile Val Leu Thr Gln Ser Pro Ala Thr Leu Ser Val Ser Leu Gly
 1               5                  10                  15

Gln Arg Ala Thr Ile Ser Cys Arg Ala Ser Glu Ser Val Asp Asn Tyr
            20                  25                  30

Gly Ile Ser Phe Met Asn Trp Phe Gln Gln Lys Pro Gly Gln Pro Pro
        35                  40                  45

Lys Leu Leu Ile Tyr Ala Ala Ser Asn Gln Gly Ser Gly Val Pro Ala
 50                  55                  60

Arg Phe Ser Gly Ser Gly Ser Gly Thr Asp Phe Thr Leu Thr Ile His
 65                  70                  75                  80

Pro Met Glu Glu Asp Asp Thr Ala Met Tyr Phe Cys Gln Gln Ser Lys
                 85                  90                  95

Glu Val Pro Trp Thr Phe Gly Gly Gly Thr Lys Leu Glu Ile Lys
            100                 105                 110

<210> SEQ ID NO 4
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 4

Glu Ile Val Leu Thr Gln Ser Pro Ala Thr Leu Ser Val Ser Leu Gly
 1               5                  10                  15

Glu Arg Ala Thr Ile Ser Cys Arg Ala Ser Glu Ser Val Asp Asn Tyr
            20                  25                  30

Gly Ile Ser Phe Met Asn Trp Phe Gln Gln Lys Pro Gly Gln Pro Pro
        35                  40                  45

Arg Leu Leu Ile Tyr Ala Ala Ser Asn Gln Gly Ser Gly Val Pro Ala
 50                  55                  60

Arg Phe Ser Gly Ser Gly Pro Gly Thr Asp Phe Thr Leu Thr Ile Ser
 65                  70                  75                  80

Ser Met Glu Pro Glu Asp Phe Ala Met Tyr Phe Cys Gln Gln Ser Lys
                 85                  90                  95

Glu Val Pro Trp Thr Phe Gly Gly Gly Thr Lys Leu Glu Ile Lys
            100                 105                 110
```

<210> SEQ ID NO 5
<211> LENGTH: 1389
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 5

```
atgggctggt cctgcatcat cctgtttctg gtggctaccg ccaccggcga ggtgcagctg      60
cagcagtctg gacccgaggt cgtgaagcct ggcgcctccg tgaagatctc ctgcaaggcc     120
tccggctaca ccttcaccga ctacaacatg cactgggtca agcaggccca cggccagtcc     180
ctggaatgga tcggctacat ctaccccctac aacggcggca ccggctacaa ccagaagttc     240
aagtccaagg ccaccctgac cgtggacaac tccgcctcca ccgcctacat ggaagtgcgg     300
tccctgacct ctgaggacac cgccgtgtac tactgcgcca gaggcagacc cgccatggac     360
tattggggcc agggcaccct cgtgaccgtg tcctctgctt ctaccaaggg cccatcggtc     420
ttccccctgg cacctcctc caagagcacc tctggggca gcggccct gggctgcctg        480 gtcaaggact acttccccga accggtgacg gtgtcgtgga actcaggcgc cctgaccagc     540
ggcgtgcaca ccttcccggc cgtcctacag tcctcaggac tctactccct cagcagcgtg     600
gtgaccgtgc cctccagcag cttgggcacc cagacctaca tctgcaacgt gaatcacaag     660
cccagcaaca ccaaggtgga caagagagtt gagcccaaat cttgtgacaa aactcacaca     720
tgcccaccgt gcccagcacc tgaactcctg ggggaccgt cagtcttcct cttccccca      780 aaacccaagg acaccctcat gatctcccgg acccctgagg tcacatgcgt ggtggtggac     840
gtgagccacg aagaccctga ggtcaagttc aactggtacg tggacggcgt ggaggtgcat     900
aatgccaaga caaagccgcg ggaggagcag tacaacagca cgtaccgtgt ggtcagcgtc     960
ctcaccgtcc tgcaccagga ctggctgaat ggcaaggagt acaagtgcaa ggtctccaac    1020
aaagccctcc cagcccccat cgagaaaacc atctccaaag ccaaagggca gccccgagaa    1080
ccacaggtgt acaccctgcc cccatcccgg gatgagctga ccaagaacca ggtcagcctg    1140
acctgcctgg tcaaaggctt ctatcccagc gacatcgccg tggagtggga gagcaatggg    1200
cagccggaga acaactacaa gaccacgcct cccgtgctgg actccgacgg ctccttcttc    1260
ctctacagca agctcaccgt ggacaagagc aggtggcagc aggggaacgt cttctcatgc    1320
tccgtgatgc atgaggctct gcacaaccac tacacgcaga agagcctctc cctgtctccg    1380
ggtaaatga                                                            1389
```

<210> SEQ ID NO 6
<211> LENGTH: 1389
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 6

```
atgggctggt cctgcatcat cctgtttctg gtggctaccg ccaccggcga ggtgcagctg      60
gtgcagtctg gacccgaggt cgtgaagcct ggcgcctccg tgaagatctc ctgcaaggcc     120
tccggctaca ccttcaccga ctacaacatg cactgggtgc acaggccca cggccagtcc     180 ctggaatgga tcggctacat ctaccccctac aacggcggca ccggctacaa ccagaagttc     240
```

```
aagtctcggg ccaccctgac cgtggacaac tctgcctcta ccgcctacat ggaagtgtcc      300
tccctgagat ccgaggacac cgccgtgtac tactgcgcca gaggcagacc cgccatggac      360
tattggggcc agggcaccct cgtgaccgtg tctagcgctt ctaccaaggg cccatcggtc      420
ttccccctgg cacctcctc caagagcacc tctgggggca cagcggccct gggctgcctg       480
gtcaaggact acttccccga accggtgacg gtgtcgtgga actcaggcgc cctgaccagc      540
ggcgtgcaca ccttcccggc cgtcctacag tcctcaggac tctactccct cagcagcgtg      600
gtgaccgtgc cctccagcag cttgggcacc cagacctaca tctgcaacgt gaatcacaag      660
cccagcaaca ccaaggtgga caagagagtt gagcccaaat cttgtgacaa aactcacaca      720
tgcccaccgt gcccagcacc tgaactcctg ggggaccgt cagtcttcct cttccccca        780 aaacccaagg acaccctcat gatctcccgg acccctgagg tcacatgcgt ggtggtggac      840
gtgagccacg aagaccctga ggtcaagttc aactggtacg tggacggcgt ggaggtgcat      900
aatgccaaga caaagccgcg ggaggagcag tacaacagca cgtaccgtgt ggtcagcgtc      960
ctcaccgtcc tgcaccagga ctggctgaat ggcaaggagt acaagtgcaa ggtctccaac     1020
aaagccctcc cagcccccat cgagaaaacc atctccaaag ccaaagggca gccccgagaa     1080
ccacaggtgt acaccctgcc cccatcccgg gatgagctga ccaagaacca ggtcagcctg     1140
acctgcctgg tcaaaggctt ctatcccagc gacatcgccg tggagtggga gagcaatggg     1200
cagccggaga caactacaa gaccacgcct cccgtgctgg actccgacgg ctccttcttc      1260
ctctacagca agctcaccgt ggacaagagc aggtggcagc aggggaacgt cttctcatgc     1320
tccgtgatgc atgaggctct gcacaaccac tacacgcaga gagcctctc cctgtctccg      1380 ggtaaatga                                                              1389
```

<210> SEQ ID NO 7
<211> LENGTH: 705
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 7

```
atgggctggt cctgcatcat cctgtttctg gtggctaccg ccaccggcga gatcgtgctg       60
actcagtctc ctgccaccct gtccgtgtcc ctgggccaga gagccaccat ctcttgcaga      120
gcctccgagt ccgtggacaa ctacggcatc tccttcatga actggttcca gcagaagccc      180
ggccagcccc ccaagctgct gatctacgcc gcttccaatc agggctctgg cgtgcccgct      240
agattctccg gctctggctc tggcaccgac ttcaccctga ccatccaccc catggaagag      300
gacgacaccg ccatgtactt tgccagcag tccaaagagg tgccctggac ctttggcgga      360
ggcaccaagc tggaaatcaa gcggaccgtg gccgctccct ccgtgttcat cttcccacct      420
tccgacgagc agctgaagtc cggcaccgct tctgtcgtgt gcctgctgaa caacttctac      480
ccccgcgagg ccaaggtgca gtggaaggtg gacaacgccc tgcagtccgg caactcccag      540
gaatccgtga ccgagcagga ctccaaggac agcacctact ccctgtcctc taccctgacc      600
ctgtccaagg ccgactacga aagcacaag gtgtacgcct gcgaagtgac ccaccagggc       660
ctgtctagcc ccgtgaccaa gtctttcaac cggggcgagt gctag                      705
```

<210> SEQ ID NO 8
<211> LENGTH: 705
<212> TYPE: DNA

<213> ORGANISM: Artificial Sequence
<220> FEATURE:
<223> OTHER INFORMATION: Description of Artificial Sequence: Synthetic polynucleotide

<400> SEQUENCE: 8

```
atgggctggt cctgcatcat cctgtttctg gtggctaccg ccaccggcga gatcgtgctg    60
actcagtctc ctgccaccct gtccgtgtcc ctgggcgaga gagccaccat ctcttgcaga   120
gcctccgagt ccgtggacaa ctacggcatc tccttcatga actggttcca gcagaagccc   180
ggccagcctc ctcggctgct gatctacgcc gcttccaatc agggctctgg cgtgcccgct   240
agattctccg gatctggccc tggcaccgac tttaccctga ccatctcctc catggaaccc   300
gaggacttcg ccatgtactt ttgccagcag tccaaagagg tgccctggac ctttggcgga   360
ggcaccaagc tggaaatcaa gcggaccgtg gccgctccct ccgtgttcat cttcccacct   420
tccgacgagc agctgaagtc cggcaccgct tctgtcgtgt gcctgctgaa caacttctac   480
ccccgcgagg ccaaggtgca gtggaaggtg gacaacgccc tgcagtccgg caactcccag   540
gaatccgtga ccgagcagga ctccaaggac agcacctact ccctgtcctc caccctgacc   600
ctgagcaagg ccgactacga aaagcacaag gtgtacgcct gcgaagtgac ccaccagggc   660
ctgtctagcc ccgtgaccaa gtctttcaac cggggcgagt gctag              705
```

<210> SEQ ID NO 9
<211> LENGTH: 446
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 9

```
Glu Val Gln Leu Val Gln Ser Gly Pro Glu Val Val Lys Pro Gly Ala
1               5                   10                  15

Ser Val Lys Ile Ser Cys Lys Ala Ser Gly Tyr Thr Phe Thr Asp Tyr
            20                  25                  30

Asn Met His Trp Val Arg Gln Ala His Gly Gln Ser Leu Glu Trp Ile
        35                  40                  45

Gly Tyr Ile Tyr Pro Tyr Asn Gly Gly Thr Gly Tyr Asn Gln Lys Phe
    50                  55                  60

Lys Ser Arg Ala Thr Leu Thr Val Asp Asn Ser Ala Ser Thr Ala Tyr
65                  70                  75                  80

Met Glu Val Ser Ser Leu Arg Ser Glu Asp Thr Ala Val Tyr Tyr Cys
                85                  90                  95

Ala Arg Gly Arg Pro Ala Met Asp Tyr Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
```

```
            195                 200                 205
Lys Val Asp Lys Arg Val Glu Pro Lys Ser Cys Asp Lys Thr His Thr
210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Arg Asp Glu Leu Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly Lys
        435                 440                 445

<210> SEQ ID NO 10
<211> LENGTH: 218
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 10

Glu Ile Val Leu Thr Gln Ser Pro Ala Thr Leu Ser Val Ser Leu Gly
1               5                   10                  15

Glu Arg Ala Thr Ile Ser Cys Arg Ala Ser Glu Ser Val Asp Asn Tyr
            20                  25                  30

Gly Ile Ser Phe Met Asn Trp Phe Gln Gln Lys Pro Gly Gln Pro Pro
        35                  40                  45

Arg Leu Leu Ile Tyr Ala Ala Ser Asn Gln Gly Ser Gly Val Pro Ala
    50                  55                  60

Arg Phe Ser Gly Ser Gly Pro Gly Thr Asp Phe Thr Leu Thr Ile Ser
65                  70                  75                  80

Ser Met Glu Pro Glu Asp Phe Ala Met Tyr Phe Cys Gln Gln Ser Lys
                85                  90                  95

Glu Val Pro Trp Thr Phe Gly Gly Gly Thr Lys Leu Glu Ile Lys Arg
            100                 105                 110
```

```
Thr Val Ala Ala Pro Ser Val Phe Ile Phe Pro Pro Ser Asp Glu Gln
            115                 120                 125

Leu Lys Ser Gly Thr Ala Ser Val Val Cys Leu Leu Asn Asn Phe Tyr
        130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215

<210> SEQ ID NO 11
<211> LENGTH: 256
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 11

Gln Val Gln Leu Val Gln Ser Gly Gly Gly Val Val Gln Pro Gly Arg
1               5                   10                  15

Ser Leu Arg Leu Ser Cys Lys Ala Ser Gly Tyr Thr Phe Thr Arg Tyr
            20                  25                  30

Thr Met His Trp Val Arg Gln Ala Pro Gly Lys Gly Leu Glu Trp Ile
        35                  40                  45

Gly Tyr Ile Asn Pro Ser Arg Gly Tyr Thr Asn Tyr Asn Gln Lys Phe
    50                  55                  60

Lys Asp Arg Phe Thr Ile Ser Arg Asp Asn Ser Lys Asn Thr Ala Phe
65                  70                  75                  80

Leu Gln Met Asp Ser Leu Arg Pro Glu Asp Thr Gly Val Tyr Phe Cys
                85                  90                  95

Ala Arg Tyr Tyr Asp Asp His Tyr Ser Leu Asp Tyr Trp Gly Gln Gly
            100                 105                 110

Thr Pro Val Thr Val Ser Ser Gly Gly Gly Gly Ser Gly Gly Gly Gly
        115                 120                 125

Ser Gly Gly Gly Gly Ser Gly Gly Gly Gly Ser Gly Gly Gly Gly Ser
    130                 135                 140

Gly Gly Gly Gly Ser Asp Ile Gln Met Thr Gln Ser Pro Ser Ser Leu
145                 150                 155                 160

Ser Ala Ser Val Gly Asp Arg Val Thr Ile Thr Cys Ser Ala Ser Ser
                165                 170                 175

Ser Val Ser Tyr Met Asn Trp Tyr Gln Gln Thr Pro Gly Lys Ala Pro
            180                 185                 190

Lys Arg Trp Ile Tyr Asp Thr Ser Lys Leu Ala Ser Gly Val Pro Ser
        195                 200                 205

Arg Phe Ser Gly Ser Gly Ser Gly Thr Asp Tyr Thr Phe Thr Ile Ser
    210                 215                 220

Ser Leu Gln Pro Glu Asp Ile Ala Thr Tyr Tyr Cys Gln Gln Trp Ser
225                 230                 235                 240

Ser Asn Pro Phe Thr Phe Gly Gln Gly Thr Lys Leu Gln Ile Thr Arg
                245                 250                 255
```

<210> SEQ ID NO 12
<211> LENGTH: 231
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 12

Gln Val Gln Leu Val Gln Ser Gly Gly Gly Val Val Gln Pro Gly Arg
1               5                   10                  15

Ser Leu Arg Leu Ser Cys Lys Ala Ser Gly Tyr Thr Phe Thr Arg Tyr
            20                  25                  30

Thr Met His Trp Val Arg Gln Ala Pro Gly Lys Cys Leu Glu Trp Ile
        35                  40                  45

Gly Tyr Ile Asn Pro Ser Arg Gly Tyr Thr Asn Tyr Asn Gln Lys Phe
    50                  55                  60

Lys Asp Arg Phe Thr Ile Ser Arg Asp Asn Ser Lys Asn Thr Ala Phe
65                  70                  75                  80

Leu Gln Met Asp Ser Leu Arg Pro Glu Asp Thr Gly Val Tyr Phe Cys
                85                  90                  95

Ala Arg Tyr Tyr Asp Asp His Tyr Ser Leu Asp Tyr Trp Gly Gln Gly
            100                 105                 110

Thr Pro Val Thr Val Ser Ser Gly Gly Gly Ser Asp Ile Gln Met
        115                 120                 125

Thr Gln Ser Pro Ser Ser Leu Ser Ala Ser Val Gly Asp Arg Val Thr
130                 135                 140

Ile Thr Cys Ser Ala Ser Ser Val Ser Tyr Met Asn Trp Tyr Gln
145                 150                 155                 160

Gln Thr Pro Gly Lys Ala Pro Lys Arg Trp Ile Tyr Asp Thr Ser Lys
                165                 170                 175

Leu Ala Ser Gly Val Pro Ser Arg Phe Ser Gly Ser Gly Ser Gly Thr
            180                 185                 190

Asp Tyr Thr Phe Thr Ile Ser Ser Leu Gln Pro Glu Asp Ile Ala Thr
        195                 200                 205

Tyr Tyr Cys Gln Gln Trp Ser Ser Asn Pro Phe Thr Phe Gly Cys Gly
    210                 215                 220

Thr Lys Leu Gln Ile Thr Arg
225                 230

<210> SEQ ID NO 13
<211> LENGTH: 236
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 13

Gln Val Gln Leu Val Gln Ser Gly Gly Gly Val Val Gln Pro Gly Arg
1               5                   10                  15

Ser Leu Arg Leu Ser Cys Lys Ala Ser Gly Tyr Thr Phe Thr Arg Tyr
            20                  25                  30

Thr Met His Trp Val Arg Gln Ala Pro Gly Lys Cys Leu Glu Trp Ile
        35                  40                  45

Gly Tyr Ile Asn Pro Ser Arg Gly Tyr Thr Asn Tyr Asn Gln Lys Phe
    50                  55                  60

```
Lys Asp Arg Phe Thr Ile Ser Arg Asp Asn Ser Lys Asn Thr Ala Phe
 65                  70                  75                  80

Leu Gln Met Asp Ser Leu Arg Pro Glu Asp Thr Gly Val Tyr Phe Cys
                 85                  90                  95

Ala Arg Tyr Tyr Asp Asp His Tyr Ser Leu Asp Tyr Trp Gly Gln Gly
             100                 105                 110

Thr Pro Val Thr Val Ser Ser Gly Gly Gly Ser Gly Gly Gly Gly
             115                 120                 125

Ser Asp Ile Gln Met Thr Gln Ser Pro Ser Ser Leu Ser Ala Ser Val
130                 135                 140

Gly Asp Arg Val Thr Ile Thr Cys Ser Ala Ser Ser Val Ser Tyr
145                 150                 155                 160

Met Asn Trp Tyr Gln Gln Thr Pro Gly Lys Ala Pro Lys Arg Trp Ile
                 165                 170                 175

Tyr Asp Thr Ser Lys Leu Ala Ser Gly Val Pro Ser Arg Phe Ser Gly
             180                 185                 190

Ser Gly Ser Gly Thr Asp Tyr Thr Phe Thr Ile Ser Ser Leu Gln Pro
             195                 200                 205

Glu Asp Ile Ala Thr Tyr Tyr Cys Gln Gln Trp Ser Ser Asn Pro Phe
210                 215                 220

Thr Phe Gly Cys Gly Thr Lys Leu Gln Ile Thr Arg
225                 230                 235

<210> SEQ ID NO 14
<211> LENGTH: 241
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 14

Gln Val Gln Leu Val Gln Ser Gly Gly Gly Val Val Gln Pro Gly Arg
1               5                   10                  15

Ser Leu Arg Leu Ser Cys Lys Ala Ser Gly Tyr Thr Phe Thr Arg Tyr
             20                  25                  30

Thr Met His Trp Val Arg Gln Ala Pro Gly Lys Cys Leu Glu Trp Ile
         35                  40                  45

Gly Tyr Ile Asn Pro Ser Arg Gly Tyr Thr Asn Tyr Asn Gln Lys Phe
     50                  55                  60

Lys Asp Arg Phe Thr Ile Ser Arg Asp Asn Ser Lys Asn Thr Ala Phe
65                  70                  75                  80

Leu Gln Met Asp Ser Leu Arg Pro Glu Asp Thr Gly Val Tyr Phe Cys
                 85                  90                  95

Ala Arg Tyr Tyr Asp Asp His Tyr Ser Leu Asp Tyr Trp Gly Gln Gly
             100                 105                 110

Thr Pro Val Thr Val Ser Ser Gly Gly Gly Gly Ser Gly Gly Gly Gly
             115                 120                 125

Ser Gly Gly Gly Gly Ser Asp Ile Gln Met Thr Gln Ser Pro Ser Ser
130                 135                 140

Leu Ser Ala Ser Val Gly Asp Arg Val Thr Ile Thr Cys Ser Ala Ser
145                 150                 155                 160

Ser Ser Val Ser Tyr Met Asn Trp Tyr Gln Gln Thr Pro Gly Lys Ala
                 165                 170                 175

Pro Lys Arg Trp Ile Tyr Asp Thr Ser Lys Leu Ala Ser Gly Val Pro
```

```
                180                 185                 190

Ser Arg Phe Ser Gly Ser Gly Ser Gly Thr Asp Tyr Thr Phe Thr Ile
        195                 200                 205

Ser Ser Leu Gln Pro Glu Asp Ile Ala Thr Tyr Tyr Cys Gln Gln Trp
        210                 215                 220

Ser Ser Asn Pro Phe Thr Phe Gly Cys Gly Thr Lys Leu Gln Ile Thr
225                 230                 235                 240

Arg

<210> SEQ ID NO 15
<211> LENGTH: 246
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 15

Gln Val Gln Leu Val Gln Ser Gly Gly Val Val Gln Pro Gly Arg
1               5                   10                  15

Ser Leu Arg Leu Ser Cys Lys Ala Ser Gly Tyr Thr Phe Thr Arg Tyr
            20                  25                  30

Thr Met His Trp Val Arg Gln Ala Pro Gly Lys Cys Leu Glu Trp Ile
        35                  40                  45

Gly Tyr Ile Asn Pro Ser Arg Gly Tyr Thr Asn Tyr Asn Gln Lys Phe
    50                  55                  60

Lys Asp Arg Phe Thr Ile Ser Arg Asp Asn Ser Lys Asn Thr Ala Phe
65                  70                  75                  80

Leu Gln Met Asp Ser Leu Arg Pro Glu Asp Thr Gly Val Tyr Phe Cys
                85                  90                  95

Ala Arg Tyr Tyr Asp Asp His Tyr Ser Leu Asp Tyr Trp Gly Gln Gly
            100                 105                 110

Thr Pro Val Thr Val Ser Ser Gly Gly Gly Ser Gly Gly Gly Gly
        115                 120                 125

Ser Gly Gly Gly Gly Ser Gly Gly Gly Gly Ser Asp Ile Gln Met Thr
    130                 135                 140

Gln Ser Pro Ser Ser Leu Ser Ala Ser Val Gly Asp Arg Val Thr Ile
145                 150                 155                 160

Thr Cys Ser Ala Ser Ser Ser Val Ser Tyr Met Asn Trp Tyr Gln Gln
                165                 170                 175

Thr Pro Gly Lys Ala Pro Lys Arg Trp Ile Tyr Asp Thr Ser Lys Leu
            180                 185                 190

Ala Ser Gly Val Pro Ser Arg Phe Ser Gly Ser Gly Ser Gly Thr Asp
        195                 200                 205

Tyr Thr Phe Thr Ile Ser Ser Leu Gln Pro Glu Asp Ile Ala Thr Tyr
    210                 215                 220

Tyr Cys Gln Gln Trp Ser Ser Asn Pro Phe Thr Phe Gly Cys Gly Thr
225                 230                 235                 240

Lys Leu Gln Ile Thr Arg
                245

<210> SEQ ID NO 16
<211> LENGTH: 251
<212> TYPE: PRT
<213> ORGANISM: Artificial Sequence
<220> FEATURE:
<223> OTHER INFORMATION: Description of Artificial Sequence: Synthetic
``` polypeptide

<400> SEQUENCE: 16

Gln Val Gln Leu Val Gln Ser Gly Gly Gly Val Val Gln Pro Gly Arg
1               5                   10                  15

Ser Leu Arg Leu Ser Cys Lys Ala Ser Gly Tyr Thr Phe Thr Arg Tyr
            20                  25                  30

Thr Met His Trp Val Arg Gln Ala Pro Gly Lys Cys Leu Glu Trp Ile
        35                  40                  45

Gly Tyr Ile Asn Pro Ser Arg Gly Tyr Thr Asn Tyr Asn Gln Lys Phe
    50                  55                  60

Lys Asp Arg Phe Thr Ile Ser Arg Asp Asn Ser Lys Asn Thr Ala Phe
65                  70                  75                  80

Leu Gln Met Asp Ser Leu Arg Pro Glu Asp Thr Gly Val Tyr Phe Cys
                85                  90                  95

Ala Arg Tyr Tyr Asp Asp His Tyr Ser Leu Asp Tyr Trp Gly Gln Gly
            100                 105                 110

Thr Pro Val Thr Val Ser Ser Gly Gly Gly Ser Gly Gly Gly Gly
        115                 120                 125

Ser Gly Gly Gly Ser Gly Gly Gly Ser Gly Gly Gly Ser
    130                 135                 140

Asp Ile Gln Met Thr Gln Ser Pro Ser Ser Leu Ser Ala Ser Val Gly
145                 150                 155                 160

Asp Arg Val Thr Ile Thr Cys Ser Ala Ser Ser Ser Val Ser Tyr Met
                165                 170                 175

Asn Trp Tyr Gln Gln Thr Pro Gly Lys Ala Pro Lys Arg Trp Ile Tyr
            180                 185                 190

Asp Thr Ser Lys Leu Ala Ser Gly Val Pro Ser Arg Phe Ser Gly Ser
        195                 200                 205

Gly Ser Gly Thr Asp Tyr Thr Phe Thr Ile Ser Ser Leu Gln Pro Glu
    210                 215                 220

Asp Ile Ala Thr Tyr Tyr Cys Gln Gln Trp Ser Ser Asn Pro Phe Thr
225                 230                 235                 240

Phe Gly Cys Gly Thr Lys Leu Gln Ile Thr Arg
                245                 250

<210> SEQ ID NO 17
<211> LENGTH: 256
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 17

Gln Val Gln Leu Val Gln Ser Gly Gly Gly Val Val Gln Pro Gly Arg
1               5                   10                  15

Ser Leu Arg Leu Ser Cys Lys Ala Ser Gly Tyr Thr Phe Thr Arg Tyr
            20                  25                  30

Thr Met His Trp Val Arg Gln Ala Pro Gly Lys Cys Leu Glu Trp Ile
        35                  40                  45

Gly Tyr Ile Asn Pro Ser Arg Gly Tyr Thr Asn Tyr Asn Gln Lys Phe
    50                  55                  60

Lys Asp Arg Phe Thr Ile Ser Arg Asp Asn Ser Lys Asn Thr Ala Phe
65                  70                  75                  80

Leu Gln Met Asp Ser Leu Arg Pro Glu Asp Thr Gly Val Tyr Phe Cys

```
                    85                  90                  95
Ala Arg Tyr Tyr Asp Asp His Tyr Ser Leu Asp Tyr Trp Gln Gly
                100                 105                 110

Thr Pro Val Thr Val Ser Ser Gly Gly Gly Ser Gly Gly Gly Gly
            115                 120                 125

Ser Gly Gly Gly Ser Gly Gly Gly Ser Gly Gly Gly Ser
    130                 135                 140

Gly Gly Gly Gly Ser Asp Ile Gln Met Thr Gln Ser Pro Ser Ser Leu
145                 150                 155                 160

Ser Ala Ser Val Gly Asp Arg Val Thr Ile Thr Cys Ser Ala Ser Ser
                165                 170                 175

Ser Val Ser Tyr Met Asn Trp Tyr Gln Gln Thr Pro Gly Lys Ala Pro
                180                 185                 190

Lys Arg Trp Ile Tyr Asp Thr Ser Lys Leu Ala Ser Gly Val Pro Ser
                195                 200                 205

Arg Phe Ser Gly Ser Gly Ser Gly Thr Asp Tyr Thr Phe Thr Ile Ser
            210                 215                 220

Ser Leu Gln Pro Glu Asp Ile Ala Thr Tyr Tyr Cys Gln Gln Trp Ser
225                 230                 235                 240

Ser Asn Pro Phe Thr Phe Gly Cys Gly Thr Lys Leu Gln Ile Thr Arg
                245                 250                 255

<210> SEQ ID NO 18
<211> LENGTH: 260
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 18

Ser His Val Lys Leu Gln Glu Ser Gly Pro Gly Leu Val Gln Pro Ser
1               5                   10                  15

Gln Ser Leu Ser Leu Thr Cys Thr Val Ser Gly Phe Ser Leu Thr Asp
                20                  25                  30

Tyr Gly Val His Trp Val Arg Gln Ser Pro Gly Lys Gly Leu Glu Trp
            35                  40                  45

Leu Gly Val Ile Trp Ser Gly Gly Thr Ala Tyr Asn Thr Ala Leu
        50                  55                  60

Ile Ser Arg Leu Asn Ile Tyr Arg Asp Asn Ser Lys Asn Gln Val Phe
65                  70                  75                  80

Leu Glu Met Asn Ser Leu Gln Ala Glu Asp Thr Ala Met Tyr Tyr Cys
                85                  90                  95

Ala Arg Arg Gly Ser Tyr Pro Tyr Asn Tyr Phe Asp Ala Trp Gly Cys
                100                 105                 110

Gly Thr Thr Val Thr Val Ser Ser Gly Gly Gly Gly Ser Gly Gly Gly
            115                 120                 125

Gly Ser Gly Gly Gly Gly Ser Gly Gly Gly Ser Gly Gly Gly Gly
        130                 135                 140

Ser Gly Gly Gly Gly Ser Gln Ala Val Val Ile Gln Glu Ser Ala Leu
145                 150                 155                 160

Thr Thr Pro Pro Gly Glu Thr Val Thr Leu Thr Cys Gly Ser Ser Thr
                165                 170                 175

Gly Ala Val Thr Ala Ser Asn Tyr Ala Asn Trp Val Gln Glu Lys Pro
                180                 185                 190
```

```
Asp His Cys Phe Thr Gly Leu Ile Gly Gly His Asn Asn Arg Pro Pro
            195                 200                 205

Gly Val Pro Ala Arg Phe Ser Gly Ser Leu Ile Gly Asp Lys Ala Ala
    210                 215                 220

Leu Thr Ile Ala Gly Thr Gln Thr Glu Asp Glu Ala Ile Tyr Phe Cys
225                 230                 235                 240

Ala Leu Trp Tyr Ser Asp His Trp Val Ile Gly Gly Thr Arg Leu
                245                 250                 255

Thr Val Leu Gly
            260

<210> SEQ ID NO 19
<211> LENGTH: 510
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 19

Met Gly Trp Ser Cys Ile Ile Leu Phe Leu Val Ala Thr Ala Thr Gly
1               5                   10                  15

Glu Ile Val Leu Thr Gln Ser Pro Ala Thr Leu Ser Val Ser Leu Gly
            20                  25                  30

Glu Arg Ala Thr Ile Ser Cys Arg Ala Ser Glu Ser Val Asp Asn Tyr
        35                  40                  45

Gly Ile Ser Phe Met Asn Trp Phe Gln Gln Lys Pro Gly Gln Pro Pro
    50                  55                  60

Arg Leu Leu Ile Tyr Ala Ala Ser Asn Gln Gly Ser Gly Val Pro Ala
65                  70                  75                  80

Arg Phe Ser Gly Ser Gly Pro Gly Thr Asp Phe Thr Leu Thr Ile Ser
                85                  90                  95

Ser Met Glu Pro Glu Asp Phe Ala Met Tyr Phe Cys Gln Gln Ser Lys
            100                 105                 110

Glu Val Pro Trp Thr Phe Gly Gly Gly Thr Lys Leu Glu Ile Lys Arg
        115                 120                 125

Thr Val Ala Ala Pro Ser Val Phe Ile Phe Pro Pro Ser Asp Glu Gln
    130                 135                 140

Leu Lys Ser Gly Thr Ala Ser Val Val Cys Leu Leu Asn Asn Phe Tyr
145                 150                 155                 160

Pro Arg Glu Ala Lys Val Gln Trp Lys Val Asp Asn Ala Leu Gln Ser
                165                 170                 175

Gly Asn Ser Gln Glu Ser Val Thr Glu Gln Asp Ser Lys Asp Ser Thr
            180                 185                 190

Tyr Ser Leu Ser Ser Thr Leu Thr Leu Ser Lys Ala Asp Tyr Glu Lys
        195                 200                 205

His Lys Val Tyr Ala Cys Glu Val Thr His Gln Gly Leu Ser Ser Pro
    210                 215                 220

Val Thr Lys Ser Phe Asn Arg Gly Glu Cys Thr Ser Gly Gly Gly Gly
225                 230                 235                 240

Ser Gly Gly Gly Gly Ser Gly Gly Gly Ser His Val Lys Leu Gln
                245                 250                 255

Glu Ser Gly Pro Gly Leu Val Gln Pro Ser Gln Ser Leu Ser Leu Thr
            260                 265                 270

Cys Thr Val Ser Gly Phe Ser Leu Thr Asp Tyr Gly Val His Trp Val
        275                 280                 285
```

Arg Gln Ser Pro Gly Lys Gly Leu Glu Trp Leu Gly Val Ile Trp Ser
            290                 295                 300

Gly Gly Gly Thr Ala Tyr Asn Thr Ala Leu Ile Ser Arg Leu Asn Ile
305                 310                 315                 320

Tyr Arg Asp Asn Ser Lys Asn Gln Val Phe Leu Glu Met Asn Ser Leu
                325                 330                 335

Gln Ala Glu Asp Thr Ala Met Tyr Tyr Cys Ala Arg Arg Gly Ser Tyr
            340                 345                 350

Pro Tyr Asn Tyr Phe Asp Ala Trp Gly Cys Gly Thr Thr Val Thr Val
        355                 360                 365

Ser Ser Gly Gly Gly Gly Ser Gly Gly Gly Gly Ser Gly Gly Gly Gly
370                 375                 380

Ser Gly Gly Gly Gly Ser Gly Gly Gly Gly Ser Gly Gly Gly Gly Ser
385                 390                 395                 400

Gln Ala Val Val Ile Gln Glu Ser Ala Leu Thr Thr Pro Pro Gly Glu
                405                 410                 415

Thr Val Thr Leu Thr Cys Gly Ser Ser Thr Gly Ala Val Thr Ala Ser
            420                 425                 430

Asn Tyr Ala Asn Trp Val Gln Glu Lys Pro Asp His Cys Phe Thr Gly
        435                 440                 445

Leu Ile Gly Gly His Asn Asn Arg Pro Pro Gly Val Pro Ala Arg Phe
450                 455                 460

Ser Gly Ser Leu Ile Gly Asp Lys Ala Ala Leu Thr Ile Ala Gly Thr
465                 470                 475                 480

Gln Thr Glu Asp Glu Ala Ile Tyr Phe Cys Ala Leu Trp Tyr Ser Asp
                485                 490                 495

His Trp Val Ile Gly Gly Gly Thr Arg Leu Thr Val Leu Gly
            500                 505                 510

<210> SEQ ID NO 20
<211> LENGTH: 462
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 20

Met Gly Trp Ser Cys Ile Ile Leu Phe Leu Val Ala Thr Ala Thr Gly
1               5                   10                  15

Glu Val Gln Leu Val Gln Ser Gly Pro Glu Val Val Lys Pro Gly Ala
            20                  25                  30

Ser Val Lys Ile Ser Cys Lys Ala Ser Gly Tyr Thr Phe Thr Asp Tyr
        35                  40                  45

Asn Met His Trp Val Arg Gln Ala His Gly Gln Ser Leu Glu Trp Ile
    50                  55                  60

Gly Tyr Ile Tyr Pro Tyr Asn Gly Gly Thr Gly Tyr Asn Gln Lys Phe
65                  70                  75                  80

Lys Ser Arg Ala Thr Leu Thr Val Asp Asn Ser Ala Ser Thr Ala Tyr
                85                  90                  95

Met Glu Val Ser Ser Leu Arg Ser Glu Asp Thr Ala Val Tyr Tyr Cys
            100                 105                 110

Ala Arg Gly Arg Pro Ala Met Asp Tyr Trp Gly Gln Gly Thr Leu Val
        115                 120                 125

Thr Val Ser Ser Ala Ser Thr Lys Gly Pro Ser Val Phe Pro Leu Ala

```
                130                 135                 140
Pro Ser Ser Lys Ser Thr Ser Gly Gly Thr Ala Ala Leu Gly Cys Leu
145                 150                 155                 160

Val Lys Asp Tyr Phe Pro Glu Pro Val Thr Val Ser Trp Asn Ser Gly
                165                 170                 175

Ala Leu Thr Ser Gly Val His Thr Phe Pro Ala Val Leu Gln Ser Ser
            180                 185                 190

Gly Leu Tyr Ser Leu Ser Ser Val Val Thr Val Pro Ser Ser Ser Leu
                195                 200                 205

Gly Thr Gln Thr Tyr Ile Cys Asn Val Asn His Lys Pro Ser Asn Thr
            210                 215                 220

Lys Val Asp Lys Arg Val Glu Pro Lys Ser Cys Asp Lys Thr His Thr
225                 230                 235                 240

Cys Pro Pro Cys Pro Ala Pro Glu Ala Ala Gly Gly Pro Ser Val Phe
                245                 250                 255

Leu Phe Pro Pro Lys Pro Lys Asp Thr Leu Met Ile Ser Arg Thr Pro
            260                 265                 270

Glu Val Thr Cys Val Val Val Asp Val Ser His Glu Asp Pro Glu Val
                275                 280                 285

Lys Phe Asn Trp Tyr Val Asp Gly Val Glu Val His Asn Ala Lys Thr
            290                 295                 300

Lys Pro Arg Glu Glu Gln Tyr Asn Ser Thr Tyr Arg Val Val Ser Val
305                 310                 315                 320

Leu Thr Val Leu His Gln Asp Trp Leu Asn Gly Lys Glu Tyr Lys Cys
                325                 330                 335

Lys Val Ser Asn Lys Ala Leu Pro Ala Pro Ile Glu Lys Thr Ile Ser
            340                 345                 350

Lys Ala Lys Gly Gln Pro Arg Glu Pro Gln Val Tyr Thr Leu Pro Pro
                355                 360                 365

Ser Arg Asp Glu Leu Thr Lys Asn Gln Val Ser Leu Thr Cys Leu Val
            370                 375                 380

Lys Gly Phe Tyr Pro Ser Asp Ile Ala Val Glu Trp Glu Ser Asn Gly
385                 390                 395                 400

Gln Pro Glu Asn Asn Tyr Lys Thr Thr Pro Pro Val Leu Asp Ser Asp
                405                 410                 415

Gly Ser Phe Phe Leu Tyr Ser Lys Leu Thr Val Asp Lys Ser Arg Trp
            420                 425                 430

Gln Gln Gly Asn Val Phe Ser Cys Ser Val Met His Glu Ala Leu His
                435                 440                 445

Asn His Tyr Thr Gln Lys Ser Leu Ser Leu Ser Pro Gly Lys
            450                 455                 460

<210> SEQ ID NO 21
<211> LENGTH: 462
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 21

Met Gly Trp Ser Cys Ile Ile Leu Phe Leu Val Ala Thr Ala Thr Gly
1               5                   10                  15

Glu Val Gln Leu Val Gln Ser Gly Pro Glu Val Val Lys Pro Gly Ala
            20                  25                  30
```

```
Ser Val Lys Ile Ser Cys Lys Ala Ser Gly Tyr Thr Phe Thr Asp Tyr
             35                  40                  45

Asn Met His Trp Val Arg Gln Ala His Gly Gln Ser Leu Glu Trp Ile
 50                  55                  60

Gly Tyr Ile Tyr Pro Tyr Asn Gly Gly Thr Gly Tyr Asn Gln Lys Phe
 65                  70                  75                  80

Lys Ser Arg Ala Thr Leu Thr Val Asp Asn Ser Ala Ser Thr Ala Tyr
                 85                  90                  95

Met Glu Val Ser Ser Leu Arg Ser Glu Asp Thr Ala Val Tyr Tyr Cys
            100                 105                 110

Ala Arg Gly Arg Pro Ala Met Asp Tyr Trp Gly Gln Gly Thr Leu Val
            115                 120                 125

Thr Val Ser Ser Ala Ser Thr Lys Gly Pro Ser Val Phe Pro Leu Ala
130                 135                 140

Pro Ser Ser Lys Ser Thr Ser Gly Gly Thr Ala Ala Leu Gly Cys Leu
145                 150                 155                 160

Val Lys Asp Tyr Phe Pro Glu Pro Val Thr Val Ser Trp Asn Ser Gly
                165                 170                 175

Ala Leu Thr Ser Gly Val His Thr Phe Pro Ala Val Leu Gln Ser Ser
            180                 185                 190

Gly Leu Tyr Ser Leu Ser Ser Val Val Thr Val Pro Ser Ser Ser Leu
        195                 200                 205

Gly Thr Gln Thr Tyr Ile Cys Asn Val Asn His Lys Pro Ser Asn Thr
            210                 215                 220

Lys Val Asp Lys Arg Val Glu Pro Lys Ser Cys Asp Lys Thr His Thr
225                 230                 235                 240

Cys Pro Pro Cys Pro Ala Pro Glu Ala Ala Gly Gly Pro Ser Val Phe
                245                 250                 255

Leu Phe Pro Pro Lys Pro Lys Asp Thr Leu Met Ile Ser Arg Thr Pro
            260                 265                 270

Glu Val Thr Cys Val Val Val Asp Val Ser His Glu Asp Pro Glu Val
        275                 280                 285

Lys Phe Asn Trp Tyr Val Asp Gly Val Glu Val His Asn Ala Lys Thr
290                 295                 300

Lys Pro Arg Glu Glu Gln Tyr Asn Ser Thr Tyr Arg Val Val Ser Val
305                 310                 315                 320

Leu Thr Val Leu His Gln Asp Trp Leu Asn Gly Lys Glu Tyr Lys Cys
                325                 330                 335

Ala Val Ser Asn Lys Ala Leu Pro Ala Pro Ile Glu Lys Thr Ile Ser
            340                 345                 350

Lys Ala Lys Gly Gln Pro Arg Glu Pro Gln Val Tyr Thr Leu Pro Pro
        355                 360                 365

Ser Arg Asp Glu Leu Thr Lys Asn Gln Val Ser Leu Thr Cys Leu Val
            370                 375                 380

Lys Gly Phe Tyr Pro Ser Asp Ile Ala Val Glu Trp Glu Ser Asn Gly
385                 390                 395                 400

Gln Pro Glu Asn Asn Tyr Lys Thr Thr Pro Pro Val Leu Asp Ser Asp
                405                 410                 415

Gly Ser Phe Phe Leu Tyr Ser Lys Leu Thr Val Asp Lys Ser Arg Trp
            420                 425                 430

Gln Gln Gly Asn Val Phe Ser Cys Ser Val Met His Glu Ala Leu His
        435                 440                 445

Asn His Tyr Thr Gln Lys Ser Leu Ser Leu Ser Pro Gly Lys
```

<210> SEQ ID NO 22
<211> LENGTH: 462
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 22

```
Met Gly Trp Ser Cys Ile Ile Leu Phe Leu Val Ala Thr Ala Thr Gly
1               5                   10                  15

Glu Val Gln Leu Val Gln Ser Gly Pro Glu Val Val Lys Pro Gly Ala
            20                  25                  30

Ser Val Lys Ile Ser Cys Lys Ala Ser Gly Tyr Thr Phe Thr Asp Tyr
        35                  40                  45

Asn Met His Trp Val Arg Gln Ala His Gly Gln Ser Leu Glu Trp Ile
    50                  55                  60

Gly Tyr Ile Tyr Pro Tyr Asn Gly Gly Thr Gly Tyr Asn Gln Lys Phe
65                  70                  75                  80

Lys Ser Arg Ala Thr Leu Thr Val Asp Asn Ser Ala Ser Thr Ala Tyr
                85                  90                  95

Met Glu Val Ser Ser Leu Arg Ser Glu Asp Thr Ala Val Tyr Tyr Cys
            100                 105                 110

Ala Arg Gly Arg Pro Ala Met Asp Tyr Trp Gly Gln Gly Thr Leu Val
        115                 120                 125

Thr Val Ser Ser Ala Ser Thr Lys Gly Pro Ser Val Phe Pro Leu Ala
130                 135                 140

Pro Ser Ser Lys Ser Thr Ser Gly Gly Thr Ala Ala Leu Gly Cys Leu
145                 150                 155                 160

Val Lys Asp Tyr Phe Pro Glu Pro Val Thr Val Ser Trp Asn Ser Gly
                165                 170                 175

Ala Leu Thr Ser Gly Val His Thr Phe Pro Ala Val Leu Gln Ser Ser
            180                 185                 190

Gly Leu Tyr Ser Leu Ser Ser Val Val Thr Val Pro Ser Ser Ser Leu
        195                 200                 205

Gly Thr Gln Thr Tyr Ile Cys Asn Val Asn His Lys Pro Ser Asn Thr
    210                 215                 220

Lys Val Asp Lys Arg Val Glu Pro Lys Ser Cys Asp Lys Thr His Thr
225                 230                 235                 240

Cys Pro Pro Cys Pro Ala Pro Glu Leu Leu Gly Gly Pro Ser Val Phe
                245                 250                 255

Leu Phe Pro Pro Lys Pro Lys Asp Thr Leu Met Ile Ser Arg Thr Pro
            260                 265                 270

Glu Val Thr Cys Val Val Val Ala Val Ser His Glu Asp Pro Glu Val
        275                 280                 285

Lys Phe Asn Trp Tyr Val Asp Gly Val Glu Val His Asn Ala Lys Thr
    290                 295                 300

Lys Pro Arg Glu Glu Gln Tyr Asn Ser Thr Tyr Arg Val Val Ser Val
305                 310                 315                 320

Leu Thr Val Leu His Gln Asp Trp Leu Asn Gly Lys Glu Tyr Lys Cys
                325                 330                 335

Lys Val Ser Asn Lys Ala Leu Pro Ala Pro Ile Glu Lys Thr Ile Ser
            340                 345                 350
```

```
Lys Ala Lys Gly Gln Pro Arg Glu Pro Gln Val Tyr Thr Leu Pro Pro
            355                 360                 365

Ser Arg Asp Glu Leu Thr Lys Asn Gln Val Ser Leu Thr Cys Leu Val
370                 375                 380

Lys Gly Phe Tyr Pro Ser Asp Ile Ala Val Glu Trp Glu Ser Asn Gly
385                 390                 395                 400

Gln Pro Glu Asn Asn Tyr Lys Thr Thr Pro Pro Val Leu Asp Ser Asp
                405                 410                 415

Gly Ser Phe Phe Leu Tyr Ser Lys Leu Thr Val Asp Lys Ser Arg Trp
            420                 425                 430

Gln Gln Gly Asn Val Phe Ser Cys Ser Val Met His Glu Ala Leu His
            435                 440                 445

Asn His Tyr Thr Gln Lys Ser Leu Ser Leu Ser Pro Gly Lys
450                 455                 460

<210> SEQ ID NO 23
<211> LENGTH: 1386
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 23
atgggctggt cctgcatcat cctgtttctg gtggctaccg ccaccggcga ggtgcagctg      60
gtgcagtctg gacccgaggt cgtgaagcct ggcgcctccg tgaagatctc ctgcaaggcc     120
tccggctaca ccttcaccga ctacaacatg cactgggtgc gacaggccca cggccagtcc     180
ctggaatgga tcggctacat ctacccctac aacggcggca ccggctacaa ccagaagttc     240
aagtctcggg ccaccctgac cgtggacaac tctgcctcta ccgcctacat ggaagtgtcc     300
tccctgagat ccgaggacac cgccgtgtac tactgcgcca ggcagacc cgccatggac      360 tattggggcc agggcaccct cgtgaccgtg tctagcgctt ctaccaaggg cccctctgtg     420
tttcctctgg cccccctccag caagtccacc tctggtggaa cagccgccct gggctgcctc     480
gtgaaggact actttcccga gcccgtgacc gtgtcctgga actctggcgc tctgacctct     540
ggcgtgcaca ccttccctgc tgtgctgcag tctagcggcc tgtactccct gtcctccgtc     600
gtgacagtgc cctccagctc tctgggcacc cagacctaca tctgcaacgt gaaccacaag     660
ccctccaata ccaaggtgga caagcgggtg gaacccaagt cctgcgacaa gacccacacc     720 tgtcccccctt gtcctgcccc tgaactgctg ggcggacctt ccgtgttcct gttcccccca     780
aagcccaagg acaccctgat gatctcccgg acccccgaag tgacctgcgt ggtggtggat     840
gtgtcccacg aggaccctga agtgaagttc aattggtacg tggacggcgt ggaagtgcac     900
aacgccaaga ccaagcctag agaggaacag tacgcctcca cctaccgggt ggtgtccgtg     960
ctgacagtgc tgcaccagga ctggctgaac ggcaaagagt acaagtgcgc cgtgtccaac    1020
aaggccctgc ctgcccccat cgaaaagacc atctccaagg ccaagggcca gccccgggaa    1080
ccccaggtgt acacactgcc cctagcagg gacgagctga ccaagaacca ggtgtccctg    1140
acctgtctcg tgaaaggctt ctaccccctcc gatatcgccg tggaatggga gtccaacggc    1200
cagcctgaga acaactacaa gaccaccccc cctgtgctgg actccgacgg ctcattcttc    1260
ctgtacagca agctgaccgt ggacaagtcc cggtggcagc agggcaacgt gttctcctgc    1320
tccgtgatgc acgaggccct gcacaaccac tacacccaga gtccctgtc cctgagcccc    1380 ggcaaa                                                               1386
```

<210> SEQ ID NO 24
<211> LENGTH: 462
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 24

Met Gly Trp Ser Cys Ile Ile Leu Phe Leu Val Ala Thr Ala Thr Gly
1               5                   10                  15

Glu Val Gln Leu Val Gln Ser Gly Pro Glu Val Lys Pro Gly Ala
            20                  25                  30

Ser Val Lys Ile Ser Cys Lys Ala Ser Gly Tyr Thr Phe Thr Asp Tyr
        35                  40                  45

Asn Met His Trp Val Arg Gln Ala His Gly Gln Ser Leu Glu Trp Ile
    50                  55                  60

Gly Tyr Ile Tyr Pro Tyr Asn Gly Gly Thr Gly Tyr Asn Gln Lys Phe
65                  70                  75                  80

Lys Ser Arg Ala Thr Leu Thr Val Asp Asn Ser Ala Ser Thr Ala Tyr
                85                  90                  95

Met Glu Val Ser Ser Leu Arg Ser Glu Asp Thr Ala Val Tyr Tyr Cys
            100                 105                 110

Ala Arg Gly Arg Pro Ala Met Asp Tyr Trp Gly Gln Gly Thr Leu Val
        115                 120                 125

Thr Val Ser Ser Ala Ser Thr Lys Gly Pro Ser Val Phe Pro Leu Ala
130                 135                 140

Pro Ser Ser Lys Ser Thr Ser Gly Gly Thr Ala Ala Leu Gly Cys Leu
145                 150                 155                 160

Val Lys Asp Tyr Phe Pro Glu Pro Val Thr Val Ser Trp Asn Ser Gly
                165                 170                 175

Ala Leu Thr Ser Gly Val His Thr Phe Pro Ala Val Leu Gln Ser Ser
            180                 185                 190

Gly Leu Tyr Ser Leu Ser Ser Val Val Thr Val Pro Ser Ser Ser Leu
        195                 200                 205

Gly Thr Gln Thr Tyr Ile Cys Asn Val Asn His Lys Pro Ser Asn Thr
210                 215                 220

Lys Val Asp Lys Arg Val Glu Pro Lys Ser Cys Asp Lys Thr His Thr
225                 230                 235                 240

Cys Pro Pro Cys Pro Ala Pro Glu Leu Leu Gly Gly Pro Ser Val Phe
                245                 250                 255

Leu Phe Pro Pro Lys Pro Lys Asp Thr Leu Met Ile Ser Arg Thr Pro
            260                 265                 270

Glu Val Thr Cys Val Val Val Asp Val Ser His Glu Asp Pro Glu Val
        275                 280                 285

Lys Phe Asn Trp Tyr Val Asp Gly Val Glu Val His Asn Ala Lys Thr
290                 295                 300

Lys Pro Arg Glu Glu Gln Tyr Ala Ser Thr Tyr Arg Val Val Ser Val
305                 310                 315                 320

Leu Thr Val Leu His Gln Asp Trp Leu Asn Gly Lys Glu Tyr Lys Cys
                325                 330                 335

Ala Val Ser Asn Lys Ala Leu Pro Ala Pro Ile Glu Lys Thr Ile Ser
            340                 345                 350

Lys Ala Lys Gly Gln Pro Arg Glu Pro Gln Val Tyr Thr Leu Pro Pro

| | | | | | | | | | | | |
|---|---|---|---|---|---|---|---|---|---|---|---|
| | | 355 | | | | 360 | | | | 365 | |
| Ser | Arg | Asp | Glu | Leu | Thr | Lys | Asn | Gln | Val | Ser | Leu | Thr | Cys | Leu | Val |
| | | 370 | | | | 375 | | | | 380 | |

Ser Arg Asp Glu Leu Thr Lys Asn Gln Val Ser Leu Thr Cys Leu Val
            370                 375                 380

Lys Gly Phe Tyr Pro Ser Asp Ile Ala Val Glu Trp Glu Ser Asn Gly
385                 390                 395                 400

Gln Pro Glu Asn Asn Tyr Lys Thr Thr Pro Pro Val Leu Asp Ser Asp
                    405                 410                 415

Gly Ser Phe Phe Leu Tyr Ser Lys Leu Thr Val Asp Lys Ser Arg Trp
                420                 425                 430

Gln Gln Gly Asn Val Phe Ser Cys Ser Val Met His Glu Ala Leu His
                435                 440                 445

Asn His Tyr Thr Gln Lys Ser Leu Ser Leu Ser Pro Gly Lys
450                 455                 460

<210> SEQ ID NO 25
<211> LENGTH: 1521
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 25

| | |
|---|---|
| atgggctggt cctgcatcat cctgtttctg gtggctaccg ccaccggcga gatcgtgctg | 60 |
| actcagtctc ctgccaccct gtccgtgtcc ctgggcgaga gagccaccat ctcttgcaga | 120 |
| gcctccgagt ccgtggacaa ctacggcatc tccttcatga actggttcca gcagaagccc | 180 |
| ggccagcctc ctcggctgct gatctacgcc gcttccaatc agggctctgg cgtgcccgct | 240 |
| agattctccg gatctggccc tggcaccgac tttaccctga ccatctcctc catggaaccc | 300 |
| gaggacttcg ccatgtactt tgccagcag tccaaagagg tgccctggac ctttggcgga | 360 |
| ggcaccaagc tggaaatcaa gcggaccgtg gccgctccct ccgtgttcat cttcccacct | 420 |
| tccgacgagc agctgaagtc cggcaccgct tctgtcgtgt gcctgctgaa caacttctac | 480 |
| ccccgcgagg ccaaggtgca gtggaaggtg acaacgccc tgcagtccgg caactcccag | 540 |
| gaatccgtga ccgagcagga ctccaaggac agcacctact ccctgtcctc caccctgacc | 600 |
| ctgagcaagg ccgactacga aagcacaag gtgtacgcct gcgaagtgac ccaccagggc | 660 |
| ctgtctagcc ccgtgaccaa gtcttcaac cggggcgagt gcactagtgg cggcggagga | 720 |
| tctggcggag gtggaagcgg agggggagga tctcaggtgc agctggtgca gagcggaggc | 780 |
| ggagtggtgc agcctggcag atccctgaga ctgtcctgca aggcctccgg ctacaccttc | 840 |
| acccggtaca ccatgcactg ggtgcgacag gcccctggca agtgcctgga atggatcggc | 900 |
| tacatcaacc cctccgggg ctacaccaac tacaaccaga agttcaagga ccggttcacc | 960 |
| atctcccggg acaactccaa gaacaccgcc tttctgcaga tggactccct gcggcctgag | 1020 |
| gataccggcg tgtacttctg cgcccggtac tacgacgacc actactccct ggactactgg | 1080 |
| ggccagggaa cccctgtgac agtgtcatct ggtggcggag aagtggggg aggcggatca | 1140 |
| ggtggtggtg gatcaggcgg gggaggttca ggggtggcg gttctggggg aggggctct | 1200 |
| gatattcaga tgactcagag cccttccagc ctgagcgcct ccgtgggaga tcgcgtgaca | 1260 |
| attacctgct ctgcctcctc ctccgtgtct tacatgaatt ggtatcagca gaccctgggg | 1320 |
| aaggctccta gcggtggat ctacgacacc tccaagctgg cctctggcgt gcccagcagg | 1380 |
| ttttctggct ccggcagcgg cacagattat accttcacca tcagctccct gcagccagaa | 1440 |

```
gatatcgcta cctattattg tcagcagtgg tcctccaacc ctttcacctt cggctgcggc    1500
acaaagctgc agatcacaag a                                              1521
```

<210> SEQ ID NO 26
<211> LENGTH: 507
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 26

```
Met Gly Trp Ser Cys Ile Ile Leu Phe Leu Val Ala Thr Ala Thr Gly
1               5                   10                  15

Glu Ile Val Leu Thr Gln Ser Pro Ala Thr Leu Ser Val Ser Leu Gly
            20                  25                  30

Glu Arg Ala Thr Ile Ser Cys Arg Ala Ser Glu Ser Val Asp Asn Tyr
        35                  40                  45

Gly Ile Ser Phe Met Asn Trp Phe Gln Gln Lys Pro Gly Gln Pro Pro
    50                  55                  60

Arg Leu Leu Ile Tyr Ala Ala Ser Asn Gln Gly Ser Gly Val Pro Ala
65                  70                  75                  80

Arg Phe Ser Gly Ser Gly Pro Gly Thr Asp Phe Thr Leu Thr Ile Ser
                85                  90                  95

Ser Met Glu Pro Glu Asp Phe Ala Met Tyr Phe Cys Gln Gln Ser Lys
            100                 105                 110

Glu Val Pro Trp Thr Phe Gly Gly Gly Thr Lys Leu Glu Ile Lys Arg
        115                 120                 125

Thr Val Ala Ala Pro Ser Val Phe Ile Phe Pro Pro Ser Asp Glu Gln
    130                 135                 140

Leu Lys Ser Gly Thr Ala Ser Val Val Cys Leu Leu Asn Asn Phe Tyr
145                 150                 155                 160

Pro Arg Glu Ala Lys Val Gln Trp Lys Val Asp Asn Ala Leu Gln Ser
                165                 170                 175

Gly Asn Ser Gln Glu Ser Val Thr Glu Gln Asp Ser Lys Asp Ser Thr
            180                 185                 190

Tyr Ser Leu Ser Ser Thr Leu Thr Leu Ser Lys Ala Asp Tyr Glu Lys
        195                 200                 205

His Lys Val Tyr Ala Cys Glu Val Thr His Gln Gly Leu Ser Ser Pro
    210                 215                 220

Val Thr Lys Ser Phe Asn Arg Gly Glu Cys Thr Ser Gly Gly Gly Gly
225                 230                 235                 240

Ser Gly Gly Gly Gly Ser Gly Gly Gly Ser Gln Val Gln Leu Val
                245                 250                 255

Gln Ser Gly Gly Gly Val Val Gln Pro Gly Arg Ser Leu Arg Leu Ser
            260                 265                 270

Cys Lys Ala Ser Gly Tyr Thr Phe Thr Arg Tyr Thr Met His Trp Val
        275                 280                 285

Arg Gln Ala Pro Gly Lys Cys Leu Glu Trp Ile Gly Tyr Ile Asn Pro
    290                 295                 300

Ser Arg Gly Tyr Thr Asn Tyr Asn Gln Lys Lys Asp Arg Phe Thr
305                 310                 315                 320

Ile Ser Arg Asp Asn Ser Lys Asn Thr Ala Phe Leu Gln Met Asp Ser
                325                 330                 335

Leu Arg Pro Glu Asp Thr Gly Val Tyr Phe Cys Ala Arg Tyr Tyr Asp
```

```
                    340                 345                 350
Asp His Tyr Ser Leu Asp Tyr Trp Gly Gln Gly Thr Pro Val Thr Val
            355                 360                 365

Ser Ser Gly Gly Gly Ser Gly Gly Gly Ser Gly Gly Gly Gly
        370                 375                 380

Ser Gly Gly Gly Ser Gly Gly Gly Ser Gly Gly Gly Ser
385                 390                 395                 400

Asp Ile Gln Met Thr Gln Ser Pro Ser Ser Leu Ser Ala Ser Val Gly
                405                 410                 415

Asp Arg Val Thr Ile Thr Cys Ser Ala Ser Ser Val Ser Tyr Met
            420                 425                 430

Asn Trp Tyr Gln Gln Thr Pro Gly Lys Ala Pro Lys Arg Trp Ile Tyr
            435                 440                 445

Asp Thr Ser Lys Leu Ala Ser Gly Val Pro Ser Arg Phe Ser Gly Ser
        450                 455                 460

Gly Ser Gly Thr Asp Tyr Thr Phe Thr Ile Ser Ser Leu Gln Pro Glu
465                 470                 475                 480

Asp Ile Ala Thr Tyr Tyr Cys Gln Gln Trp Ser Ser Asn Pro Phe Thr
                485                 490                 495

Phe Gly Cys Gly Thr Lys Leu Gln Ile Thr Arg
                500                 505

<210> SEQ ID NO 27
<211> LENGTH: 256
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 27

Gln Val Gln Leu Val Gln Ser Gly Gly Gly Val Val Gln Pro Gly Arg
1               5                   10                  15

Ser Leu Arg Leu Ser Cys Lys Ala Ser Gly Tyr Thr Phe Thr Arg Tyr
            20                  25                  30

Thr Met His Trp Val Arg Gln Ala Pro Gly Lys Cys Leu Glu Trp Ile
        35                  40                  45

Gly Tyr Ile Asn Pro Ser Arg Gly Tyr Thr Asn Tyr Asn Gln Lys Phe
    50                  55                  60

Lys Asp Arg Phe Thr Ile Ser Arg Asp Asn Ser Lys Asn Thr Ala Phe
65                  70                  75                  80

Leu Gln Met Asp Ser Leu Arg Pro Glu Asp Thr Gly Val Tyr Phe Cys
                85                  90                  95

Ala Arg Tyr Tyr Asp Asp His Tyr Ser Leu Asp Tyr Trp Gly Gln Gly
            100                 105                 110

Thr Pro Val Thr Val Ser Ser Gly Gly Gly Ser Gly Gly Gly Gly
        115                 120                 125

Ser Gly Gly Gly Gly Ser Gly Gly Gly Ser Gly Gly Gly Ser
    130                 135                 140

Gly Gly Gly Gly Ser Asp Ile Gln Met Thr Gln Ser Pro Ser Ser Leu
145                 150                 155                 160

Ser Ala Ser Val Gly Asp Arg Val Thr Ile Thr Cys Ser Ala Ser Ser
                165                 170                 175

Ser Val Ser Tyr Met Asn Trp Tyr Gln Gln Thr Pro Gly Lys Ala Pro
            180                 185                 190
```

```
Lys Arg Trp Ile Tyr Asp Thr Ser Lys Leu Ala Ser Gly Val Pro Ser
        195                 200                 205

Arg Phe Ser Gly Ser Gly Ser Gly Thr Asp Tyr Thr Phe Thr Ile Ser
    210                 215                 220

Ser Leu Gln Pro Glu Asp Ile Ala Thr Tyr Tyr Cys Gln Gln Trp Ser
225                 230                 235                 240

Ser Asn Pro Phe Thr Phe Gly Cys Gly Thr Lys Leu Gln Ile Thr Arg
                245                 250                 255

<210> SEQ ID NO 28
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

Gly Gly Gly Gly Ser
1               5

<210> SEQ ID NO 29
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Gly Gly Gly Gly Ser Gly Gly Gly Gly Ser Gly Gly Gly Gly Ser
1               5                   10                  15
```

ANTI-CD33 ANTIBODY AGENTS

CROSS-REFERENCE TO RELATED APPLICATIONS

This application is a U.S. National Application of PCT Application PCT/US18/29191, filed on Apr. 24, 2018, which claims priority to and the benefit of U.S. Patent Application No. 62/489,269, filed on Apr. 24, 2017, the disclosures of each of which is incorporated herein by reference in its entirety.

SEQUENCE LISTING

The instant application contains a Sequence Listing which has been submitted electronically in ASCII format and is hereby incorporated by reference in its entirety. Said ASCII copy, created on Oct. 22, 2019, is named 2003080_1733_Sequence_Listing.txt and is 67,279 bytes in size.

INTRODUCTION

Antibody-based therapeutics offer significant promise, particularly in the treatment of cancer. A variety of antibody formats, including monoclonal, murine, chimeric, humanized, human, full-length, Fab, pegylated, radiolabeled, drug-conjugated, multi-specific, etc., are being developed. As of 2012, at least 34 therapeutic antibody agents had received marketing approval in the United States or Europe (see Reichert, mAbs 4:3, 413, May/June 2012, incorporated herein by reference). However, development of particular effective antibody agents remains a challenge.

SUMMARY

The present disclosure provides, among other things, particular multispecific antibody agents (e.g., bispecific antibody agents) that bind to an epitope of human CD33 protein. In some embodiments, multispecific antibody agents (e.g., bispecific antibody agents) include binding moieties of humanized anti-CD33 antibody, such as a humanized M195 (referred to herein as huM195). The present disclosure encompasses the recognition that particular multispecific antibody agents that include a binding moiety that binds CD33 have improved functional characteristics as described herein.

In some embodiments, multispecific antibody agents of the present disclosure include a first binding moiety based on huM195 (i.e., an anti-CD33 binding moiety) and a second binding moiety. In some embodiments, a second binding moiety binds to an agent on immune cells. In some embodiments, a second binding moiety binds to an agent on T-cells (e.g., CD3). In some embodiments, a second binding moiety interacts with an organic or inorganic compound. The present disclosure encompasses the recognition that such multispecific antibody agents that can bind to CD33 and a second agent are useful for treatment and diagnoses of diseases associated with CD33, such as, for example, CD33-expressing cancers.

In some embodiments, a provided multispecific antibody agent (e.g., a bispecific antibody agent, such as CD33-BsAb) includes two identical immunoglobulin heavy chains and two identical fusion polypeptides. In some embodiments, each fusion polypeptide includes: an immunoglobulin light chain domain and a binding domain such as a single chain variable fragment (scFv) (See, e.g., FIG. 1A). In some embodiments, each fusion polypeptide includes: a scFv fused to a light chain, a scFv-CL1, or a VHH-CL1, or any binding domain attached to a light chain (or a portion thereof). In some embodiments, provided multispecific antibody agents (e.g., bispecific antibody agents, such as CD33-BsAb) comprise heavy chains that each include a heavy chain variable domain sequence identified as SEQ ID NO:1 or 2. In some embodiments, a light chain portion of a fusion polypeptide comprises a light chain variable domain sequence identified as SEQ ID NO:3 or 4.

In some embodiments, a provided multispecific antibody agent (e.g., bispecific antibody agent, such as CD33-BsAb) includes a heavy chain and a fusion polypeptide, wherein the heavy chain variable region includes a sequence that is at least about 70% (e.g., at least about 70%, 75%, 80%, 85%, 90%, 95%, 96%, 97%, 98%, or 99%) identical to SEQ ID NO:1 or 2 and wherein the light chain portion of the fusion polypeptide includes a sequence that is at least about 70% (e.g., at least about 70%, 75%, 80%, 85%, 90%, 95%, 96%, 97%, 98%, or 99%) identical to SEQ ID NO: 3 or 4.

In some embodiments, provided are multispecific antibody agents (e.g., bispecific antibody agents, such as CD33-BsAb) that comprise heavy chains that each comprise a sequence identified as SEQ ID NO:9. In some embodiments, a light chain portion of a fusion polypeptide comprises a sequence identified as SEQ ID NO:10. In some embodiments, a provided bispecific antibody agent, e.g., CD33-BsAb, includes a heavy chain and a fusion polypeptide, wherein the heavy chain variable region includes a sequence that is at least about 50% (e.g., at least about 55%, 60%, 65%, 70%, 75%, 80%, 85%, 90%, 95%, 96%, 97%, 98%, or 99%) identical to SEQ ID NO:9 and wherein the light chain portion of the fusion polypeptide includes a sequence that is at least about 50% (e.g., at least about 55%, 60%, 65%, 70%, 75%, 80%, 85%, 90%, 95%, 96%, 97%, 98%, or 99%) identical to SEQ ID NO: 10.

In some embodiments, a provided multispecific antibody agent (e.g., a bispecific antibody agent, such as CD33-BsAb) includes a fusion polypeptide including an scFv that binds a second target fused to the C-terminus of an immunoglobulin light chain (or antigen-binding portion thereof), e.g., an anti-CD33 light chain. In some embodiments, the fusion polypeptide further comprises a linker.

In some particular embodiments, provided multispecific antibody agents (e.g., bispecific antibody agents, such as a CD33-BsAb), or sequences thereof, may comprise an anti-CD33 variable domain and at least one other binding domain such as, for example, anti-OKT3 for retargeting T cells for tumor cytotoxicity, or a Benzyl-DOTA-metal binding domain, e.g., C825, for multistep pretargeting, or Clone 35, CD137, for ADCC with anti-41BB-scFv as agonist, or with CD137L, 4-1BBL for ADC with 4-1BBL as agonist. In some embodiments, a multispecific antibody agent is a bispecific antibody agent that comprises an scFv that binds a T-cell antigen. In some embodiments, a T-cell antigen is CD3. In some embodiments, a bispecific antibody agent comprises a humanized OKT3 scFv. In some embodiments, a fusion polypeptide comprises an scFv comprising a sequence identified as any of SEQ ID NOs: 11-17 and 27.

In some embodiments, provided multispecific antibody agents (e.g., bispecific antibody agents, such as CD33-BsAb) comprise heavy chains that each comprise a sequence identified as SEQ ID NO: 24. In some embodiments, said multispecific antibody agents (e.g., bispecific antibody agents, such as CD33-BsAb) further comprises fusion polypeptides that each comprise a sequence identified as SEQ ID NO: 26.

In some embodiments, a multispecific antibody agent (e.g., a bispecific antibody agent, such as a CD33-BsAb agent) comprises an scFv that specifically binds to a Benzyl-DOTA-metal. In some embodiments, an scFv that specifically binds to a Benzyl-DOTA-metal is a C825 scFv. In some embodiments, the fusion polypeptide comprises an scFv comprising a sequence identified as SEQ ID NO: 18. In some embodiments the fusion polypeptide comprises an anti-CD33 immunoglobulin light chain sequence fused to a Benzyl-DOTA-metal binding scFv. In some embodiments, an anti-CD33 anti-Benzyl-DOTA fusion polypeptide further comprises a linker. In some embodiments, an anti-CD33 anti-Benzyl-DOTA fusion polypeptide comprises a sequence identified as SEQ ID NO: 19.

In some embodiments, multispecific antibody agents (e.g., a bispecific antibody agents, such as CD33-BsAb) comprise a variant Fc region, wherein said variant Fc region comprises at least one amino acid modification relative to a wild-type Fc region. In certain embodiments, Fc modifications may include, but are not limited to modifications that alter effector function. In some embodiments, Fc variants comprise one or more engineered glycoforms, i.e., a carbohydrate composition that is covalently attached to a molecule comprising an Fc region, wherein said carbohydrate composition differs chemically from that of a parent molecule comprising an Fc region.

In some embodiments, a multispecific antibody agent (e.g., a bispecific antibody agent, such as a CD33-BsAb) comprises an Fc region with a N297A mutation in the CH2 domain, as numbered according to Kabat. In some embodiments, a heavy chain comprising a N297A mutation lacks glycosylation. In some embodiments, a heavy chain comprising a N297A mutation lacks FcR or C1q binding. In some embodiments, an antibody agent comprises a heavy chain comprising an Fc region with one or more mutations selected from K322A and D265A. In some embodiments, an antibody agent comprises a heavy chain comprising an Fc region comprising a N297A mutation and a K322A mutation. In some embodiments, an antibody agent comprises a heavy chain comprising an Fc region comprising a N297A mutation and a D265A mutation. In some embodiments, an antibody agent comprises a heavy chain comprising an Fc region comprising a N297A mutation, a D265A mutation, and a K322A mutation. In some embodiments, the heavy chain comprises a sequence identified as any one of SEQ ID NOs: 20-22.

In some embodiments, a multispecific antibody agent (e.g., a bispecific antibody agent, such as a CD33-BsAb) is characterized by bivalent binding to an antigen (e.g., CD33). In some embodiments, a multispecific antibody agent (e.g., a bispecific antibody agent, such as a CD33-BsAb agent) is tetravalent, for example with bivalent binding to two different antigens.

In some embodiments, a multispecific antibody agent (e.g., a bispecific antibody agent, such as a CD33-BsAb) binds to an AML cell line (e.g. HL60) with an $EC_{50}$ in a range of 0.1 pM to 1 µM. In some embodiments, a multispecific antibody agent (e.g., a bispecific antibody agent, such as a CD33-BsAb) has a molecular weight above a typical kidney excretion threshold (e.g., a molecular weight greater than about 70 kDa).

Also are provided are nucleotide sequences encoding any or all of the polypeptide sequences included in a multispecific antibody agent as described herein, optionally together with one or more regulatory elements, and/or vector sequences (e.g., integration and/or replication signals). In some embodiments are provided a nucleic acid molecule encoding a humanized anti-CD33 antibody heavy chain, said nucleic acid identified as SEQ ID NO: 23. In some embodiments are provided an nucleic acid molecule encoding a fusion polypeptide, said nucleic acid identified as SEQ ID NO: 25. In some embodiments, are also recombinant vectors that include nucleotide sequences encoding bispecific antibodies of the present disclosure. In some embodiments, provided nucleotide sequences and/or vectors are isolated.

Also provided are host cells that comprise a nucleic acid as described herein. In some embodiments, a host cell may be a eukaryotic cell; in some embodiments, a host cell may be a prokaryotic cell. In certain embodiments, a host cell may be a bacterial, yeast, insect, or mammalian cell. Particular exemplary prokaryotic host cells include E. coli cells; particular exemplary eukaryotic cells include, for example, COS cells, CHO cells (e.g., DG44 cells, CHO-S, CHO-K1, etc), and HEK 293 cells (e.g., Expi293F, HEK293T, etc).

Also provided are technologies for production of multispecific antibody agents as described herein (e.g., CD33-BsAb agent). In some embodiments, production of a multispecific antibody agent may involve, for example, a step of culturing the host cell in a culture medium under conditions allowing expression of a multispecific binding agent (e.g., a CD33-BsAb agent). Alternatively or additionally, in some embodiments, provided technologies involve separating a multispecific antibody agent (e.g., CD33-BsAb agent) from culture medium of a host cell that produced it.

The present disclosure also provides compositions comprising a multispecific antibody agent (e.g., a bispecific antibody agent, such as a CD33-BsAb). In some embodiments, a composition is a pharmaceutical composition. In some embodiments, a pharmaceutical composition further comprises a pharmaceutically acceptable carrier or diluent.

In some embodiments, provided multispecific antibody agents (e.g., bispecific antibody agents, such as CD33-BsAb) are useful and/or are used in manufacture of a pharmaceutical composition. In some embodiments, a pharmaceutical composition comprises a multispecific antibody agent (e.g., a bispecific antibody agent, such as a CD33-BsAb) and a pharmaceutically acceptable carrier. Also provided are methods of manufacturing pharmaceutical compositions; in some embodiments, such methods may comprise steps of combining a multispecific antibody agent (e.g., a bispecific antibody agent, such as a CD33-BsAb) with a pharmaceutically acceptable carrier and/or formulating such a combination for administration to a subject. In some embodiments, a pharmaceutical composition is formulated for parenteral delivery. In some embodiments, a pharmaceutical composition is for treatment of cancer (e.g., AML).

In some embodiments are provided methods comprising a step of: administering to a subject in need thereof a composition that comprises and/or delivers a multispecific antibody agent (e.g., a bispecific antibody agent, such as a CD33-BsAb). In some embodiments, a multispecific antibody agent of the present disclosure (e.g., a bispecific antibody agent, such as a CD33-BsAb) is a therapeutic agent. In some embodiments, a multispecific antibody agent of the present disclosure (e.g., a bispecific antibody agent, such as a CD33-BsAb) is a diagnostic agent.

In some embodiments are provided methods comprising a step of: administering to a subject in need thereof a composition that comprises and/or delivers a multispecific antibody agent (e.g., a bispecific antibody agent, such as a CD33-BsAb) to a subject that has been administered or will be administered IL2, such that the subject receives both. In some embodiments are provided methods comprising a step of: administering to a subject in need thereof a composition that comprises and/or delivers IL2 to a subject that has been administered or will be administered a multispecific antibody agent (e.g., a bispecific antibody agent, such as a CD33-BsAb), such that the subject receives both.

Provided herein are T cells that are armed and/or activated with a multispecific antibody agent of the present disclosure (e.g., a bispecific antibody agent, such as a CD33-BsAb). In some embodiments are provided a population of said T cells. In some embodiments are provided a composition comprising a T cell or population of T cells armed and/or activated with a multispecific antibody agent of the present disclosure (e.g., a bispecific antibody agent, such as a CD33-BsAb). In some embodiments, a T cell or population of T cells is armed with a multispecific antibody agent of the present disclosure (e.g., a bispecific antibody agent, such as a CD33-BsAb). In some embodiments, a T cell or population of T cells is activated with a multispecific antibody agent of the present disclosure (e.g., a bispecific antibody agent, such as a CD33-BsAb).

In some embodiments, provided are chimeric antigen receptor constructs (CAR) comprising a binding domain that comprises a multispecific antibody agent of the present disclosure (e.g., a bispecific antibody agent, such as a CD33-BsAb). In some embodiments, a CAR is a first generation, second generation or third generation CAR. In some embodiments, a CAR further comprises a transmembrane domain, a costimulatory signaling region, and a CD3 zeta signaling domain. In some embodiments, a CAR includes binding domain that comprises a CD33-bispecific antibody agent of the present disclosure, a transmembrane domain, a costimulatory signaling region, and a CD3 zeta signaling domain. Also provided herein are T cells that express a CAR of the present disclosure, i.e., a CAR-T cell. In some embodiments, provided are a population of CAR-T cells that express a CAR that includes a binding domain that comprises a multispecific antibody agent of the present disclosure (e.g., a bispecific antibody agent, such as a CD33-BsAb).

In some embodiments are provided Natural Killer (NK) cells that express a CAR of the present disclosure, i.e., a CAR-NK cell. In some embodiments, provided are a population of CAR-NK cells that express a CAR that includes a binding domain that comprises a multispecific antibody agent of the present disclosure (e.g., a bispecific antibody agent, such as a CD33-BsAb).

In some embodiments are provided compositions and methods can be used to treat or ameliorate a disease associated with CD33-expression in a subject. In some embodiments are provided compositions and methods can be used for diagnosis of a disease associated with CD33-expression. In some embodiments, a disease associated with CD33-expression is a malignant disease (e.g., cancer). In some certain embodiments, a disease associated with CD33-expression is a leukemia. A leukemia can include, but is not limited to, at least one of: acute leukemia, acute lymphoblastic leukemia (ALL) (including B-cell ALL and T-cell ALL), acute myeloid leukemia (AML), chromic myelocytic leukemia (CML), chronic lymphocytic leukemia (CLL), hairy cell leukemia. In some certain embodiments, provided compositions and methods can be used to treat and/or diagnose acute lymphoblastic leukemia (ALL). In some certain embodiments, provided compositions and methods can be used to treat and/or diagnose extramedullary (EM) manifestations of leukemia.

Also provided, among other things, are technologies for treating, preventing and/or diagnosing a medical condition in a subject, wherein the medical condition characterized by CD33 expression. In some embodiments, a technology for treating, preventing or diagnosing a medical condition characterized by CD33 expression, comprises administering a therapeutically effective amount of a multispecific antibody agent (e.g., a bispecific antibody agent, such as a CD33-BsAb). In some embodiments, a technology for treating, preventing or diagnosing a medical condition characterized by CD33 expression, comprises administering a composition that delivers a therapeutically effective amount of a multispecific antibody agent (e.g., a bispecific antibody agent, such as a CD33-BsAb).

Also provided, among other things, are technologies for treating, preventing or diagnosing cancer in a subject in need thereof, comprising administering a multispecific antibody agent (e.g., a bispecific antibody agent, such as a CD33-BsAb) of the present disclosure. In some embodiments, a cancer is selected from: acute myeloid leukemia, bi-phenotypic leukemia, myelodysplastic syndromes, chronic myelomonocytic leukemia, myeloid blast crisis of chronic myeloid leukemia, and acute lymphoblastic leukemias. In some embodiments, a technology for treating, preventing or diagnosing cancer further comprises administering a preparation of T-cells. In some embodiments, T-cells of a preparation are activated. In some embodiments, T-cells of a preparation are armed with a multispecific antibody agent (e.g., a bispecific antibody agent, such as a CD33-BsAb) of the present disclosure.

Also provided, among other things, are technologies for characterizing multispecific antibody agents (e.g., bispecific antibody agents, such as CD33-BsAb) and/or compositions comprising said multispecific antibody agents. In some embodiments, multispecific antibody agents (e.g., bispecific antibody agents, such as CD33-BsAb) and/or compositions comprising said multispecific antibody agents are characterized by binding to AML cells (e.g., HL60). In some embodiments, multispecific antibody agents (e.g., bispecific antibody agents, such as CD33-BsAb) and/or compositions comprising said multispecific antibody agents are characterized by in vivo retention (e.g., an in vivo serum half life of at least 6 hours, 12 hours, 18 hours, 24 hours, 36 hours, 48 hours, 60 hours, 72 hours, or more). In some embodiments, multispecific antibody agents (e.g., bispecific antibody agents, such as CD33-BsAb) and/or compositions comprising said multispecific antibody agents are characterized by ELISA, immunohistochemistry, Biacore binding assays, mass spectrometry, isoelectric focusing (IEF) chromatography, western blot, etc.

BRIEF DESCRIPTION OF THE DRAWING

The Drawing included herein, which is comprised of the following Figures, is for illustration purposes only not for limitation.

FIG. 8A depicts tumor growth as monitored by bioluminescence imaging. FIG. 8B provides a graphical representation of results of bioluminescent imaging analysis (expressed as total flux in p/s).

FIG. 12A—Female NSG mice were implanted subcutaneously with 3 million MOLM13 AML cells. Peripheral blood mononuclear cells (PBMC) (10-30 million/dose) were injected once weekly for four weeks starting at seven days after leukemia injection. Exemplary CD33-CD3 IgG-scFv (BsAb) (50 μg/dose for the first 3 weeks and 150 μg/dose for the rest) were injected one day before and one day after each PBMC administration. No IL2 was given to the mice. FIG. 12B and FIG. 12C—Female NSG mice were implanted subcutaneously with 2 million THP1 or 1 million HL60 AML cells. Peripheral blood mononuclear cells (PBMC) (10 million/dose) were injected once weekly for four weeks starting at seven days after leukemia injection. Exemplary CD33-CD3 IgG-scFv (BsAb) (100 μg/dose) were injected one day before and one day after each PBMC administration. No IL2 was administered to the mice.

CERTAIN DEFINITIONS

Figure 1A:
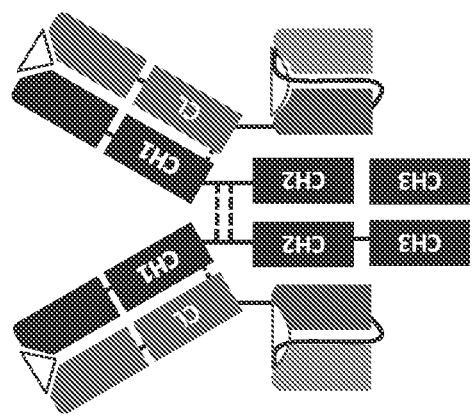
FIG. 1A depicts a schematic of an IgG-scFv bispecific antibody agent format.

In the description that follows, a number of terms used in recombinant DNA and immunology are extensively utilized. In order to provide a clearer and consistent understanding of the specification and claims, including the scope to be given such terms, the following definitions are provided.

Administration: As used herein, the term "administration" typically refers to the administration of a composition to a subject or system to achieve delivery of an agent that is, or is included in, the composition. Those of ordinary skill in the art will be aware of a variety of routes that may, in appropriate circumstances, be utilized for administration to a subject, for example a human. For example, in some embodiments, administration may be ocular, oral, parenteral, topical, etc. In some embodiments, administration may be bronchial (e.g., by bronchial instillation), buccal, dermal (which may be or comprise, for example, one or more of topical to the dermis, intradermal, interdermal, transdermal, etc), enteral, intra-arterial, intradermal, intragastric, intramedullary, intramuscular, intranasal, intraperitoneal, intrathecal, intravenous, intraventricular, within a specific organ (e. g. intrahepatic), mucosal, nasal, oral, rectal, subcutaneous, sublingual, topical, tracheal (e.g., by intratracheal instillation), vaginal, vitreal, etc. In some embodiments, administration may involve only a single dose. In some embodiments, administration may involve application of a fixed number of doses. In some embodiments, administration may involve dosing that is intermittent (e.g., a plurality of doses separated in time) and/or periodic (e.g., individual doses separated by a common period of time) dosing. In some embodiments, administration may involve continuous dosing (e.g., perfusion) for at least a selected period of time.

Affinity: As is known in the art, "affinity" is a measure of the tightness with a particular ligand (e.g., an epitope) binds to its partner (e.g., an antibody). Affinities can be measured in different ways. In some embodiments, affinity is measured by a quantitative assay. In some such embodiments, binding partner concentration may be fixed to be in excess of ligand concentration so as to mimic physiological conditions. Alternatively or additionally, in some embodiments, binding partner concentration and/or ligand concentration may be varied. In some such embodiments, affinity may be compared to a reference under comparable conditions (e.g., concentrations).

Amino acid: As used herein, term "amino acid," in its broadest sense, as used herein, refers to any compound and/or substance that can be incorporated into a polypeptide chain, e.g., through formation of one or more peptide bonds. In some embodiments, an amino acid has the general structure $H_2N-C(H)(R)-COOH$. In some embodiments, an amino acid is a naturally-occurring amino acid. In some embodiments, an amino acid is a non-natural amino acid; in some embodiments, an amino acid is a D-amino acid; in some embodiments, an amino acid is an L-amino acid. "Standard amino acid" refers to any of the twenty standard L-amino acids commonly found in naturally occurring peptides. "Nonstandard amino acid" refers to any amino acid, other than the standard amino acids, regardless of whether it is prepared synthetically or obtained from a natural source. In some embodiments, an amino acid, including a carboxy- and/or amino-terminal amino acid in a polypeptide, can contain a structural modification as compared with the general structure above. For example, in some embodiments, an amino acid may be modified by methylation, amidation, acetylation, pegylation, glycosylation, phosphorylation, and/or substitution (e.g., of the amino group, the carboxylic acid group, one or more protons, and/or the hydroxyl group) as compared with the general structure. In some embodiments, such modification may, for example, alter the circulating half-life of a polypeptide containing the modified amino acid as compared with one containing an otherwise identical unmodified amino acid. In some embodiments, such modification does not significantly alter a relevant activity of a polypeptide containing the modified amino acid, as compared with one containing an otherwise identical unmodified amino acid. As will be clear from context, in some embodiments, the term "amino acid" may be used to refer to a free amino acid; in some embodiments it may be used to refer to an amino acid residue within a polypeptide.

Animal: As used herein, the term "animal" refers to any member of the animal kingdom. In some embodiments, "animal" refers to humans, of either sex and at any stage of development. In some embodiments, "animal" refers to non-human animals, at any stage of development. In certain embodiments, the non-human animal is a mammal (e.g., a rodent, a mouse, a rat, a rabbit, a monkey, a dog, a cat, a sheep, cattle, a primate, and/or a pig). In some embodiments, animals include, but are not limited to, mammals, birds, reptiles, amphibians, fish, insects, and/or worms. In certain embodiments, the animal is susceptible to infection by DV. In some embodiments, an animal may be a transgenic animal, genetically engineered animal, and/or a clone.

Antibody: As used herein, the term "antibody" refers to a polypeptide that includes canonical immunoglobulin sequence elements sufficient to confer specific binding to a particular target antigen. As is known in the art, intact antibodies as produced in nature are approximately 150 kD tetrameric agents comprised of two identical heavy chain polypeptides (about 50 kD each) and two identical light chain polypeptides (about 25 kD each) that associate with each other into what is commonly referred to as a "Y-shaped" structure. Each heavy chain is comprised of at least four domains (each about 110 amino acids long)—an amino-terminal variable (VH) domain (located at the tips of the Y structure), followed by three constant domains: CH1, CH2, and the carboxy-terminal CH3 (located at the base of the Y's stem). A short region, known as the "switch", connects the heavy chain variable and constant regions. The "hinge" connects CH2 and CH3 domains to the rest of the antibody. Two disulfide bonds in this hinge region connect the two heavy chain polypeptides to one another in an intact antibody. Each light chain is comprised of two domains—an amino-terminal variable (VL) domain, followed by a carboxy-terminal constant (CL) domain, separated from one another by another "switch". Intact antibody tetramers are comprised of two heavy chain-light chain dimers in which the heavy and light chains are linked to one another by a single disulfide bond; two other disulfide bonds connect the heavy chain hinge regions to one another, so that the dimers are connected to one another and the tetramer is formed. Naturally-produced antibodies are also glycosylated, typically on the CH2 domain. Each domain in a natural antibody has a structure characterized by an "immunoglobulin fold" formed from two beta sheets (e.g., 3-, 4-, or 5-stranded sheets) packed against each other in a compressed antiparallel beta barrel. Each variable domain contains three hypervariable loops known as "complement determining regions" (CDR1, CDR2, and CDR3) and four somewhat invariant "framework" regions (FR1, FR2, FR3, and FR4). When natural antibodies fold, the FR regions form the beta sheets that provide the structural framework for the domains, and the CDR loop regions from both the heavy and light chains are brought together in three-dimensional space so that they create a single hypervariable antigen binding site located at the tip of the Y structure. The Fc region of naturally-occurring antibodies binds to elements of the complement system, and also to receptors on effector cells, including for example effector cells that mediate cytotoxicity. As is known in the art, affinity and/or other binding attributes of Fc regions for Fc receptors can be modulated through glycosylation or other modification. In some embodiments, antibodies produced and/or utilized in accordance with the present disclosure include glycosylated Fc domains, including Fc domains with modified or engineered such glycosylation. For purposes of the present disclosure, in certain embodiments, any polypeptide or complex of polypeptides that includes sufficient immunoglobulin domain sequences as found in natural antibodies can be referred to and/or used as an "antibody", whether such polypeptide is naturally produced (e.g., generated by an organism reacting to an antigen), or produced by recombinant engineering, chemical synthesis, or other artificial system or methodology. In some embodiments, an antibody is polyclonal; in some embodiments, an antibody is monoclonal. In some embodiments, an antibody has constant region sequences that are characteristic of mouse, rabbit, primate, or human antibodies. The term "antibody" also includes bispecific and chimeric antibodies, and other available formats. In some embodiments, an antibody, as described herein, is or comprises to a full-length immunoglobulin molecule (e.g., an IgG antibody) or an immunologically active (i.e., specifically binding) portion of an immunoglobulin molecule, like an antibody fragment. An antibody fragment is a portion of an antibody such as, for example, F(ab')2, F(ab)2, Fab', Fab, Fv, sFv and the like. In some embodiments, an antibody is in an IgG-scFv format. Regardless of structure, an antibody fragment binds with the same antigen(s) that is recognized by the intact antibody(ies). For example, an M195 monoclonal antibody fragment binds with an epitope recognized by M195. The term "antibody fragment" also includes any synthetic or genetically engineered protein that includes antigen-binding structures of and acts like an antibody by binding to a specific antigen to form a complex. For example, antibody fragments include isolated fragments consisting of the variable regions, such as the "Fv" fragments consisting of the variable regions of the heavy or light chains, recombinant single chain polypeptide molecules in which light and heavy variable regions are connected by a peptide linker ("scFv proteins"), and minimal recognition units consisting of the amino acid residues that are or mimic the hypervariable region. For example, in some embodiments, an antibody fragment comprises one or more, and in some embodiments all, of the complement determining regions (CDRs) found in a heavy or light chain of the parent antibody. In some embodiments, an antibody may lack a covalent modification (e.g., attachment of a glycan) that it would have if produced naturally. In some embodiments, an antibody may contain a covalent modification (e.g., attachment of a glycan, a payload [e.g., a detectable moiety, a therapeutic moiety, a catalytic moiety, etc], or other pendant group [e.g., poly-ethylene glycol, etc.]

Antibody agent: As used herein, the term "antibody agent" refers to an agent that specifically binds to a particular antigen. In some embodiments, the term encompasses any polypeptide or polypeptide complex that includes immunoglobulin structural elements sufficient to confer specific binding. Exemplary antibody agents include, but are not limited to monoclonal antibodies or polyclonal antibodies. In some embodiments, an antibody agent may include one or more constant region sequences that are characteristic of mouse, rabbit, primate, or human antibodies. In some embodiments, an antibody agent may include one or more sequence elements are humanized, primatized, chimeric, etc, as is known in the art. In many embodiments, the term "antibody agent" is used to refer to one or more of the art-known or developed constructs or formats for utilizing antibody structural and functional features in alternative presentation. For example, embodiments, an antibody agent utilized in accordance with the present disclosure is in a format selected from, but not limited to, intact IgA, IgG, IgE or IgM antibodies; bi- or multi-specific antibodies (e.g., Zybodies®, etc); antibody fragments such as Fab fragments, Fab' fragments, F(ab')2 fragments, Fd' fragments, Fd fragments, and isolated CDRs or sets thereof; single chain Fvs; polypeptide-Fc fusions; single domain antibodies (e.g., shark single domain antibodies such as IgNAR or fragments thereof); cameloid antibodies; masked antibodies (e.g., Probodies®); Small Modular ImmunoPharmaceuticals ("SMIPs™"); single chain or Tandem diabodies (TandAb®); Anticalins®; Nanobodies® minibodies; BiTE®s; ankyrin repeat proteins or DARPINs®; Avimers®; DARTs; TCR-like antibodies; Adnectins®; Affilins®; Transbodies®; Affibodies®; TrimerX®; MicroProteins; Fynomers®, Centyrins®; and KALBITOR®s. In some embodiments, an antibody may lack a covalent modification (e.g., attachment of a glycan) that it would have if produced naturally. In some embodiments, an antibody may contain a covalent modification (e.g., attachment of a glycan, a payload [e.g., a detectable moiety, a therapeutic moiety, a catalytic moiety, etc], or other pendant group [e.g., poly-ethylene glycol, etc.]. In many embodiments, an antibody agent is or comprises a polypeptide whose amino acid sequence includes one or more structural elements recognized by those skilled in the art as a complementarity determining region (CDR); in some embodiments an antibody agent is or comprises a polypeptide whose amino acid sequence includes at least one CDR (e.g., at least one heavy chain CDR and/or at least one light chain CDR) that is substantially identical to one found in a reference antibody.

In some embodiments an included CDR is substantially identical to a reference CDR in that it is either identical in sequence or contains between 1-5 amino acid substitutions as compared with the reference CDR. In some embodiments an included CDR is substantially identical to a reference CDR in that it shows at least 85%, 86%, 87%, 88%, 89%, 90%, 91%, 92%, 93%, 94%, 95%, 96%, 97%, 98%, 99%, or 100% sequence identity with the reference CDR. In some embodiments an included CDR is substantially identical to a reference CDR in that it shows at least 96%, 96%, 97%, 98%, 99%, or 100% sequence identity with the reference CDR. In some embodiments an included CDR is substantially identical to a reference CDR in that at least one amino acid within the included CDR is deleted, added, or substituted as compared with the reference CDR but the included CDR has an amino acid sequence that is otherwise identical with that of the reference CDR. In some embodiments an included CDR is substantially identical to a reference CDR in that 1-5 amino acids within the included CDR are deleted, added, or substituted as compared with the reference CDR but the included CDR has an amino acid sequence that is otherwise identical to the reference CDR. In some embodiments an included CDR is substantially identical to a reference CDR in that at least one amino acid within the included CDR is substituted as compared with the reference CDR but the included CDR has an amino acid sequence that is otherwise identical with that of the reference CDR. In some embodiments an included CDR is substantially identical to a reference CDR in that 1-5 amino acids within the included CDR are deleted, added, or substituted as compared with the reference CDR but the included CDR has an amino acid sequence that is otherwise identical to the reference CDR. In some embodiments, an antibody agent is or comprises a polypeptide whose amino acid sequence includes structural elements recognized by those skilled in the art as an immunoglobulin variable domain. In some embodiments, an antibody agent is a polypeptide protein having a binding domain which is homologous or largely homologous to an immunoglobulin-binding domain.

Cancer: The terms "cancer", "malignancy", "neoplasm", "tumor", and "carcinoma", are used herein to refer to cells that exhibit relatively abnormal, uncontrolled, and/or autonomous growth, so that they exhibit an aberrant growth phenotype characterized by a significant loss of control of cell proliferation. In some embodiments, a tumor may be or comprise cells that are precancerous (e.g., benign), malignant, pre-metastatic, metastatic, and/or non-metastatic. The present disclosure specifically identifies certain cancers to which its teachings may be particularly relevant. In some embodiments, a relevant cancer may be characterized by a solid tumor. In some embodiments, a relevant cancer may be characterized by a hematologic tumor. In general, examples of different types of cancers known in the art include, for example, hematopoietic cancers including leukemias, lymphomas (Hodgkin's and non-Hodgkin's), myelomas and myeloproliferative disorders; sarcomas, melanomas, adenomas, carcinomas of solid tissue, squamous cell carcinomas of the mouth, throat, larynx, and lung, liver cancer, genitourinary cancers such as prostate, cervical, bladder, uterine, and endometrial cancer and renal cell carcinomas, bone cancer, pancreatic cancer, skin cancer, cutaneous or intraocular melanoma, cancer of the endocrine system, cancer of the thyroid gland, cancer of the parathyroid gland, head and neck cancers, breast cancer, gastro-intestinal cancers and nervous system cancers, benign lesions such as papillomas, and the like. In some embodiments, a relavent hematological cancer includes acute myeloid leukemia, bi-phenotypic leukemia, myelodysplastic syndromes, chronic myelomonocytic leukemia, myeloid blast crisis of chronic myeloid leukemia, and acute lymphoblastic leukemias.

Chelator: A chelator such as DTPA, DOTA, Benzyl-DOTA, TETA, or NOTA may be utilized in any of a variety of circumstances, including in conjugates. The same chelators, when complexed with non-radioactive metals, such as Mn, Fe and Gd can be used for MRI, when used along with the bsAbs of the present disclosure. Macrocyclic chelators such as NOTA (1,4,7-triaza-cyclononane-N,N',N"-triacetic acid), DOTA, Benzyl-DOTA, and TETA (p-bromoacetamido-benzyl-tetraethylaminetetraacetic acid) are of use with a variety of metals and radiometals, most particularly with radionuclides of Ga, Y and Cu, respectively.

Chemotherapeutic Agent: The term "chemotherapeutic agent," has used herein has its art-understood meaning referring to one or more pro-apoptotic, cytostatic and/or cytotoxic agents, for example specifically including agents utilized and/or recommended for use in treating one or more diseases, disorders or conditions associated with undesirable cell proliferation. In many embodiments, chemotherapeutic agents are useful in the treatment of cancer. In some embodiments, a chemotherapeutic agent may be or comprise one or more alkylating agents, one or more anthracyclines, one or more cytoskeletal disruptors (e.g. microtubule targeting agents such as taxanes, maytansine and analogs thereof, of), one or more epothilones, one or more histone deacetylase inhibitors HDACs), one or more topoisomerase inhibitors (e.g., inhibitors of topoisomerase I and/or topoisomerase II), one or more kinase inhibitors, one or more nucleotide analogs or nucleotide precursor analogs, one or more peptide antibiotics, one or more platinum-based agents, one or more retinoids, one or more vinca alkaloids, and/or one or more analogs of one or more of the following (i.e., that share a relevant anti-proliferative activity). In some particular embodiments, a chemotherapeutic agent may be or comprise one or more of Actinomycin, All-trans retinoic acid, an Auiristatin, Azacitidine, Azathioprine, Bleomycin, Bortezomib, Carboplatin, Capecitabine, Cisplatin, Chlorambucil, Cyclophosphamide, Curcumin, Cytarabine, Daunorubicin, Docetaxel, Doxifluridine, Doxorubicin, Epirubicin, Epothilone, Etoposide, Fluorouracil, Gemcitabine, Hydroxyurea, Idarubicin, Imatinib, Irinotecan, Maytansine and/or analogs thereof (e.g. DM1) Mechlorethamine, Mercaptopurine, Methotrexate, Mitoxantrone, a Maytansinoid, Oxaliplatin, Paclitaxel, Pemetrexed, Teniposide, Tioguanine, Topotecan, Valrubicin, Vinblastine, Vincristine, Vindesine, Vinorelbine, and combinations thereof. In some embodiments, a chemotherapeutic agent may be utilized in the context of an antibody-drug conjugate. In some embodiments, a chemotherapeutic agent is one found in an antibody-drug conjugate selected from the group consisting of: hLL1-doxorubicin, hRS7-SN-38, hMN-14-SN-38, hLL2-SN-38, hA20-SN-38, hPAM4-SN-38, hLL1-SN-38, hRS7-Pro-2-P-Dox, hMN-14-Pro-2-P-Dox, hLL2-Pro-2-P-Dox, hA20-Pro-2-P-Dox, hPAM4-Pro-2-P-Dox, hLL1-Pro-2-P-Dox, P4/D10-doxorubicin, gemtuzumab ozogamicin, brentuximab vedotin, trastuzumab emtansine, inotuzumab ozogamicin, glembatumomab vedotin, SAR3419, SAR566658, BIIB015, BT062, SGN-75, SGN-CD19A, AMG-172, AMG-595, BAY-94-9343, ASG-SME, ASG-22ME, ASG-16M8F, MDX-1203, MLN-0264, anti-PSMA ADC, RG-7450, RG-7458, RG-7593, RG-7596, RG-7598, RG-7599, RG-7600, RG-7636, ABT-414, IMGN-853, IMGN-529, vorsetuzumab mafodotin, and lorvotuzumab mertansine. In some embodiments, a chemotherapeutic agent may be one described as utilized in an antibody-drug conjugate as described or discussed in one or more of Govindan et al, The Scientific World JOURNAL 10:2070-2089, 2010. In some embodiments, a chemotherapeutic agent may be or comprise one or more of farnesyl-thiosalicylic acid (FTS), 4-(4-Chloro-2-methylphenoxy)-N-hydroxybutanamide (CMH), estradiol (E2), tetramethoxystilbene (TMS), δ-tocatrienol, salinomycin, or curcumin.

Chimeric antibody: as used herein, refers to an antibody whose amino acid sequence includes $V_H$ and $V_L$ region sequences that are found in a first species and constant region sequences that are found in a second species, different from the first species. In many embodiments, a chimeric antibody has murine $V_H$ and $V_L$ regions linked to human constant regions. In some embodiments, an antibody with human $V_H$ and $V_L$ regions linked to non-human constant regions (e.g., a mouse constant region) is referred to as a "reverse chimeric antibody".

Comparable: As used herein, the term "comparable" refers to two or more agents, entities, situations, sets of conditions, etc., that may not be identical to one another but that are sufficiently similar to permit comparison therebetween so that one skilled in the art will appreciate that conclusions may reasonably be drawn based on differences or similarities observed. In some embodiments, comparable sets of conditions, circumstances, individuals, or populations are characterized by a plurality of substantially identical features and one or a small number of varied features. Those of ordinary skill in the art will understand, in context, what degree of identity is required in any given circumstance for two or more such agents, entities, situations, sets of conditions, etc. to be considered comparable. For example, those of ordinary skill in the art will appreciate that sets of circumstances, individuals, or populations are comparable to one another when characterized by a sufficient number and type of substantially identical features to warrant a reasonable conclusion that differences in results obtained or phenomena observed under or with different sets of circumstances, individuals, or populations are caused by or indicative of the variation in those features that are varied.

Conjugate: In some embodiments, provided antibody agents are utilized in conjugates. In some particular embodiments, A chelator such as DTPA, DOTA, Benzyl-DOTA, TETA, or NOTA or a suitable peptide, to which a detectable label, such as a fluorescent molecule, or cytotoxic agent, such as a heavy metal or radionuclide, can be conjugated. For example, a therapeutically useful immunoconjugate can be obtained by conjugating a photoactive agent or dye to an antibody fusion polypeptide. Fluorescent compositions, such as fluorochrome, and other chromogens, or dyes, such as porphyrins sensitive to visible light, have been used to detect and to treat lesions by directing the suitable light to the lesion. In therapy, this has been termed photoradiation, phototherapy, or photodynamic therapy (Joni et al. (eds.), PHOTODYNAMIC THERAPY OF TUMORS AND OTHER DISEASES (Libreria Progetto 1985); van den Bergh, Chem. Britain 22:430 (1986)). Moreover, monoclonal antibodies have been coupled with photoactivated dyes for achieving phototherapy. Mew et al., J. Immunol. 130: 1473 (1983); idem., Cancer Res. 45:4380 (1985); Oseroff et al., Proc. Natl. Acad. Sci. USA 83:8744 (1986); idem., Photochem. Photobiol. 46:83 (1987); Hasan et al., Prog. Clin. Biol. Res. 288:471 (1989); Tatsuta et al., Lasers Surg. Med. 9:422 (1989); Pelegrin et al., Cancer 67:2529 (1991). However, these earlier studies did not include use of endoscopic therapy applications, especially with the use of antibody fragments or subfragments. Thus, the present disclosure contemplates the therapeutic use of immunoconjugates comprising photoactive agents or dyes.

Corresponding to: As used herein, the term "corresponding to" may be used to designate the position/identity of a structural element in a compound or composition through comparison with an appropriate reference compound or composition. For example, in some embodiments, a monomeric residue in a polymer (e.g., an amino acid residue in a polypeptide or a nucleic acid residue in a polynucleotide) may be identified as corresponding to a residue in an appropriate reference polymer. For example, those of ordinary skill will appreciate that, for purposes of simplicity, residues in a polypeptide are often designated using a canonical numbering system based on a reference related polypeptide, so that an amino acid "corresponding to" a residue at position 190, for example, need not actually be the $190^{th}$ amino acid in a particular amino acid chain but rather corresponds to the residue found at 190 in the reference polypeptide; those of ordinary skill in the art readily appreciate how to identify "corresponding" amino acids. For example, those skilled in the art will be aware of various sequence alignment strategies, including software programs such as, for example, BLAST, CS-BLAST, CUSASW++, DIAMOND, FASTA, GGSEARCH/GLSEARCH, Genoogle, HMMER, HHpred/HHsearch, IDF, Infernal, KLAST, USEARCH, parasail, PSI-BLAST, PSI-Search, ScalaBLAST, Sequilab, SAM, SSEARCH, SWAPHI, SWAPHI-LS, SWIMM, or SWIPE that can be utilized, for example, to identify "corresponding" residues in polypeptides and/or nucleic acids in accordance with the present disclosure.

Detectable entity: The term "detectable entity" as used herein refers to any element, molecule, functional group, compound, fragment or moiety that is detectable. In some embodiments, a detectable entity is provided or utilized alone. In some embodiments, a detectable entity is provided and/or utilized in association with (e.g., joined to) another agent. Examples of detectable entities include, but are not limited to: various ligands, radionuclides (e.g., $^{3}H$, $^{14}C$, $^{18}F$, $^{19}F$, $^{32}P$, $^{35}S$, $^{135}I$, $^{125}I$, $^{123}I$, $^{64}Cu$, $^{187}Re$, $^{111}In$, $^{90}Y$, $^{99m}Tc$, $^{177}Lu$, $^{89}Zr$ etc.), fluorescent dyes (for specific exemplary fluorescent dyes, see below), chemiluminescent agents (such as, for example, acridinum esters, stabilized dioxetanes, and the like), bioluminescent agents, spectrally resolvable inorganic fluorescent semiconductors nanocrystals (i.e., quantum dots), metal nanoparticles (e.g., gold, silver, copper, platinum, etc.) nanoclusters, paramagnetic metal ions, enzymes (for specific examples of enzymes, see below), colorimetric labels (such as, for example, dyes, colloidal gold, and the like), biotin, dioxigenin, haptens, and proteins for which antisera or monoclonal antibodies are available.

Diagnostic agent: A diagnostic agent is or comprises an entity that is detectable when administered. In some embodiments, a diagnostic agent is administered conjugated to an antibody moiety, i.e., antibody or antibody fragment, or subfragment, as described herein, and is useful in diagnosing or detecting a disease by locating the cells containing the antigen.

Dosage form: Those skilled in the art will appreciate that the term "dosage form" may be used to refer to a physically discrete unit of an active agent (e.g., a therapeutic or diagnostic agent) for administration to a subject. Typically, each such unit contains a predetermined quantity of active agent. In some embodiments, such quantity is a unit dosage amount (or a whole fraction thereof) appropriate for administration in accordance with a dosing regimen that has been determined to correlate with a desired or beneficial outcome when administered to a relevant population (i.e., with a therapeutic dosing regimen). Those of ordinary skill in the art appreciate that the total amount of a therapeutic composition or agent administered to a particular subject is determined by one or more attending physicians and may involve administration of multiple dosage forms.

Dosing regimen: Those skilled in the art will appreciate that the term "dosing regimen" may be used to refer to a set of unit doses (typically more than one) that are administered individually to a subject, typically separated by periods of time. In some embodiments, a given therapeutic agent has a recommended dosing regimen, which may involve one or more doses. In some embodiments, a dosing regimen comprises a plurality of doses each of which is separated in time from other doses. In some embodiments, individual doses are separated from one another by a time period of the same length; in some embodiments, a dosing regimen comprises a plurality of doses and at least two different time periods separating individual doses. In some embodiments, all doses within a dosing regimen are of the same unit dose amount. In some embodiments, different doses within a dosing regimen are of different amounts. In some embodiments, a dosing regimen comprises a first dose in a first dose amount, followed by one or more additional doses in a second dose amount different from the first dose amount. In some embodiments, a dosing regimen comprises a first dose in a first dose amount, followed by one or more additional doses in a second dose amount same as the first dose amount. In some embodiments, a dosing regimen is correlated with a desired or beneficial outcome when administered across a relevant population (i.e., is a therapeutic dosing regimen).

Effector function: as used herein refers a biochemical event that results from the interaction of an antibody Fc region with an Fc receptor or ligand. Effector functions include but are not limited to antibody-dependent cell-mediated cytotoxicity (ADCC), antibody-dependent cell-mediated phagocytosis (ADCP), and complement-mediated cytotoxicity (CMC). In some embodiments, an effector function is one that operates after the binding of an antigen, one that operates independent of antigen binding, or both.

Effector Cell: as used herein refers to a cell of the immune system that expresses one or more Fc receptors and mediates one or more effector functions. In some embodiments, effector cells may include, but may not be limited to, one or more of monocytes, macrophages, neutrophils, dendritic cells, eosinophils, mast cells, platelets, large granular lymphocytes, Langerhans' cells, natural killer (NK) cells, T-lymphocytes, B-lymphocytes and may be from any organism including but not limited to humans, mice, rats, rabbits, and monkeys.

Epitope: as used herein, includes any moiety that is specifically recognized by an immunoglobulin (e.g., antibody or receptor) binding component. In some embodiments, an epitope is comprised of a plurality of chemical atoms or groups on an antigen. In some embodiments, such chemical atoms or groups are surface-exposed when the antigen adopts a relevant three-dimensional conformation. In some embodiments, such chemical atoms or groups are physically near to each other in space when the antigen adopts such a conformation. In some embodiments, at least some such chemical atoms are groups are physically separated from one another when the antigen adopts an alternative conformation (e.g., is linearized).

Fc Ligand: as used herein refers to a molecule, preferably a polypeptide, from any organism that binds to the Fc region of an antibody to form an Fc-ligand complex. Fc ligands include but are not limited to FcγRIIA (CD32A), FcγRIIB (CD32B), FcγRIIIA (CD16A), FcγRIIIB (CD16B), FcγRI (CD64), FcεRII (CD23), FcRn, Clq, C3, staphylococcal protein A, streptococcal protein G, and viral FcγR. Fc ligands may include undiscovered molecules that bind Fc.

Homology: As used herein, the term "homology" refers to the overall relatedness between polymeric molecules, e.g., between polypeptide molecules. In some embodiments, polymeric molecules such as antibodies are considered to be "homologous" to one another if their sequences are at least 80%, 85%, 90%, 95%, 96%, 97%, 98%, or 99% identical. In some embodiments, polymeric molecules are considered to be "homologous" to one another if their sequences are at least 80%, 85%, 90%, 95%, 96%, 97%, 98%, or 99% similar.

Host cell: as used herein, refers to a cell into which exogenous DNA (recombinant or otherwise) has been introduced. Persons of skill upon reading this disclosure will understand that such terms refer not only to the particular subject cell, but also to the progeny of such a cell. Because certain modifications may occur in succeeding generations due to either mutation or environmental influences, such progeny may not, in fact, be identical to the parent cell, but are still included within the scope of the term "host cell" as used herein. In some embodiments, host cells include prokaryotic and eukaryotic cells selected from any of the Kingdoms of life that are suitable for expressing an exogenous DNA (e.g., a recombinant nucleic acid sequence). Exemplary cells include those of prokaryotes and eukaryotes (single-cell or multiple-cell), bacterial cells (e.g., strains of *E. coli, Bacillus* spp., *Streptomyces* spp., etc.), mycobacteria cells, fungal cells, yeast cells (e.g., *S. cerevisiae, S. pombe, P. pastoris, P. methanolica*, etc.), plant cells, insect cells (e.g., SF-9, SF-21, baculovirus-infected insect cells, *Trichoplusia ni*, etc.), non-human animal cells, human cells, or cell fusions such as, for example, hybridomas or quadromas. In some embodiments, the cell is a human, monkey, ape, hamster, rat, or mouse cell. In some embodiments, the cell is eukaryotic and is selected from the following cells: CHO (e.g., CHO Kl, DXB-1 1 CHO, Veggie-CHO), COS (e.g., COS-7), retinal cell, Vero, CV1, kidney (e.g., HEK293, 293 EBNA, MSR 293, MDCK, HaK, BHK), HeLa, HepG2, WI38, MRC 5, Colo205, HB 8065, HL-60, (e.g., BHK21), Jurkat, Daudi, A431 (epidermal), CV-1, U937, 3T3, L cell, C127 cell, SP2/0, NS-0, MMT 060562, Sertoli cell, BRL 3 A cell, HT1080 cell, myeloma cell, tumor cell, and a cell line derived from an aforementioned cell. In some embodiments, the cell comprises one or more viral genes.

Human: as used herein, is intended to include humans at all stages of development. In some embodiments a human is an embryo, a fetus, an infant, a child, a teenager, an adult, or a senior citizen.

Human antibody: as used herein, is intended to include antibodies having variable and constant regions generated (or assembled) from human immunoglobulin sequences. In some embodiments, antibodies (or antibody components) may be considered to be "human" even though their amino acid sequences include residues or elements not encoded by human germline immunoglobulin sequences (e.g., include sequence variations, for example that may (originally) have been introduced by random or site-specific mutagenesis in vitro or by somatic mutation in vivo), for example in one or more CDRs and in particular CDR3.

Humanized: A "humanized" antibody is a recombinant protein in which the CDRs from an antibody from one species; e.g., a rodent antibody, are transferred from the heavy and light variable chains of the rodent antibody into human heavy and light variable domains. The constant domain of the antibody molecule is derived from those of a human antibody.

Identity: As used herein, the term "identity" refers to the overall relatedness between polymeric molecules, e.g., between nucleic acid molecules (e.g., DNA molecules and/or RNA molecules) and/or between polypeptide molecules. In some embodiments, polymeric molecules are considered to be "substantially identical" to one another if their sequences are at least 25%, 30%, 35%, 40%, 45%, 50%, 55%, 60%, 65%, 70%, 75%, 80%, 85%, 90%, 95%, or 99% identical. Calculation of the percent identity of two nucleic acid or polypeptide sequences, for example, can be performed by aligning the two sequences for optimal comparison purposes (e.g., gaps can be introduced in one or both of a first and a second sequences for optimal alignment and non-identical sequences can be disregarded for comparison purposes). In certain embodiments, the length of a sequence aligned for comparison purposes is at least 30%, at least 40%, at least 50%, at least 60%, at least 70%, at least 80%, at least 90%, at least 95%, or substantially 100% of the length of a reference sequence. The nucleotides at corresponding positions are then compared. When a position in the first sequence is occupied by the same residue (e.g., nucleotide or amino acid) as the corresponding position in the second sequence, then the molecules are identical at that position. The percent identity between the two sequences is a function of the number of identical positions shared by the sequences, taking into account the number of gaps, and the length of each gap, which needs to be introduced for optimal alignment of the two sequences. The comparison of sequences and determination of percent identity between two sequences can be accomplished using a mathematical algorithm. For example, the percent identity between two nucleotide sequences can be determined using the algorithm of Meyers and Miller (CABIOS, 1989, 4: 11-17), which has been incorporated into the ALIGN program (version 2.0). In some exemplary embodiments, nucleic acid sequence comparisons made with the ALIGN program use a PAM120 weight residue table, a gap length penalty of 12 and a gap penalty of 4. The percent identity between two nucleotide sequences can, alternatively, be determined using the GAP program in the GCG software package using an NWSgapdna.CMP matrix.

Immunoconjugate: An "immunoconjugate" is a conjugate (i.e., a covalent linkage) of an antibody component with a payload (e.g., a therapeutic or diagnostic agent).

Immunomodulator: An "immunomodulator" is an agent that when present, typically stimulates immune cells to proliferate or become activated in an immune response cascade, such as macrophages, B-cells, and/or T cells. An example of an immunomodulator as described herein is a cytokine. As the skilled artisan will understand, certain interleukins and interferons are examples of cytokines that stimulate T cell or other immune cell proliferation.

In vitro: The term "in vitro" as used herein refers to events that occur in an artificial environment, e.g., in a test tube or reaction vessel, in cell culture, etc., rather than within a multi-cellular organism.

In vivo: as used herein refers to events that occur within a multi-cellular organism, such as a human and a non-human animal. In the context of cell-based systems, the term may be used to refer to events that occur within a living cell (as opposed to, for example, in vitro systems).

Isolated: as used herein, refers to a substance and/or entity that has been (1) separated from at least some of the components with which it was associated when initially produced (whether in nature and/or in an experimental setting), and/or (2) designed, produced, prepared, and/or manufactured by the hand of man. Isolated substances and/or entities may be separated from about 10%, about 20%, about 30%, about 40%, about 50%, about 60%, about 70%, about 80%, about 90%, about 91%, about 92%, about 93%, about 94%, about 95%, about 96%, about 97%, about 98%, about 99%, or more than about 99% of the other components with which they were initially associated. In some embodiments, isolated agents are about 80%, about 85%, about 90%, about 91%, about 92%, about 93%, about 94%, about 95%, about 96%, about 97%, about 98%, about 99%, or more than about 99% pure. As used herein, a substance is "pure" if it is substantially free of other components. In some embodiments, as will be understood by those skilled in the art, a substance may still be considered "isolated" or even "pure", after having been combined with certain other components such as, for example, one or more carriers or excipients (e.g., buffer, solvent, water, etc.); in such embodiments, percent isolation or purity of the substance is calculated without including such carriers or excipients. To give but one example, in some embodiments, a biological polymer such as a polypeptide or polynucleotide that occurs in nature is considered to be "isolated" when, a) by virtue of its origin or source of derivation is not associated with some or all of the components that accompany it in its native state in nature; b) it is substantially free of other polypeptides or nucleic acids of the same species from the species that produces it in nature; c) is expressed by or is otherwise in association with components from a cell or other expression system that is not of the species that produces it in nature. Thus, for instance, in some embodiments, a polypeptide that is chemically synthesized or is synthesized in a cellular system different from that which produces it in nature is considered to be an "isolated" polypeptide. Alternatively or additionally, in some embodiments, a polypeptide that has been subjected to one or more purification techniques may be considered to be an "isolated" polypeptide to the extent that it has been separated from other components a) with which it is associated in nature; and/or b) with which it was associated when initially produced.

Linker: as used herein, is used to refer to that portion of a multi-element agent that connects different elements to one another. For example, those of ordinary skill in the art appreciate that a polypeptide whose structure includes two or more functional or organizational domains often includes a stretch of amino acids between such domains that links them to one another. In some embodiments, a polypeptide comprising a linker element has an overall structure of the general form S1-L-S2, wherein S1 and S2 may be the same or different and represent two domains associated with one another by the linker. In some embodiments, a polypeptide linker is at least 2, 3, 4, 5, 6, 7, 8, 9, 10, 11, 12, 13, 14, 15, 16, 17, 18, 19, 20, 21, 22, 23, 24, 25, 26, 27, 28, 29, 30, 35, 40, 45, 50, 55, 60, 65, 70, 75, 80, 85, 90, 95, 100 or more amino acids in length. In some embodiments, a linker is characterized in that it tends not to adopt a rigid three-dimensional structure, but rather provides flexibility to the polypeptide. A variety of different linker elements that can appropriately be used when engineering polypeptides (e.g., fusion polypeptides) known in the art (see e.g., Holliger, P., et al. (1993) Proc. Natl. Acad. Sci. USA 90:6444-6448; Poljak, R. J., et al. (1994) Structure 2: 1 121-1123).

Multispecific: A "multispecific" antibody is an antibody that can bind simultaneously to at least two targets that are of different structure, e.g., two different antigens, two different epitopes on the same antigen, or a hapten and an antigen or epitope. One specificity would be for, for example, a B-cell, T-cell, myeloid-, plasma-, or mast-cell antigen or epitope. Another specificity could be to a different antigen on the same cell type, such as, for example, CD20, CD19, CD21, CD23, CD46, CD80, HLA-DR, CD74, or CD22 on B-cells. Multispecific, multivalent antibodies are constructs that have more than one binding site, and the binding sites are of different specificity. For example, a bispecific antibody, where one binding site reacts with one epitope of an antigen and the other with another epitope of the same or different antigen.

Mutant: As used herein, the term "mutant" refers to an entity that shows significant structural identity with a reference entity but differs structurally from the reference entity in the presence or level of one or more chemical moieties as compared with the reference entity. In many embodiments, a mutant also differs functionally from its reference entity. In general, whether a particular entity is properly considered to be a "mutant" of a reference entity is based on its degree of structural identity with the reference entity. As will be appreciated by those skilled in the art, any biological or chemical reference entity has certain characteristic structural elements. A mutant, by definition, is a distinct chemical entity that shares one or more such characteristic structural elements. To give but a few examples, a small molecule may have a characteristic core structural element (e.g., a macrocycle core) and/or one or more characteristic pendent moieties so that a mutant of the small molecule is one that shares the core structural element and the characteristic pendent moieties but differs in other pendent moieties and/or in types of bonds present (single vs double, E vs Z, etc.) within the core, a polypeptide may have a characteristic sequence element comprised of a plurality of amino acids having designated positions relative to one another in linear or three-dimensional space and/or contributing to a particular biological function, a nucleic acid may have a characteristic sequence element comprised of a plurality of nucleotide residues having designated positions relative to on another in linear or three-dimensional space. For example, a mutant polypeptide may differ from a reference polypeptide as a result of one or more differences in amino acid sequence and/or one or more differences in chemical moieties (e.g., carbohydrates, lipids, etc.) covalently attached to the polypeptide backbone. In some embodiments, a mutant polypeptide shows an overall sequence identity with a reference polypeptide that is at least 85%, 86%, 87%, 88%, 89%, 90%, 91%, 92%, 93%, 94%, 95%, 96%, 97%, or 99%. Alternatively or additionally, in some embodiments, a mutant polypeptide does not share at least one characteristic sequence element with a reference polypeptide. In some embodiments, the reference polypeptide has one or more biological activities. In some embodiments, a mutant polypeptide shares one or more of the biological activities of the reference polypeptide. In some embodiments, a mutant polypeptide lacks one or more of the biological activities of the reference polypeptide. In some embodiments, a mutant polypeptide shows a reduced level of one or more biological activities as compared with the reference polypeptide.

Patient: As used herein, the term "patient" refers to any organism to which a provided composition is or may be administered, e.g., for experimental, diagnostic, prophylactic, cosmetic, and/or therapeutic purposes. Typical patients include animals (e.g., mammals such as mice, rats, rabbits, non-human primates, and/or humans). In some embodiments, a patient is a human. In some embodiments, a patient is suffering from or susceptible to one or more disorders or conditions. In some embodiments, a patient displays one or more symptoms of a disorder or condition. In some embodiments, a patient has been diagnosed with one or more disorders or conditions. In some embodiments, the disorder or condition is or includes cancer, or presence of one or more tumors. In some embodiments, the patient is receiving or has received certain therapy to diagnose and/or to treat a disease, disorder, or condition.

Pharmaceutically acceptable: As used herein, the term "pharmaceutically acceptable" applied to the carrier, diluent, or excipient used to formulate a composition as disclosed herein means that the carrier, diluent, or excipient must be compatible with the other ingredients of the composition and not deleterious to the recipient thereof.

Pharmaceutically acceptable carrier: As used herein, the term "pharmaceutically acceptable carrier" means a pharmaceutically-acceptable material, composition or vehicle, such as a liquid or solid filler, diluent, excipient, or solvent encapsulating material, involved in carrying or transporting the subject compound from one organ, or portion of the body, to another organ, or portion of the body. Each carrier must be "acceptable" in the sense of being compatible with the other ingredients of the formulation and not injurious to the patient. Some examples of materials which can serve as pharmaceutically-acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; pH buffered solutions; polyesters, polycarbonates and/or polyanhydrides; and other non-toxic compatible substances employed in pharmaceutical formulations.

Polypeptide: As used herein refers to any polymeric chain of amino acids. In some embodiments, a polypeptide has an amino acid sequence that occurs in nature. In some embodiments, a polypeptide has an amino acid sequence that does not occur in nature. In some embodiments, a polypeptide has an amino acid sequence that is engineered in that it is designed and/or produced through action of the hand of man. In some embodiments, a polypeptide may comprise or consist of natural amino acids, non-natural amino acids, or both. In some embodiments, a polypeptide may comprise or consist of only natural amino acids or only non-natural amino acids. In some embodiments, a polypeptide may comprise D-amino acids, L-amino acids, or both. In some embodiments, a polypeptide may comprise only D-amino acids. In some embodiments, a polypeptide may comprise only L-amino acids. In some embodiments, a polypeptide may include one or more pendant groups or other modifications, e.g., modifying or attached to one or more amino acid side chains, at the polypeptide's N-terminus, at the polypeptide's C-terminus, or any combination thereof. In some embodiments, such pendant groups or modifications may be selected from the group consisting of acetylation, amidation, lipidation, methylation, pegylation, etc., including combinations thereof. In some embodiments, a polypeptide may be cyclic, and/or may comprise a cyclic portion. In some embodiments, a polypeptide is not cyclic and/or does not comprise any cyclic portion. In some embodiments, a polypeptide is linear. In some embodiments, a polypeptide may be or comprise a stapled polypeptide. In some embodiments, the term "polypeptide" may be appended to a name of a reference polypeptide, activity, or structure; in such instances it is used herein to refer to polypeptides that share the relevant activity or structure and thus can be considered to be members of the same class or family of polypeptides. For each such class, the present specification provides and/or those skilled in the art will be aware of exemplary polypeptides within the class whose amino acid sequences and/or functions are known; in some embodiments, such exemplary polypeptides are reference polypeptides for the polypeptide class or family. In some embodiments, a member of a polypeptide class or family shows significant sequence homology or identity with, shares a common sequence motif (e.g., a characteristic sequence element) with, and/or shares a common activity (in some embodiments at a comparable level or within a designated range) with a reference polypeptide of the class; in some embodiments with all polypeptides within the class). For example, in some embodiments, a member polypeptide shows an overall degree of sequence homology or identity with a reference polypeptide that is at least about 30-40%, and is often greater than about 50%, 60%, 70%, 80%, 90%, 91%, 92%, 93%, 94%, 95%, 96%, 97%, 98%, 99% or more and/or includes at least one region (e.g., a conserved region that may in some embodiments be or comprise a characteristic sequence element) that shows very high sequence identity, often greater than 90% or even 95%, 96%, 97%, 98%, or 99%. Such a conserved region usually encompasses at least 3-4 and often up to 20 or more amino acids; in some embodiments, a conserved region encompasses at least one stretch of at least 2, 3, 4, 5, 6, 7, 8, 9, 10, 11, 12, 13, 14, 15 or more contiguous amino acids. In some embodiments, a useful polypeptide may comprise or consist of a fragment of a parent polypeptide. In some embodiments, a useful polypeptide as may comprise or consist of a plurality of fragments, each of which is found in the same parent polypeptide in a different spatial arrangement relative to one another than is found in the polypeptide of interest (e.g., fragments that are directly linked in the parent may be spatially separated in the polypeptide of interest or vice versa, and/or fragments may be present in a different order in the polypeptide of interest than in the parent), so that the polypeptide of interest is a derivative of its parent polypeptide.

Prevent or prevention: As used herein when used in connection with the occurrence of a disease, disorder, and/or condition, refers to reducing the risk of developing the disease, disorder and/or condition and/or to delaying onset of one or more characteristics or symptoms of the disease, disorder or condition. Prevention may be considered complete when onset of a disease, disorder or condition has been delayed for a predefined period of time.

Recombinant: As used herein, is intended to refer to polypeptides that are designed, engineered, prepared, expressed, created, manufactured, and/or or isolated by recombinant means, such as polypeptides expressed using a recombinant expression vector transfected into a host cell, polypeptides isolated from a recombinant, combinatorial human polypeptide library (e.g., Hoogenboom, *TIB Tech* 15:62, 1997; Azzazy *Clin. Biochem.* 35:425, 2002; Gavilondo *BioTechniques* 29:128, 2002; Hoogenboom *Immunology Today* 21:371, 2000), antibodies isolated from an animal (e.g., a mouse) that is transgenic for human immunoglobulin genes (see e.g., Taylor *Nuc. Acids Res.* 20:6287, 1992; Little *Immunology Today* 12:364, 2000; Kellermann *Curr. Opin. Biotechnol* 13:593, 2002; Murphy *Proc. Natl Acad Sci USA* 111:5153, 2104) or polypeptides prepared, expressed, created or isolated by any other means that involves splicing selected sequence elements to one another. In some embodiments, one or more of such selected sequence elements is found in nature. In some embodiments, one or more of such selected sequence elements is designed in silico. In some embodiments, one or more such selected sequence elements results from mutagenesis (e.g., in vivo or in vitro) of a known sequence element, e.g., from a natural or synthetic source. For example, in some embodiments, a recombinant antibody polypeptide is comprised of sequences found in the germline of a source organism of interest (e.g., human, mouse, etc.). In some embodiments, a recombinant antibody has an amino acid sequence that resulted from mutagenesis (e.g., in vitro or in vivo, for example in a transgenic animal), so that the amino acid sequences of the $V_H$ and $V_L$ regions of the recombinant antibodies are sequences that, while originating from and related to germline $V_H$ and $V_L$ sequences, may not naturally exist within the germline antibody repertoire in vivo.

Recovering: As used herein, refers to the process of rendering an agent or entity substantially free of other previously-associated components, for example by isolation, e.g., using purification techniques known in the art. In some embodiments, an agent or entity is recovered from a natural source and/or a source comprising cells.

Reference: As used herein describes a standard or control relative to which a comparison is performed. For example, in some embodiments, an agent, animal, individual, population, sample, sequence or value of interest is compared with a reference or control agent, animal, individual, population, sample, sequence or value. In some embodiments, a reference or control is tested and/or determined substantially simultaneously with the testing or determination of interest. In some embodiments, a reference or control is a historical reference or control, optionally embodied in a tangible medium. Typically, as would be understood by those skilled in the art, a reference or control is determined or characterized under comparable conditions or circumstances to those under assessment. Those skilled in the art will appreciate when sufficient similarities are present to justify reliance on and/or comparison to a particular possible reference or control.

Specific binding: As used herein, the term "specific binding" refers to an ability to discriminate between possible binding partners in the environment in which binding is to occur. A antibody agent that interacts with one particular target when other potential targets are present is said to "bind specifically" to the target with which it interacts. In some embodiments, specific binding is assessed by detecting or determining degree of association between the antibody agent and its partner; in some embodiments, specific binding is assessed by detecting or determining degree of dissociation of a antibody agent-partner complex; in some embodiments, specific binding is assessed by detecting or determining ability of the antibody agent to compete an alternative interaction between its partner and another entity. In some embodiments, specific binding is assessed by performing such detections or determinations across a range of concentrations Substantially: As used herein, the term "substantially" refers to the qualitative condition of exhibiting total or near-total extent or degree of a characteristic or property of interest. One of ordinary skill in the biological arts will understand that biological and chemical phenomena rarely, if ever, go to completion and/or proceed to completeness or achieve or avoid an absolute result. The term "substantially"

is therefore used herein to capture the potential lack of completeness inherent in many biological and chemical phenomena.

Therapeutic agent: As used herein, the phrase "therapeutic agent" in general refers to any agent that elicits a desired pharmacological effect when administered to an organism. In some embodiments, an agent is considered to be a therapeutic agent if it demonstrates a statistically significant effect across an appropriate population. In some embodiments, the appropriate population may be a population of model organisms. In some embodiments, an appropriate population may be defined by various criteria, such as a certain age group, gender, genetic background, preexisting clinical conditions, etc. In some embodiments, a therapeutic agent is a substance that can be used to alleviate, ameliorate, relieve, inhibit, prevent, delay onset of, reduce severity of, and/or reduce incidence of one or more symptoms or features of a disease, disorder, and/or condition. In some embodiments, a "therapeutic agent" is an agent that has been or is required to be approved by a government agency before it can be marketed for administration to humans. In some embodiments, a "therapeutic agent" is an agent for which a medical prescription is required for administration to humans.

Therapeutically effective amount: As used herein, is meant an amount that produces the desired effect for which it is administered. In some embodiments, the term refers to an amount that is sufficient, when administered to a population suffering from or susceptible to a disease, disorder, and/or condition in accordance with a therapeutic dosing regimen, to treat the disease, disorder, and/or condition. In some embodiments, a therapeutically effective amount is one that reduces the incidence and/or severity of, and/or delays onset of, one or more symptoms of the disease, disorder, and/or condition. Those of ordinary skill in the art will appreciate that the term "therapeutically effective amount" does not in fact require successful treatment be achieved in a particular individual. Rather, a therapeutically effective amount may be that amount that provides a particular desired pharmacological response in a significant number of subjects when administered to patients in need of such treatment. For example, in some embodiments, term "therapeutically effective amount", refers to an amount which, when administered to an individual in need thereof in the context of inventive therapy, will block, stabilize, attenuate, or reverse a cancer-supportive process occurring in said individual, or will enhance or increase a cancer-suppressive process in said individual. In the context of cancer treatment, a "therapeutically effective amount" is an amount which, when administered to an individual diagnosed with a cancer, will prevent, stabilize, inhibit, or reduce the further development of cancer in the individual. A particularly preferred "therapeutically effective amount" of a composition described herein reverses (in a therapeutic treatment) the development of a malignancy or helps achieve or prolong remission of a malignancy. A therapeutically effective amount administered to an individual to treat a cancer in that individual may be the same or different from a therapeutically effective amount administered to promote remission or inhibit metastasis. As with most cancer therapies, the therapeutic methods described herein are not to be interpreted as, restricted to, or otherwise limited to a "cure" for cancer; rather the methods of treatment are directed to the use of the described compositions to "treat" a cancer, i.e., to effect a desirable or beneficial change in the health of an individual who has cancer. Such benefits are recognized by skilled healthcare providers in the field of oncology and include, but are not limited to, a stabilization of patient condition, a decrease in tumor size (tumor regression), an improvement in vital functions (e.g., improved function of cancerous tissues or organs), a decrease or inhibition of further metastasis, a decrease in opportunistic infections, an increased survivability, a decrease in pain, improved motor function, improved cognitive function, improved feeling of energy (vitality, decreased malaise), improved feeling of well-being, restoration of normal appetite, restoration of healthy weight gain, and combinations thereof. In addition, regression of a particular tumor in an individual (e.g., as the result of treatments described herein) may also be assessed by taking samples of cancer cells from the site of a tumor such as a pancreatic adenocarcinoma (e.g., over the course of treatment) and testing the cancer cells for the level of metabolic and signaling markers to monitor the status of the cancer cells to verify at the molecular level the regression of the cancer cells to a less malignant phenotype. For example, tumor regression induced by employing the methods of this disclosure would be indicated by finding a decrease in any of the pro-angiogenic markers discussed above, an increase in anti-angiogenic markers described herein, the normalization (i.e., alteration toward a state found in normal individuals not suffering from cancer) of metabolic pathways, intercellular signaling pathways, or intracellular signaling pathways that exhibit abnormal activity in individuals diagnosed with cancer. Those of ordinary skill in the art will appreciate that, in some embodiments, a therapeutically effective amount may be formulated and/or administered in a single dose. In some embodiments, a therapeutically effective amount may be formulated and/or administered in a plurality of doses, for example, as part of a dosing regimen.

Treatment: As used herein, the term "treatment" (also "treat" or "treating") refers to any administration of a therapy that partially or completely alleviates, ameliorates, relives, inhibits, delays onset of, reduces severity of, and/or reduces incidence of one or more symptoms, features, and/or causes of a particular disease, disorder, and/or condition (e.g., cancer). In some embodiments, such treatment may be of a subject who does not exhibit signs of the relevant disease, disorder and/or condition and/or of a subject who exhibits only early signs of the disease, disorder, and/or condition. Alternatively or additionally, such treatment may be of a subject who exhibits one or more established signs of the relevant disease, disorder and/or condition. In some embodiments, treatment may be of a subject who has been diagnosed as suffering from the relevant disease, disorder, and/or condition. In some embodiments, treatment may be of a subject known to have one or more susceptibility factors that are statistically correlated with increased risk of development of the relevant disease, disorder, and/or condition.

Unit dose: The expression "unit dose," as used herein, refers to an amount administered as a single dose and/or in a physically discrete unit of a pharmaceutical composition. In many embodiments, a unit dose contains a predetermined quantity of an active agent. In some embodiments, a unit dose contains an entire single dose of the agent. In some embodiments, more than one unit dose is administered to achieve a total single dose. In some embodiments, administration of multiple unit doses is required, or expected to be required, in order to achieve an intended effect. A unit dose may be, for example, a volume of liquid (e.g., an acceptable carrier) containing a predetermined quantity of one or more therapeutic agents, a predetermined amount of one or more therapeutic agents in solid form, a sustained release formulation or drug delivery device containing a predetermined amount of one or more therapeutic agents, etc. It will be appreciated that a unit dose may be present in a formulation that includes any of a variety of components in addition to the therapeutic agent(s). For example, acceptable carriers (e.g., pharmaceutically acceptable carriers), diluents, stabilizers, buffers, preservatives, etc., may be included as described infra. It will be appreciated by those skilled in the art, in many embodiments, a total appropriate daily dosage of a particular therapeutic agent may comprise a portion, or a plurality, of unit doses, and may be decided, for example, by the attending physician within the scope of sound medical judgment. In some embodiments, the specific effective dose level for any particular subject or organism may depend upon a variety of factors including the disorder being treated and the severity of the disorder; activity of specific active compound employed; specific composition employed; age, body weight, general health, sex and diet of the subject; time of administration, and rate of excretion of the specific active compound employed; duration of the treatment; drugs and/or additional therapies used in combination or coincidental with specific compound(s) employed, and like factors well known in the medical arts.

Vector: As used herein, refers to a nucleic acid molecule capable of transporting another nucleic acid to which it has been linked. One type of vector is a "plasmid", which refers to a circular double stranded DNA loop into which additional DNA segments may be ligated. Another type of vector is a viral vector, wherein additional DNA segments may be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) can be integrated into the genome of a host cell upon introduction into the host cell, and thereby are replicated along with the host genome. Moreover, certain vectors are capable of directing the expression of genes to which they are operatively linked. Such vectors are referred to herein as "expression vectors."

Standard techniques may be used for recombinant DNA, oligonucleotide synthesis, and tissue culture and transformation (e.g., electroporation, lipofection). Enzymatic reactions and purification techniques may be performed according to manufacturer's specifications or as commonly accomplished in the art or as described herein. The foregoing techniques and procedures may be generally performed according to conventional methods well known in the art and as described in various general and more specific references that are cited and discussed throughout the present specification. See e.g., Sambrook et al., Molecular Cloning: A Laboratory Manual (2d ed., Cold Spring Harbor Laboratory Press, Cold Spring Harbor, N.Y. (1989)), which is incorporated herein by reference for any purpose.

DETAILED DESCRIPTION OF CERTAIN EMBODIMENTS

Immunotherapeutics have offered some progress in treatments for certain types of cancer. However, treatments options and prognosis for certain cancers remains an ongoing challenge. In particular, survival of patients with certain hematological cancers (e.g., myeloid leukemia) is still dismal.

CD33

CD33 (also known as Siglec-3, SIGLEC3, gp67, p67) is a 67 kDa plasma membrane protein that binds to sialic acid and is a member of the sialic acid-binding Ig-related lectin (SIGLEC) family of proteins. Siglec proteins are thought to be involved in diverse biological processes such as hematopoiesis, neuronal development and immunity (Vinson, M. et al., 1996 supra). Studies also suggest that Siglec proteins mediate cell adhesion/cell signaling through recognition of sialyated cell surface glycans (Kelm, S. et al., 1996 Glycoconj. J. 13:913-926; Kelm, S. et al., 1998 Eur. J. Biochem. 255:663-672; Vinson, M. et al., 1996 J. Biol. Chem. 271: 9267-9272). The extracellular portion of CD33 contains two immunoglobulin domains (one IgV and one IgC2 domain). The intracellular portion of CD33 contains immunoreceptor tyrosine-based inhibitory motifs (ITIMs). In the immune response, CD33 may act as an inhibitory receptor upon ligand induced tyrosine phosphorylation by recruiting cytoplasmic phosphatase(s) that block signal transduction through dephosphorylation of signaling molecules.

CD33 is known to be expressed on myeloid cells. CD33 expression has also been reported on a number of malignant cells. Although CD33 has been targeted for treatment of cancer, e.g., acute myeloid leukemia, no effective CD33-targeted treatments are currently on the market.

CD33 Antibody Agents

A number of agents of that target CD33 have been produced, but these agents have a number of shortcomings which may include poor half life, poor in vivo function and/or adverse effects.

Gemtuzumab ozogamicin (GO, Mylotarg™) is a humanized IgG4 anti-CD33 monoclonal antibody joined to N-acetyl-γ-calicheamicin dimethyl hydrazide (CalichDMH) (Hamann P R, et al. Bioconjug Chem 13:47-58, 2002). Upon binding to CD33, GO is internalized and the release of toxic calicheamicin induces DNA damage culminating in cell death. However, since its FDA approval in 2000 for the treatment of CD33+ AML, several trials have reported heterogeneous clinical responses and acquired resistance is common.

While initially, GO was associated with improved treatment of patients with AML, further clinical trials and post-marketing assessment revealed lack of efficacy and fatal side effects. An interim analysis of a clinical trial showed that GO plus chemotherapy is not superior to chemotherapy alone (Petersdorf S, et al. Blood 114:790-790, 2009 and Petersdorf S H, et al., Blood 121:4854-60, 2013). Besides, the rate of fatal induction adverse effects was higher in the GO treated patients. Id. Therefore GO was withdrawn from the market in 2010 and currently the FDA does not recommend GO for treatment of AML.

Lintuzumab is a humanized IgG1 monoclonal antibody against CD33. In preclinical models of AML, lintuzumab demonstrated some therapeutic potential (Sutherland M K, et al. MAbs 2:440-8, 2010); however, in case of heterogenous population of patients, the results of a phase IIb clinical trial showed that combination of lintuzumab and cytarabine was not superior to cytarabine alone in adults with AML (Sekeres M A, et al. Haematologica 98:119-28, 2013). Therefore clinical development of lintuzumab was terminated in 2010 (Laszlo G S, et al. Blood Rev 28:143-53, 2014).

AVE9633 is humanized IgG1 anti-CD33 antibody/maytansinoid conjugate. As a single agent, it has very modest activity in AML patients. Its clinical development was therefore terminated (Laszlo G S, et al. Blood Rev 28:143-53, 2014).

HuM-195/rGel is a humanized anti-CD33 antibody conjugated to the recombinant gelonin toxin. In a phase I clinical trial, it demonstrated very modest clinical activity with hypoxia and hypotension as limiting dose toxicities (Borthakur G, et al. Haematologica 98:217-21, 2013).

Lintuzumab-Ac225 (Actimab) is an Ac225-conjugated form of lintuzumab. It was used in a phase I clinical trial of AML. Preliminary data showed a reduction of bone marrow blasts in 67% of the patients; however, no complete remission was observed and grade-4 thrombocytopenia was observed as the dose limiting toxicity (Ravandi F, et al., Blood 122:1460-1460, 2013). Furthermore, complex logistic of radiolabeled antibodies adds to their disadvantages.

Lintuzumab-Bi213 is another form of radiolabeled lintuzumab. Results of a phase I/II clinical trial on AML patients showed significant reduction of bone marrow blasts. Nevertheless, 16% of patients showed grade 3/4 liver function abnormalities and 10% of patients who received the maximum tolerated dose died due to treatment (Rosenblat T L, et al. Clin Cancer Res 16:5303-11, 2010).

AMG330 is a bispecific T-cell engager (BiTE®) composed of the scFv of anti-CD33 and anti-CD3 antibodies connected via a linker. In vitro, AMG330 activates and expands T cells from AML patients. In vivo, AMG330 could slow down the growth of subcutaneous AML but did not lead to tumor shrinkage (Aigner M, et al. Leukemia 27:1107-15, 2013). Furthermore, AMG330 rescued 50% of mice injected with a human AML cell line (Friedrich M, et al. Mol Cancer Ther 13:1549-57, 2014). However, daily injection of antibody for 26 days was necessary for clinical activity which is due to small size of the drug and leading to short in vivo half-life. A phase I clinical trial (NCT02520427) for treatment of refractory/relapsed AML patients began recruiting again after it was suspended. Continuous infusion of the drug which mandates hospitalization of patients for several weeks is a disadvantage of this agent.

Provided Antibody Agents

The present disclosure encompasses the recognition that it would be desirable to develop multispecific antibody agents (e.g., bispecific antibody agents) that are variants of huM195. The present disclosure particularly provides such multispecific antibody agents (e.g., CD33-BsAb agents). In some embodiments, multispecific antibody agents of the present disclosure comprise a first binding moiety based on huM195 (i.e., an anti-CD33 moiety) and a second binding moiety. The present disclosure provides particular multispecific antibody agents that include an anti-CD33 moiety, such as an antibody fusion with an single chain Fv fragment (scFv).

The present disclosure encompasses the recognition, that at least in some embodiments, an injectable multispecific antibody agent (e.g., a CD33-BsAb agent for parenteral administration) that drives polyclonal cytotoxic T lymphocytes to leukemia would be a desirable therapeutic and/or diagnostic agent. In some embodiments, some advantages envisioned for such a multispecific antibody agent (e.g., a bispecific antibody agent (BsAb), such as a CD33-BsAb agent) include that it could be accessible to patients in ordinary oncology clinics, could administrated as an outpatient, and/or could be offered at reasonable cost. Yet, given the many possible platforms of BsAb (Kontermann R., MAbs 4, 2012), there is yet a consensus on the most clinically effective blueprint. Most CD33-CD3 bispecific antibody constructs are monovalent with respect to CD33 and CD3, with an assumption that if an antibody agent is bivalent for anti-CD3, nonspecific activation of T cells will be clinically prohibitive (which is believed to be due, at least in part, of induction of a cytokine storm). Yet, mouse OKT3, a bivalent mouse IgG, was the first FDA approved monoclonal antibody. Since 1986 it has been widely used for the treatment of organ rejection after allogeneic renal, heart and liver transplants. In 1996 it was found to be safe for prophylaxis of transplant rejection. Throughout the decades, it has remained on the market until most recently when more effective drugs make it obsolete. One major weakness of monovalent agents is inferior tumor antigen binding avidity. The present disclosure encompasses the recognition, that unless affinity of a single chain variable fragment (scFv) is substantially improved, its targeting differential into tumor versus normal tissues will suffer.

For example, in some embodiments, provided multispecific antibody agents (e.g., bispecific antibody agents, such as CD33-BsAb) use a IgG-scFv format. Provided multispecific antibody agents (e.g., bispecific antibody agents, such as CD33-BsAb) can offer advantages over current CD33 antibody agents. Without wishing to be bound by theory, it is envisioned that multispecific antibody agents (e.g., bispecific antibody agents, such as CD33-BsAb) of the present disclosure have a number of desirable characteristics. In some embodiments, such desirable characteristics may include one or more of: (1) an optimal size (100-200 kd) to maximize tumor uptake, (2) bivalency towards the tumor target to maintain avidity, (3) a scaffold that is naturally assembled like any IgG (heavy chain and light chain) in mammalian cells (e.g., CHO cells), purifiable by standard protein A affinity chromatography, (4) structural arrangement to render the anti-CD3 component functionally monovalent, hence reducing nonspecific activation of T cells, (5) a platform with proven tumor targeting efficiency in animal models. Additionally, and without wishing to be bound by theory, it is envisioned that multispecific antibody agents (e.g., bispecific antibody agents, such as CD33-BsAb) of the present disclosure in a IgG-scFv format may overcome the PD1-PDL1 inhibition that has plagued the entire field of T cell based therapy. In some embodiments, multispecific antibody agents of the present disclosure (e.g., bispecific antibody agents, such as CD33-CD3 IgG-scFv) can recruit polyclonal T-cells via the CD3 receptor.

In some embodiments, multispecific antibody agents (e.g., bispecific antibody agents, such as CD33-BsAb) of the present disclosure of the present disclosure can generate anti-tumor responses at picomolar $EC_{50}$ in vitro. In some embodiments, a CD33-BsAb agent of the present disclosure can induce substantial (e.g., greater than 15%, 20%, 25%, 30%, 35%, 40%, 45%, 50%, 55%, 60%, 65%, 70%, 75%, 80%, 85%, 90%) killing of cancer cells (e.g., a cancer cell line, such as an AML cell line) in vitro with $EC_{50}$ in a range of 0.01 pM to 500 nM. In some embodiments, a CD33-BsAb agent of the present disclosure can induce substantial (e.g., greater than 15%, 20%, 25%, 30%, 35%, 40%, 45%, 50%, 55%, 60%, 65%, 70%, 75%, 80%, 85%, 90%) killing of cancer cells (e.g., a cancer cell line, such as an AML cell line) in vitro with $EC_{50}$ in a range of 0.1 pM to 1 nM.

In some embodiments, multispecific antibody agents (e.g., bispecific antibody agents, such as CD33-BsAb) can eradicate cancer in preclinical mouse models. In some embodiments, a CD33-BsAb agent of the present disclosure can reduce cancer burden (e.g. presence of cancer cells) by 80%, 85%, 90%, 95%, 96%, 97%, 98%, 99%, or 100% in a preclinical mouse model. In some certain embodiments, a CD33-CD3 IgG-scFv agent can eradicate cancer in a preclinical mouse model. In some certain embodiments, a CD33-CD3 IgG-scFv agent can reduce cancer burden (e.g. presence of cancer cells) of a myeloid leukemia by 80%, 85%, 90%, 95%, 96%, 97%, 98%, 99%, or 100% in a preclinical mouse model.

In some embodiments, multispecific antibody agents (e.g., bispecific antibody agents, such as CD33-BsAb) can eradicate myeloid leukemia in preclinical mouse models. In some embodiments, a CD33-BsAb agent of the present disclosure can reduce cancer burden (e.g. presence of cancer cells) of a myeloid leukemia by 80%, 85%, 90%, 95%, 96%, 97%, 98%, 99%, or 100% in a preclinical mouse model. In some certain embodiments, a CD33-CD3 IgG-scFv agent can eradicate myeloid leukemia in a preclinical mouse model. In some certain embodiments, a CD33-CD3 IgG-scFv agent can reduce cancer burden (e.g. presence of cancer cells) of a myeloid leukemia by 80%, 85%, 90%, 95%, 96%, 97%, 98%, 99%, or 100% in a preclinical mouse model. In some embodiments, provided multispecific antibody agents (e.g., bispecific antibody agents, such as CD33-BsAb) are effective in vivo. As described in the examples below, an exemplary CD33 bispecific antibody agent achieved cures in of animals bearing human leukemic cell lines in vivo, even when the leukemia burden was large (See also FIGS. 5-7). This is despite bivalency towards CD33 where conventional wisdom would have predicted rapid endocytosis and loss of antigen from tumor cell surface.

In some embodiments, multispecific antibody agents (e.g., bispecific antibody agents, such as CD33-BsAb) can reduce extramedullary leukemia burden in preclinical mouse models. In some embodiments, a CD33-BsAb agent of the present disclosure can reduce extramedullary leukemia burden (e.g. presence of cancer cells) by 40%, 50%, 60%, 70%, 80%, 85%, 90%, 95%, 96%, 97%, 98%, 99%, or 100% in a preclinical mouse model. In some certain embodiments, a CD33-CD3 IgG-scFv agent reduce extramedullary leukemia burden in a preclinical mouse model. In some certain embodiments, a CD33-CD3 IgG-scFv agent can reduce extramedullary leukemia burden (e.g. presence of cancer cells) by 40%, 50%, 60%, 70%, 80%, 85%, 90%, 95%, 96%, 97%, 98%, 99%, or 100% in a preclinical mouse model.

In some embodiments, multispecific antibody agents (e.g., bispecific antibody agents, such as CD33-BsAb) of the present disclosure include an anti-CD3 humanized OKT3 (huOKT3) single chain Fv fragment (ScFv) fused to the carboxyl end of the IgG1 light chain.

In some embodiments, a multispecific antibody agent that binds CD33 is a humanized M195 antibody. In some embodiments, an humanized M195 antibody comprises a heavy chain variable region with M195 heavy chain CDR sequences (CDR1, CDR2 and CDR3) grafted onto a human framework, such as IGHV1-3*01 and IGHJ4*01. In some embodiments, an humanized M195 antibody comprises a light chain variable region with M195 light chain CDR sequences grafted onto a human framework, such as IGKV3D11*02 and IGKJ4*01. Exemplary humanized M195 heavy chain and light chain variable region sequences are provided below:

```
H1 variable region
                                        SEQ ID NO: 1
EVQLQQSGPEVVKPGASVKISCKASGYTFTDYNMHWVKQAHGQSLE

WIGYIYPYNGGTGYNQKFKSKATLTVDNSASTAYMEVRSLTSEDTAV

YYCARGRPAMDYWGQGTLVTVSS

H2 variable region
                                        SEQ ID NO: 2
EVQLVQSGPEVVKPGASVKISCKASGYTFTDYNMHWVRQAHGQSLE

WIGYIYPYNGGTGYNQKFKSRATLTVDNSASTAYMEVSSLRSEDTAV

YYCARGRPAMDYWGQGTLVTVSS

L1 variable region
                                        SEQ ID NO: 3
EIVLTQSPATLSVSLGQRATISCRASESVDNYGISFMNWFQQKPGQPPK

LLIYAASNQGSGVPARFSGSGSGTDFTLTIHPMEEDDTAMYFCQQSKE

VPWTFGGGTKLEIK

L2 variable region
                                        SEQ ID NO: 4
EIVLTQSPATLSVSLGERATISCRASESVDNYGISFMNWFQQKPGQPPR

LLIYAASNQGSGVPARFSGSGPGTDFTLTISSMEPEDFAMYFCQQSKE

VPWTFGGGTKLEIK
```

In some embodiments, a provided multispecific antibody agent (e.g., bispecific antibody agent, such as CD33-BsAb) includes an anti-CD33 heavy chain, wherein the anti-CD33 heavy chain variable region includes a sequence that is at least about 50% (e.g., at least about 55%, 60%, 65%, 70%, 75%, 80%, 85%, 90%, 95%, 96%, 97%, 98%, or 99%) identical to SEQ ID NO:1 or 2. In some embodiments, a provided multispecific antibody agent (e.g., bispecific antibody agent, such as CD33-BsAb) includes an anti-CD33 light chain variable domain comprising a sequence that is at least about 50% (e.g., at least about 55%, 60%, 65%, 70%, 75%, 80%, 85%, 90%, 95%, 96%, 97%, 98%, or 99%) identical to SEQ ID NO: 3 or 4.

In some embodiments, a CD33-BsAb of the present disclosure includes a heavy chain and a light chain fusion polypeptide, wherein the heavy chain variable region includes a sequence that is at least about 50% (e.g., at least about 55%, 60%, 65%, 70%, 75%, 80%, 85%, 90%, 95%, 96%, 97%, 98%, or 99%) identical to SEQ ID NO:1 or 2 and wherein the light chain portion of the fusion polypeptide includes a sequence that is at least about 50% (e.g., at least about 55%, 60%, 65%, 70%, 75%, 80%, 85%, 90%, 95%, 96%, 97%, 98%, or 99%) identical to SEQ ID NO: 3 or 4.

In some embodiments, a CD33-BsAb of the present disclosure includes a heavy chain comprising a sequence that is at least about 50% (e.g., at least about 55%, 60%, 65%, 70%, 75%, 80%, 85%, 90%, 95%, 96%, 97%, 98%, or 99%) identical to SEQ ID NO:24 and a light chain portion of the fusion polypeptide that includes a sequence that is at least about 50% (e.g., at least about 55%, 60%, 65%, 70%, 75%, 80%, 85%, 90%, 95%, 96%, 97%, 98%, or 99%) identical to SEQ ID NO: 26.

```
H1 cDNA sequence (leader sequence underlined)
                                        SEQ ID NO: 5
atgggctggtcctgcatcatcctgtttctggtggctaccgccaccggcgaggtgcagctgcagcagtctggacc cgaggtcgtgaagcctggcgcctccgtgaagatctcctgcaaggcctccggctacaccttcaccgactacaac atgcactgggtcaagcaggcccacggccagtccctggaatggatcggctacatctaccctacaacggcggc accggctacaaccagaagttcaagtccaaggccaccctgaccgtggacaactccgcctccaccgcctacatg
```

-continued gaagtgcggtccctgacctctgaggacaccgccgtgtactactgcgccagaggcagacccgccatggactatt ggggccagggcaccctcgtgaccgtgtcctctgcttctaccaagggcccatcggtcttccccctggcaccctcc tccaagagcacctctgggggcacagcggccctgggctgcctggtcaaggactacttccccgaaccggtgacg gtgtcgtggaactcaggcgccctgaccagcggcgtgcacaccttcccggccgtcctacagtcctcaggactct actcctcagcagcgtggtgaccgtgccctccagcagcttgggcacccagacctacatctgcaacgtgaatca caagcccagcaacaccaaggtggacaagagagttgagcccaaatcttgtgacaaaactcacacatgcccacc gtgcccagcacctgaactcctgggggaccgtcagtcttcctcttccccccaaaacccaaggacaccctcatg atctcccggacccctgaggtcacatgcgtggtggtggacgtgagccacgaagaccctgaggtcaagttcaact ggtacgtggacggcgtggaggtgcataatgccaagacaaagccgcgggaggagcagtacaacagcacgta ccgtgtggtcagcgtcctcaccgtcctgcaccaggactggctgaatggcaaggagtacaagtgcaaggtctcc aacaaagccctcccagcccccatcgagaaaaccatctccaaagccaaagggcagccccgagaaccacaggt gtacaccctgcccccatcccgggatgagctgaccaagaaccaggtcagcctgacctgcctggtcaaaggcttc tatcccagcgacatcgccgtggagtgggagagcaatgggcagccggagaacaactacaagaccacgcctcc cgtgctggactccgacggctccttcttcctctacagcaagctcaccgtggacaagagcaggtggcagcaggg gaacgtcttctcatgctccgtgatgcatgaggctctgcacaaccactacacgcagaagagcctctccctgtctcc gggtaaatga H2 cDNA sequence (leader sequence underlined)

SEQ ID NO: 6

<u>atgggctggtcctgcatcatcctgtttctggtggctaccgccaccggc</u>gaggtgcagctggtgcagtctggacc cgaggtcgtgaagcctggcgccctccgtgaagatctcctgcaaggcctccggctacaccttcaccgactacaac atgcactgggtgcgacaggcccacggccagtccctggaatggatcggctacatctaccccctacaacggcggc accggctacaaccagaagttcaagtctcgggccaccctgaccgtggacaactctgcctctaccgcctacatgg aagtgtcctccctgagatccgaggacaccgccgtgtactactgcgccagaggcagacccgccatggactattg gggcagggcaccctcgtgaccgtgtctagcgcttctaccaagggcccatcggtcttccccctggcaccctcct ccaagagcacctctgggggcacagcggccctgggctgcctggtcaaggactacttccccgaaccggtgacg gtgtcgtggaactcaggcgccctgaccagcggcgtgcacaccttcccggccgtcctacagtcctcaggactct actcctcagcagcgtggtgaccgtgccctccagcagcttgggcacccagacctacatctgcaacgtgaatca caagcccagcaacaccaaggtggacaagagagttgagcccaaatcttgtgacaaaactcacacatgcccacc gtgcccagcacctgaactcctgggggaccgtcagtcttcctcttccccccaaaacccaaggacaccctcatg atctcccggacccctgaggtcacatgcgtggtggtggacgtgagccacgaagaccctgaggtcaagttcaact ggtacgtggacggcgtggaggtgcataatgccaagacaaagccgcgggaggagcagtacaacagcacgta ccgtgtggtcagcgtcctcaccgtcctgcaccaggactggctgaatggcaaggagtacaagtgcaaggtctcc aacaaagccctcccagcccccatcgagaaaaccatctccaaagccaaagggcagccccgagaaccacaggt gtacaccctgcccccatcccgggatgagctgaccaagaaccaggtcagcctgacctgcctggtcaaaggcttc tatcccagcgacatcgccgtggagtgggagagcaatgggcagccggagaacaactacaagaccacgcctcc cgtgctggactccgacggctccttcttcctctacagcaagctcaccgtggacaagagcaggtggcagcaggg gaacgtcttctcatgctccgtgatgcatgaggctctgcacaaccactacacgcagaagagcctctccctgtctcc gggtaaatga L1 cDNA sequence (leader sequence underlined)

SEQ ID NO: 7

<u>atgggctggtcctgcatcatcctgtttctggtggctaccgccaccggc</u>gagatcgtgctgactcagtctcctgcc accctgtccgtgtccctgggccagagagccaccatctcttgcagagcctccgagtccgtggacaactacggca tctccttcatgaactggttccagcagaagcccggccagccccccaagctgctgatctacgccgcttccaatcag -continued

```
ggctctggcgtgcccgctagattctccggctctggctctggcaccgacttcaccctgaccatccacccatgga agaggacgacaccgccatgtactttgccagcagtccaaagaggtgccctggaccttggcggaggcaccaa gctggaaatcaagcggaccgtggccgctccctccgtgttcatcttcccaccttccgacgagcagctgaagtccg gcaccgcttctgtcgtgtgcctgctgaacaacttctaccccgcgaggccaaggtgcagtggaaggtggacaa cgccctgcagtccggcaactcccaggaatccgtgaccgagcaggactccaaggacagcacctactccctgtc ctctaccctgaccctgtccaaggccgactacgagaagcacaaggtgtacgcctgcgaagtgacccaccaggg cctgtctagccccgtgaccaagtctttcaaccggggcgagtgctag
```

L2 cDNA sequence (leader sequence underlined)

SEQ ID NO: 8

```
atgggctggtcctgcatcatcctgtttctggtggctaccgccaccggcgagatcgtgctgactcagtctcctgcc accctgtccgtgtccctgggcgagagagccaccatctcttgcagagcctccgagtccgtggacaactacggca tctccttcatgaactggttccagcagaagcccggccagcctcctcggctgctgatctacgccgcttccaatcagg gctctggcgtgcccgctagattctccggatctggccctggcaccgactttaccctgaccatctcctccatggaac ccgaggacttcgccatgtactttgccagcagtccaaagaggtgccctggaccttggcggaggcaccaagct ggaaatcaagcggaccgtggccgctccctccgtgttcatcttcccaccttccgacgagcagctgaagtccggc accgcttctgtcgtgtgcctgctgaacaacttctaccccgcgaggccaaggtgcagtggaaggtggacaacg ccctgcagtccggcaactcccaggaatccgtgaccgagcaggactccaaggacagcacctactccctgtcctc caccctgaccctgagcaaggccgactacgagaagcacaaggtgtacgcctgcgaagtgacccaccagggcc tgtctagccccgtgaccaagtctttcaaccggggcgagtgctag
```

In some embodiments, a provided multispecific antibody agent (e.g., bispecific antibody agent, such as CD33-BsAb) includes an anti-CD33 heavy chain, wherein the anti-CD33 heavy chain variable region is encoded by a sequence that is at least about 50% (e.g., at least about 55%, 60%, 65%, 70%, 75%, 80%, 85%, 90%, 95%, 96%, 97%, 98%, or 99%) identical to SEQ ID NO:5 or 6. In some embodiments, a provided multispecific antibody agent (e.g., bispecific antibody agent, such as CD33-BsAb) includes an anti-CD33 light chain variable domain that is encoded by a sequence that is at least about 50% (e.g., at least about 55%, 60%, 65%, 70%, 75%, 80%, 85%, 90%, 95%, 96%, 97%, 98%, or 99%) identical to SEQ ID NO: 7 or 8.

In some embodiments, a CD33-BsAb of the present disclosure includes a heavy chain and a light chain fusion polypeptide, wherein the heavy chain variable region is encoded by a sequence that is at least about 50% (e.g., at least about 55%, 60%, 65%, 70%, 75%, 80%, 85%, 90%, 95%, 96%, 97%, 98%, or 99%) identical to SEQ ID NO:5 or 6 and wherein the light chain portion of the fusion polypeptide is encoded by a sequence that is at least about 50% (e.g., at least about 55%, 60%, 65%, 70%, 75%, 80%, 85%, 90%, 95%, 96%, 97%, 98%, or 99%) identical to SEQ ID NO: 7 or 8.

In some embodiments, a CD33-BsAb of the present disclosure includes a heavy chain encoded by a sequence that is at least about 50% (e.g., at least about 55%, 60%, 65%, 70%, 75%, 80%, 85%, 90%, 95%, 96%, 97%, 98%, or 99%) identical to SEQ ID NO:23 and a light chain portion of the fusion polypeptide encoded by a sequence that is at least about 50% (e.g., at least about 55%, 60%, 65%, 70%, 75%, 80%, 85%, 90%, 95%, 96%, 97%, 98%, or 99%) identical to SEQ ID NO: 25.

In some embodiments, a multispecific antibody agent comprises a monoclonal anti-CD33 antibody, comprising two heavy chains and two light chains. In some embodiments, a monoclonal anti-CD33 antibody is a humanized M195 antibody. Exemplary humanized M195 heavy chain and light chain sequences are provided below:

Heavy chain sequence (H2)

SEQ ID NO: 9

EVQLVQSGPEVVKPGASVKISCKASGYTFTDYNMHWVRQAHGQSLE

WIGYIYPYNGGTGYNQKFKSRATLTVDNSASTAYMEVSSLRSEDTAV

YYCARGRPAMDYWGQGTLVTVSSASTKGPSVFPLAPSSKSTSGGTAA

LGCLVKDYFPEPVTVSWNSGALTSGVHTFPAVLQSSGLYSLSSVVTVP

SSSLGTQTYICNVNHKPSNTKVDKRVEPKSCDKTHTCPPCPAPELLGG

PSVFLFPPKPKDTLMISRTPEVTCVVVDVSHEDPEVKFNWYVDGVEV

HNAKTKPREEQYNSTYRVVSVLTVLHQDWLNGKEYKCKVSNKALPA

PIEKTISKAKGQPREPQVYTLPPSRDELTKNQVSLTCLVKGFYPSDIAV

EWESNGQPENNYKTTPPVLDSDGSFFLYSKLTVDKSRWQQGNVFSCS

VMHEALHNHYTQKSLSLSPGK

Light chain sequence (L2)

SEQ ID NO: 10

EIVLTQSPATLSVSLGERATISCRASESVDNYGISFMNWFQQKPGQPPR

LLIYAASNQGSGVPARFSGSGPGTDFTLTISSMEPEDFAMYFCQQSKE

VPWTFGGGTKLEIKRTVAAPSVFIFPPSDEQLKSGTASVVCLLNNFYPR

EAKVQWKVDNALQSGNSQESVTEQDSKDSTYSLSSTLTLSKADYEKH

KVYACEVTHQGLSSPVTKSFNRGEC

In some embodiments, a provided multispecific antibody agent (e.g., bispecific antibody agent, such as CD33-BsAb)

includes a heavy chain and a light chain fusion polypeptide, wherein the heavy chain includes a sequence that is at least about 50% (e.g., at least about 55%, 60%, 65%, 70%, 75%, 80%, 85%, 90%, 95%, 96%, 97%, 98%, or 99%) identical to SEQ ID NO:9 and wherein the light chain portion of the fusion polypeptide includes a sequence that is at least about 50% (e.g., at least about 55%, 60%, 65%, 70%, 75%, 80%, 85%, 90%, 95%, 96%, 97%, 98%, or 99%) identical to SEQ ID NO:10.

In some embodiments, a multispecific antibody agent comprises a monoclonal antibody (e.g. a huCD33 monoclonal antibody) and a scFv. In some embodiments, a scFv is fused (i.e., covalently linked) to a light chain of a monoclonal antibody (e.g., a huCD33 monoclonal antibody). In some embodiments, a scFv is fused to the C-terminus of a light chain of a monoclonal antibody (e.g., a huCD33 monoclonal antibody). In some embodiments, a scFv is directly fused to the C-terminus of a light chain of a monoclonal antibody (e.g., a huCD33 monoclonal antibody). In some embodiments, a scFv is covalently linked to the C-terminus of a light chain of a monoclonal antibody (e.g., a huCD33 monoclonal antibody) via a linker sequence.

In some embodiments, a multispecific antibody agent comprises two heavy chains and two fusion polypeptides. In some embodiments, the two heavy chains are identical. In some embodiments, the two fusion polypeptides are identical. In some embodiments, a provided multispecific antibody agent (e.g., bispecific antibody agent, such as CD33-BsAb) comprises two identical heavy chains and two identical light chain fusion polypeptides. Such multispecific antibody agents with two identical heavy chains and two identical light chain fusion polypeptides will be tetravalent with divalent binding to each target (e.g., divalency for each of CD33 and a second target) In some embodiments, a fusion polypeptide comprises an immunoglobulin light chain fused to a scFv, a VHH or to any other binding domain. In some embodiments, the fusion polypeptides comprise an immunoglobulin light chain fused to a scFv.

In some embodiments, a fusion polypeptide of a multispecific antibody agent of the present disclosure further comprises a linker. A multitude of linkers are known in the art, including, for example, Gly-Ser linkers (e.g., GGGGS linkers). In some embodiments, a fusion polypeptide comprises from N-terminus to C-terminus an immunoglobulin light chain, a linker and a scFv. Linker composition and length can vary as appropriate.

In some particular embodiments, provided multispecific antibody agents (e.g., bispecific antibody agents, such as a CD33-BsAb), or sequences thereof, may comprise a anti-CD33 variable domain and another binding domain, such as a domain that binds to a moiety on T cells (e.g., CD3), a domain that binds to an organic or inorganic compound (e.g., a Benzyl-DOTA-metal), etc. In some particular embodiments, provided multispecific antibody agents (e.g., bispecific antibody agents, such as CD33-BsAb), or sequences thereof, may comprise a anti-CD33 variable domain and another binding domain, including anti-OKT3 for retargeting T cells for tumor cytotoxicity, or Benzyl-DOTA-metal, C825 for multistep pretargeting, or Clone 35, CD137, for ADCC with anti-4-1BB-scFv as agonist, or with CD137, 4-1BBL for ADC with 4-1BBL as an agonist.

In some embodiments, a multispecific antibody agent is a bispecific antibody agent that includes an anti-CD33 binding domain and an anti-CD3 binding domain. In some embodiments, an anti-CD3 binding domain is an scFv. Exemplary anti-CD3 scFv sequences are provided below:

huOKT3 scFv without disulfide bond:
SEQ ID NO: 11
QVQLVQSGGGVVQPGRSLRLSCKASGYTFTRYTMHWVRQAPGKGLE
WIGYINPSRGYTNYNQKFKDRFTISRDNSKNTAFLQMDSLRPEDTGVY
FCARYYDDHYSLDYWGQGTPVTVSSGGGGSGGGGSGGGGSGGGGS
GGGGSGGGGSDIQMTQSPSSLSASVGDRVTITCSASSSVSYMNVVYQQ
TPGKAPKRWIYDTSKLASGVPSRFSGSGSGTDYTFTISSLQPEDIATYY
CQQWSSNPFTFGQGTKLQITR huOKT3 scFv with 5-aa linker
SEQ ID NO: 12
QVQLVQSGGGVVQPGRSLRLSCKASGYTFTRYTMHWVRQAPGKCLE
WIGYINPSRGYTNYNQKFKDRFTISRDNSKNTAFLQMDSLRPEDTGVY
FCARYYDDHYSLDYWGQGTPVTVSSGGGGSDIQMTQSPSSLSASVGD
RVTITCSASSSVSYMNWYQQTPGKAPKRWIYDTSKLASGVPSRFSGSG
SGTDYTFTISSLQPEDIATYYCQQWSSNPFTFGCGTKLQITR huOKT3 scFv with 10-aa linker
SEQ ID NO: 13
QVQLVQSGGGVVQPGRSLRLSCKASGYTFTRYTMHWVRQAPGKCLE
WIGYINPSRGYTNYNQKFKDRFTISRDNSKNTAFLQMDSLRPEDTGVY
FCARYYDDHYSLDYWGQGTPVTVSSGGGGSGGGGSDIQMTQSPSSLS
ASVGDRVTITCSASSSVSYMNWYQQTPGKAPKRWIYDTSKLASGVPS
RFSGSGSGTDYTFTISSLQPEDIATYYCQQWSSNPFTFGCGTKLQITR huOKT3 scFv with 15-aa linker
SEQ ID NO: 14
QVQLVQSGGGVVQPGRSLRLSCKASGYTFTRYTMHWVRQAPGKCLE
WIGYINPSRGYTNYNQKFKDRFTISRDNSKNTAFLQMDSLRPEDTGVY
FCARYYDDHYSLDYWGQGTPVTVSSGGGGSGGGGSGGGGSDIQMTQ
SPSSLSASVGDRVTITCSASSSVSYMNVVYQQTPGKAPKRWIYDTSKLA
SGVPSRFSGSGSGTDYTFTISSLQPEDIATYYCQQWSSNPFTFGCGTKL
QITR huOKT3 scFv with 20-aa linker
SEQ ID NO: 15
QVQLVQSGGGVVQPGRSLRLSCKASGYTFTRYTMHWVRQAPGKCLE
WIGYINPSRGYTNYNQKFKDRFTISRDNSKNTAFLQMDSLRPEDTGVY
FCARYYDDHYSLDYWGQGTPVTVSSGGGGSGGGGSGGGGSGGGGS
DIQMTQSPSSLSASVGDRVTITCSASSSVSYMNWYQQTPGKAPKRWIY
DTSKLASGVPSRFSGSGSGTDYTFTISSLQPEDIATYYCQQWSSNPFTF
GCGTKLQITR huOKT3 scFv with 25-aa linker
SEQ ID NO: 16
QVQLVQSGGGVVQPGRSLRLSCKASGYTFTRYTMHWVRQAPGKCLE
WIGYINPSRGYTNYNQKFKDRFTISRDNSKNTAFLQMDSLRPEDTGVY
FCARYYDDHYSLDYWGQGTPVTVSSGGGGSGGGGSGGGGSGGGGS
GGGGSDIQMTQSPSSLSASVGDRVTITCSASSSVSYMNWYQQTPGKAP
KRWIYDTSKLASGVPSRFSGSGSGTDYTFTISSLQPEDIATYYCQQWSS
NPFTFGCGTKLQITR huOKT3 scFv with 30-aa linker

SEQ ID NO: 17

QVQLVQSGGGVVQPGRSLRLSCKASGYTFTRYTMHWVRQAPGKCLE

WIGYINPSRGYTNYNQKFKDRFTISRDNSKNTAFLQMDSLRPEDTGVY

FCARYYDDHYSLDYWGQGTPVTVSSGGGGSGGGGSGGGGSGGGGS

GGGGSGGGGSDIQMTQSPSSLSASVGDRVTITCSASSSVSYMNVVYQQ

TPGKAPKRWIYDTSKLASGVPSRFSGSGSGTDYTFTISSLQPEDIATYY

CQQWSSNPFTFGCGTKLQITR huOKT3 scFv with disulfide bond:

SEQ ID NO: 27

QVQLVQSGGGVVQPGRSLRLSCKASGYTFTRYTMHWVRQAPGKCLE

WIGYINPSRGYTNYNQKFKDRFTISRDNSKNTAFLQMDSLRPEDTGVY

FCARYYDDHYSLDYWGQGTPVTVSSGGGGSGGGGSGGGGSGGGGS

GGGGSGGGGSDIQMTQSPSSLSASVGDRVTITCSASSSVSYMNWYQQ

TPGKAPKRWIYDTSKLASGVPSRFSGSGSGTDYTFTISSLQPEDIATYY

CQQWSSNPFTFGCGTKLQITR

In some embodiments, a CD33-BsAb of the present disclosure includes a light chain fusion polypeptide, wherein the light chain fusion polypeptide includes a sequence that is at least about 50% (e.g., at least about 55%, 60%, 65%, 70%, 75%, 80%, 85%, 90%, 95%, 96%, 97%, 98%, or 99%) identical to any one of SEQ ID NOs:11-17 and 27.

In some embodiments, a multispecific antibody agent is a bispecific antibody agent that includes an anti-CD33 binding domain and an anti-Benzyl-DOTA binding domain. Such bispecific antibody agents can be used, for example, in pretargeted radioimmunotherapy (PRIT). In some embodiments, bispecific antibody agents (e.g., anti-CD33 and anti-Benzyl-DOTA agents) can be used in a first step of a multistep pretargeting, followed by blood clearance using Benzyl-DOTA (metal)-Dextran as clearing agent, with a third step introducing Benzyl-DOTA (metal)-conjugated therapeutics such as Benzyl-DOTA (metal)-radioactive metal, Benzyl-DOTA (metal)-nanoparticles, Benzyl-DOTA (metal-liposomes, Benzyl-DOTA (metal)-drugs, Benzyl-DOTA (metal)-DNA, Benzyl-DOTA (metal)-RNA, and Benzyl-DOTA (metal)-toxins. Since C825 has different affinities for each type of Benzyl-DOTA-metal complex, the affinity of the pretargeted C825 for the clearing agent and the Benzyl-DOTA-ligand can be precisely controlled. Exemplary Benzyl-DOTA scFv fusion polypeptide sequence and CD33 light chain anti-Benzyl-DOTA scFv fusion polypeptide sequence are provided below:

C825-VH-(G4S)6-VL

SEQ ID NO: 18

SHVKLQESGPGLVQPSQSLSLTCTVSGFSLTDYGVHWVRQSPGKGLE

WLGVIWSGGGTAYNTALISRLNIYRDNSKNQVFLEMNSLQAEDTAMY

YCARRGSYPYNYFDAWGCGTTVTVSSGGGGSGGGGSGGGGSGGGGS

GGGGSGGGGSQAVVIQESALTTPPGETVTLTCGSSTGAVTASNYANW

VQEKPDHCFTGLIGGHNNRPPGVPARFSGSLIGDKAALTIAGTQTEDE

AIYFCALWYSDHWVIGGGTRLTVLG (CD33-VL-CL-(G4S)3-mouse C825-VH-(G4S)6-VL)

SEQ ID NO: 19

MGWSCIILFLVATATGEIVLTQSPATLSVSLGERATISCRASESVDNYG

ISFMNWFQQKPGQPPRLLIYAASNQGSGVPARFSGSGPGTDFTLTISSM

EPEDFAMYFCQQSKEVPWTFGGGTKLEIKRTVAAPSVFIFPPSDEQLKS

GTASVVCLLNNFYPREAKVQWKVDNALQSGNSQESVTEQDSKDSTY

SLSSTLTLSKADYEKHKVYACEVTHQGLSSPVTKSFNRGECTSGGGGS

GGGGSGGGGSHVKLQESGPGLVQPSQSLSLTCTVSGFSLTDYGVHWV

RQSPGKGLEWLGVIWSGGGTAYNTALISRLNIYRDNSKNQVFLEMNS

LQAEDTAMYYCARRGSYPYNYFDAWGCGTTVTVSSGGGGSGGGGS

GGGGSGGGGSGGGGSGGGGSQAVVIQESALTTPPGETVTLTCGSSTG

AVTASNYANWVQEKPDHCFTGLIGGHNNRPPGVPARFSGSLIGDKAA

LTIAGTQTEDEAIYFCALWYSDHWVIGGGTRLTVLG

In some embodiments, a CD33-BsAb of the present disclosure includes a light chain fusion polypeptide, wherein the light chain fusion polypeptide includes a sequence that is at least about 50% (e.g., at least about 55%, 60%, 65%, 70%, 75%, 80%, 85%, 90%, 95%, 96%, 97%, 98%, or 99%) identical to SEQ ID NO: 18 or 19.

In some embodiments, multispecific antibody agents (e.g., bispecific antibody agents such as CD33-BsAb agents) comprise a variant Fc region, wherein said variant Fc region comprises at least one amino acid modification relative to a wild-type Fc region. In certain embodiments, Fc modifications may include, but are not limited to modifications that alter effector function. In some embodiments, Fc variants comprise one or more engineered glycoforms, i.e., a carbohydrate composition that is covalently attached to a molecule comprising an Fc region, wherein said carbohydrate composition differs chemically from that of a parent molecule comprising an Fc region. Exemplary CD33 heavy chains with variant Fc sequences are provided below:

CD33 heavy chains with Fc silencing using specific mutations (LALA)

SEQ ID NO: 20

MGWSCIILFLVATATGEVQLVQSGPEVVKPGASVKISCKASGYTFTDY

NMHWVRQAHGQSLEWIGYIYPYNGGTGYNQKFKSRATLTVDNSAST

AYMEVSSLRSEDTAVYYCARGRPAMDYWGQGTLVTVSSASTKGPSV

FPLAPSSKSTSGGTAALGCLVKDYFPEPVTVSWNSGALTSGVHTFPAV

LQSSGLYSLSSVVTVPSSSLGTQTYICNVNHKPSNTKVDKRVEPKSCD

KTHTCPPCPAPEAAGGPSVFLFPPKPKDTLMISRTPEVTCVVVDVSHE

DPEVKFNWYVDGVEVHNAKTKPREEQYNSTYRVVSVLTVLHQDWL

NGKEYKCKVSNKALPAPIEKTISKAKGQPREPQVYTLPPSRDELTKNQ

VSLTCLVKGFYPSDIAVEWESNGQPENNYKTTPPVLDSDGSFFLYSKL

TVDKSRWQQGNVFSCSVMHEALHNHYTQKSLSLSPGK

CD33 heavy chains with Fc silencing using specific mutations (LALA + K322A)

SEQ ID NO: 21

MGWSCIILFLVATATGEVQLVQSGPEVVKPGASVKISCKASGYTFTDY

NMHWVRQAHGQSLEWIGYIYPYNGGTGYNQKFKSRATLTVDNSAST

```
AYMEVSSLRSEDTAVYYCARGRPAMDYWGQGTLVTVSSASTKGPSV

FPLAPSSKSTSGGTAALGCLVKDYFPEPVTVSWNSGALTSGVHTFPAV

LQSSGLYSLSSVVTVPSSSLGTQTYICNVNHKPSNTKVDKRVEPKSCD

KTHTCPPCPAPEAAGGPSVFLFPPKPKDTLMISRTPEVTCVVVDVSHE

DPEVKFNWYVDGVEVHNAKTKPREEQYNSTYRVVSVLTVLHQDWL

NGKEYKCAVSNKALPAPIEKTISKAKGQPREPQVYTLPPSRDELTKNQ

VSLTCLVKGFYPSDIAVEWESNGQPENNYKTTPPVLDSDGSFFLYSKL

TVDKSRWQQGNVFSCSVMHEALHNHYTQKSLSLSPGK

CD33 heavy chains with Fc silencing using
specific mutations (D265A)
                                      SEQ ID NO: 22
MGWSCIILFLVATATGEVQLVQSGPEVVKPGASVKISCKASGYTFTDY

NMHWVRQAHGQSLEWIGYIYPYNGGTGYNQKFKSRATLTVDNSAST

AYMEVSSLRSEDTAVYYCARGRPAMDYWGQGTLVTVSSASTKGPSV

FPLAPSSKSTSGGTAALGCLVKDYFPEPVTVSWNSGALTSGVHTFPAV

LQSSGLYSLSSVVTVPSSSLGTQTYICNVNHKPSNTKVDKRVEPKSCD

KTHTCPPCPAPELLGGPSVFLFPPKPKDTLMISRTPEVTCVVVAVSHED

PEVKFNWYVDGVEVHNAKTKPREEQYNSTYRVVSVLTVLHQDWLN

GKEYKCKVSNKALPAPIEKTISKAKGQPREPQVYTLPPSRDELTKNQV

SLTCLVKGFYPSDIAVEWESNGQPENNYKTTPPVLDSDGSFFLYSKLT

VDKSRWQQGNVFSCSVMHEALHNHYTQKSLSLSPGK
```

In some embodiments, multispecific antibody agents (e.g., bispecific antibody agents such as CD33-BsAb agents) have modified glycosylation sites, preferably without altering the functionality of the antibody, e.g., target binding activity. As used herein, "glycosylation sites" include any specific amino acid sequence in an antibody to which an oligosaccharide (i.e., carbohydrates containing two or more simple sugars linked together) will specifically and covalently attach. Oligosaccharide side chains are typically linked to the backbone of an antibody via either N- or O-linkages. N-linked glycosylation refers to the attachment of an oligosaccharide moiety to the side chain of an asparagine residue. O-linked glycosylation refers to the attachment of an oligosaccharide moiety to a hydroxyamino acid, e.g., serine, threonine. An Fc-glycoform, hu3F8-H1L1-IgG1n that lacked certain oligosaccharides including fucose and terminal N-acetylglucosamine was produced in particular CHO cells (and CHO variants including CHO-s, CHO-K1, etc.) and exhibited enhanced ADCC effector function.

In some embodiments, the present disclosure encompasses methods of modifying the carbohydrate content of an antibody of the disclosure by adding or deleting a glycosylation site. Methods for modifying the carbohydrate content of antibodies are well known in the art and encompassed within the disclosure, see, e.g., U.S. Pat. No. 6,218,149; EP 0 359 096 B1; U.S. Publication No. US 2002/0028486; WO 03/035835; U.S. Publication No. 2003/0115614; U.S. Pat. Nos. 6,218,149; 6,472,511; all of which are incorporated herein by reference in their entirety. In other embodiments, the present disclosure encompasses methods of modifying the carbohydrate content of an antibody of the present disclosure by deleting one or more endogenous carbohydrate moieties of the antibody. In a specific embodiment, the present disclosure encompasses deleting the glycosylation site of the Fc region of an antibody, by modifying position 297 from asparagine to alanine. In some embodiments, a multispecific antibody agent (e.g., a CD33-BsAb agent) comprises N297A mutation in the CH2 domain. In some embodiments, the N297A mutation results in aglycosylation, which reduces FcR or C1q binding. In some embodiments, an antibody agent comprises a heavy chain comprising an Fc region comprising a N297A mutation and a K322A mutation. In some embodiments, an antibody agent comprises a heavy chain comprising an Fc region comprising a N297A mutation and a D265A mutation. In some embodiments, an antibody agent comprises a heavy chain comprising an Fc region comprising a N297A mutation, a D265A mutation, and a K322A mutation.

Engineered glycoforms may be useful for a variety of purposes, including but not limited to enhancing or reducing effector function. Engineered glycoforms may be generated by any method known to one skilled in the art, for example by using engineered or variant expression strains, by co-expression with one or more enzymes, for example DI N-acetylglucosaminyltransferase III (GnTI11), by expressing a molecule comprising an Fc region in various organisms or cell lines from various organisms, or by modifying carbohydrate(s) after the molecule comprising Fc region has been expressed. Methods for generating engineered glycoforms are known in the art, and include but are not limited to those described in Umana et al, 1999, Nat. Biotechnol 17:176-180; Davies et al., 20017 Biotechnol Bioeng 74:288-294; Shields et al, 2002, J Biol Chem 277:26733-26740; Shinkawa et al., 2003, J Biol Chem 278:3466-3473) U.S. Pat. No. 6,602,684; U.S. Ser. No. 10/277,370; U.S. Ser. No. 10/113,929; PCT WO 00/61739A1; PCT WO 01/292246A1; PCT WO 02/311140A1; PCT WO 02/30954A1; POTILLE-GENT™ technology (Biowa, Inc. Princeton, N.J.); GLY-COMAB™ glycosylation engineering technology (GLY-CART biotechnology AG, Zurich, Switzerland); each of which is incorporated herein by reference in its entirety. See, e.g., WO 00061739; EA01229125; US 20030115614; Okazaki et al., 2004, JMB, 336: 1239-49 each of which is incorporated herein by reference in its entirety.

Fragments of polypeptides of the present disclosure include proteolytic fragments, as well as deletion fragments, in addition to specific antibody fragments discussed elsewhere herein.

Variants of multispecific antibody agents useful in accordance with the present disclosure include polypeptides with altered amino acid sequences due to amino acid substitutions, deletions, or insertions. Variants may occur naturally or be non-naturally occurring. Non-naturally occurring variants may be produced using art-known mutagenesis techniques or unnatural amino acids. Variant polypeptides may comprise conservative or non-conservative amino acid substitutions, deletions or additions.

Also included as "derivatives" are those polypeptides which contain one or more naturally occurring amino acid derivatives of the twenty standard amino acids. For example, 4-hydroxyproline may be substituted for proline; 5-hydroxylysine may be substituted for lysine; 3-methylhistidine may be substituted for histidine; homoserine may be substituted for serine; and ornithine may be substituted for lysine.

Amino acid sequences that are substantially the same as the sequences described herein include sequences comprising conservative amino acid substitutions, as well as amino acid deletions and/or insertions. A conservative amino acid substitution refers to the replacement of a first amino acid by a second amino acid that has chemical and/or physical properties (e.g., charge, structure, polarity, hydrophobicity/ hydrophilicity) that are similar to those of the first amino acid. Conservative substitutions include replacement of one amino acid by another within the following groups: lysine (K), arginine (R) and histidine (H); aspartate (D) and glutamate (E); asparagine (N), glutamine (Q), serine (S), threonine (T), tyrosine (Y), K, R, H, D and E; alanine (A), valine (V), leucine (L), isoleucine (I), proline (P), phenylalanine (F), tryptophan (W), methionine (M), cysteine (C) and glycine (G); F, W and Y; C, S and T.

Of course, the number of amino acid substitutions a skilled artisan would make depends on many factors, including those described above. Generally speaking, the number of amino acid substitutions, insertions or deletions for any given multispecific antibody agent will not be more than 40, 30, 20, 19, 18, 17, 16, 15, 14, 13, 12, 11, 10, 9, 8, 7, 6, 5, 4, 3, 2, 1, such as 1-30 or any range or value therein, as specified herein.

Amino acids in a multispecific antibody agent of the present disclosure that are essential for function can be identified by methods known in the art, such as site-directed mutagenesis or alanine-scanning mutagenesis (e.g., Ausubel, supra, Chapters 8, 15; Cunningham and Wells, Science 244:1081-1085 (1989)). The latter procedure introduces single alanine mutations at every residue in the molecule. The resulting mutant molecules are then tested for biological activity, such as, but not limited to at least binding to CD33. Sites that are critical for antibody binding can also be identified by structural analysis such as crystallization, nuclear magnetic resonance or photoaffinity labeling (Smith, et al., J. Mol. Biol. 224:899-904 (1992) and de Vos, et al., Science 255:306-312 (1992)).

In some embodiments, multispecific antibody agents as described herein, may be modified by the covalent attachment of an organic moiety. Such modification can produce an antibody agent with improved pharmacokinetic properties (e.g., increased in vivo serum half-life). An organic moiety can be a linear or branched hydrophilic polymeric group, fatty acid group, or fatty acid ester group. In particular embodiments, a hydrophilic polymeric group can have a molecular weight of about 800 to about 120,000 Daltons and can be a polyalkane glycol (e.g., polyethylene glycol (PEG), polypropylene glycol (PPG)), carbohydrate polymer, amino acid polymer or polyvinyl pyrolidone, and the fatty acid or fatty acid ester group can comprise from about eight to about forty carbon atoms.

Modified multispecific antibody agents can be prepared using suitable methods, such as by reaction with one or more modifying agents. A "modifying agent" as the term is used herein, refers to a suitable organic group (e.g., hydrophilic polymer, a fatty acid, a fatty acid ester) that comprises an activating group. An "activating group" is a chemical moiety or functional group that can, under appropriate conditions, react with a second chemical group thereby forming a covalent bond between the modifying agent and the second chemical group. For example, amine-reactive activating groups include electrophilic groups such as tosylate, mesylate, halo (chloro, bromo, fluoro, iodo), N-hydroxysuccinimidyl esters (NHS), and the like. Activating groups that can react with thiols include, for example, maleimide, iodoacetyl, acrylolyl, pyridyl disulfides, 5-thiol-2-nitrobenzoic acid thiol (TNB-thiol), and the like. An aldehyde functional group can be coupled to amine- or hydrazide-containing molecules, and an azide group can react with a trivalent phosphorous group to form phosphoramidate or phosphorimide linkages. Suitable methods to introduce activating groups into molecules are known in the art (see for example, Hernanson, G. T., Bioconjugate Techniques, Academic Press: San Diego, Calif. (1996)). An activating group can be bonded directly to the organic group (e.g., hydrophilic polymer, fatty acid, fatty acid ester), or through a linker moiety, for example a divalent C1-C12 group wherein one or more carbon atoms can be replaced by a heteroatom such as oxygen, nitrogen or sulfur. Suitable linker moieties include, for example, tetraethylene glycol, —(CH2)3-, —NH—, to name a few. Modifying agents that comprise a linker moiety can be produced, for example, by reacting a mono-Boc-alkyldiamine (e.g., mono-Boc-ethylenediamine, mono-Boc-diaminohexane) with a fatty acid in the presence of 1-ethyl-3-(3-dimethylaminopropyl) carbodiimide (EDC) to form an amide bond between the free amine and the fatty acid carboxylate. The Boc protecting group can be removed from the product by treatment with trifluoroacetic acid (TFA) to expose a primary amine that can be coupled to another carboxylate as described, or can be reacted with maleic anhydride and the resulting product cyclized to produce an activated maleimido derivative of the fatty acid. (See, for example, Thompson, et al., WO 92/16221 the entire teachings of which are incorporated herein by reference.)

In some embodiments, multispecific antibody agents (e.g., bispecific antibody agents, such as a CD33-BsAb) of the present disclosure are characterized by high affinity or avidity to an antigen (e.g. CD33). The affinity or avidity of a multispecific antibody agent for an antigen can be determined experimentally using any suitable method. (See, for example, Berzofsky, et al., "Antibody-Antigen Interactions," In Fundamental Immunology, Paul, W. E., Ed., Raven Press: New York, N.Y. (1984); Kuby, Janis Immunology, W. H. Freeman and Company: New York, N.Y. (1992); and methods described herein). The measured affinity of a particular antibody-antigen interaction can vary if measured under different conditions (e.g., salt concentration, pH). Thus, measurements of affinity and other antigen-binding parameters are preferably made with standardized solutions of multispecific antibody and antigen, and a standardized buffer, such as the buffer described herein.

In some embodiments, multispecific antibody agents (e.g., bispecific antibody agents, such as a CD33-BsAb) of the present disclosure are characterized by low toxicity. In some embodiments, a multispecific antibody agent is characterized by an ability to treat patients for extended periods with measurable alleviation of symptoms and low and/or acceptable toxicity. Low or acceptable immunogenicity and/or high affinity, as well as other suitable properties, can contribute to the therapeutic results achieved. "Low immunogenicity" is defined herein as raising significant HAHA, HACA or HAMA responses in less than about 75%, or preferably less than about 50% of the patients treated and/or raising low titres in the patient treated (Elliott et al., Lancet 344:1125-1127 (1994), entirely incorporated herein by reference).

Nucleic Acids

The disclosure provides polynucleotides comprising a nucleotide sequence encoding multispecific antibody agents (e.g., bispecific antibody agents, such as a CD33-BsAb) of the present disclosure and fragments thereof. Multispecific antibody agents (e.g., bispecific antibody agents, such as a CD33-BsAb) as described herein may be produced from nucleic acid molecules using molecular biological methods known to the art.

In some embodiments, nucleic acid constructs include regions that encode multispecific antibody agents (e.g., bispecific antibody agents, such as CD33-BsAb). In some embodiments, such multispecific antibody agents will include $V_H$ and/or $V_L$ regions. After identification and selection of antibodies exhibiting desired binding and/or functional properties, variable regions of each antibody are isolated, amplified, cloned and sequenced. Modifications may be made to the $V_H$ and $V_L$ nucleotide sequences, including additions of nucleotide sequences encoding amino acids and/or carrying restriction sites, deletions of nucleotide sequences encoding amino acids, or substitutions of nucleotide sequences encoding amino acids. The antibodies and/or antibody components may be generated from human, humanized or chimeric antibodies.

Where appropriate, nucleic acid sequences that encode multispecific antibody agents as described herein (e.g., bispecific antibody agents, such as CD33-BsAb) may be modified to include codons that are optimized for expression in a particular cell type or organism (e.g., see U.S. Pat. Nos. 5,670,356 and 5,874,304). Codon optimized sequences are synthetic sequences, and preferably encode the identical polypeptide (or a biologically active fragment of a full length polypeptide which has substantially the same activity as the full length polypeptide) encoded by the non-codon optimized parent polynucleotide. In some embodiments, the coding region of the genetic material encoding antibody components, in whole or in part, may include an altered sequence to optimize codon usage for a particular cell type (e.g., a eukaryotic or prokaryotic cell). For example, the coding sequence for a humanized heavy (or light) chain variable region as described herein may be optimized for expression in a bacterial cells. Alternatively, the coding sequence may be optimized for expression in a mammalian cell (e.g., a CHO cell). Such a sequence may be described as a codon-optimized sequence.

Nucleic acid constructs of the present disclosure may be inserted into an expression vector or viral vector by methods known to the art, and nucleic acid molecules may be operatively linked to an expression control sequence. A vector comprising any of the above-described nucleic acid molecules, or fragments thereof, is further provided by the present disclosure. Any of the above nucleic acid molecules, or fragments thereof, can be cloned into any suitable vector and can be used to transform or transfect any suitable host. The selection of vectors and methods to construct them are commonly known to persons of ordinary skill in the art and are described in general technical references (see, in general, "Recombinant DNA Part D," Methods in Enzymology, Vol. 153, Wu and Grossman, eds., Academic Press (1987)). Desirably, the vector comprises regulatory sequences, such as transcription and translation initiation and termination codons, which are specific to the type of host (e.g., bacterium, fungus, plant or animal) into which the vector is to be introduced, as appropriate and taking into consideration whether the vector is DNA or RNA. Preferably, the vector comprises regulatory sequences that are specific to the genus of the host. Most preferably, the vector comprises regulatory sequences that are specific to the species of the host.

In addition to the replication system and the inserted nucleic acid, the construct can include one or more marker genes, which allow for selection of transformed or transfected hosts. Marker genes include biocide resistance, e.g., resistance to antibiotics, heavy metals, etc., complementation in an auxotrophic host to provide prototrophy, and the like.

Suitable vectors include those designed for propagation and expansion or for expression or both. For example, a cloning vector is selected from the group consisting of the pUC series, the pBluescript series (Stratagene, LaJolla, Calif.), the pET series (Novagen, Madison, Wis.), the pGEX series (Pharmacia Biotech, Uppsala, Sweden), and the pEX series (Clontech, Palo Alto, Calif.). Bacteriophage vectors, such as λGT10, λGT11, λZapII (Stratagene), λEMBL4, and λNM1149, also can be used. Examples of plant expression vectors include pBI110, pBI101.2, pBI101.3, pBI121 and pBIN19 (Clontech). Examples of animal expression vectors include pEUK-C1, pMAM and pMAMneo (Clontech). The TOPO cloning system (Invitrogen, Carlsbad, Calif.) also can be used in accordance with the manufacturer's recommendations.

An expression vector can comprise a native or nonnative promoter operably linked to an isolated or purified nucleic acid molecule as described above. Selection of promoters, e.g., strong, weak, inducible, tissue-specific and developmental-specific, is within the skill in the art. Similarly, combining of a nucleic acid molecule, or fragment thereof, as described above with a promoter is also within the skill in the art.

Suitable viral vectors include, for example, retroviral vectors, parvovirus-based vectors, e.g., adeno-associated virus (AAV)-based vectors, AAV-adenoviral chimeric vectors, and adenovirus-based vectors, and lentiviral vectors, such as Herpes simplex (HSV)-based vectors. These viral vectors can be prepared using standard recombinant DNA techniques described in, for example, Sambrook et al., Molecular Cloning, a Laboratory Manual, 2d edition, Cold Spring Harbor Press, Cold Spring Harbor, N.Y. (1989); and Ausubel et al., Current Protocols in Molecular Biology, Greene Publishing Associates and John Wiley & Sons, New York, N.Y. (1994).

A retroviral vector is derived from a retrovirus. Retrovirus is an RNA virus capable of infecting a wide variety of host cells. Upon infection, the retroviral genome integrates into the genome of its host cell and is replicated along with host cell DNA, thereby constantly producing viral RNA and any nucleic acid sequence incorporated into the retroviral genome. As such, long-term expression of a therapeutic factor(s) is achievable when using retrovirus. Retroviruses contemplated for use in gene therapy are relatively non-pathogenic, although pathogenic retroviruses exist. When employing pathogenic retroviruses, e.g., human immunodeficiency virus (HIV) or human T-cell lymphotrophic viruses (HTLV), care must be taken in altering the viral genome to eliminate toxicity to the host. A retroviral vector additionally can be manipulated to render the virus replication-deficient. As such, retroviral vectors are considered particularly useful for stable gene transfer in vivo. Lentiviral vectors, such as HIV-based vectors, are exemplary of retroviral vectors used for gene delivery. Unlike other retroviruses, HIV-based vectors are known to incorporate their passenger genes into non-dividing cells and, therefore, can be of use in treating persistent forms of disease.

Additional sequences can be added to such cloning and/or expression sequences to optimize their function in cloning and/or expression, to aid in isolation of the polynucleotide, or to improve the introduction of the polynucleotide into a cell. Use of cloning vectors, expression vectors, adapters, and linkers is well known in the art. (See, e.g., Ausubel, supra; or Sambrook, supra).

In some embodiments, nucleic acids and vectors of the present disclosure may be isolated and/or purified. The present disclosure also provides a composition comprising an above-described isolated or purified nucleic acid molecule, optionally in the form of a vector. The composition can comprise other components as described further herein.

In some embodiments, nucleic acid molecules are inserted into a vector that is able to express a multispecific antibody agent (e.g., a bispecific antibody agent, such as a CD33-

BsAb) when introduced into an appropriate host cell. Appropriate host cells include, but are not limited to, bacterial, yeast, insect, and mammalian cells. Exemplary host cells include prokaryotes (e.g., E. coli) and eukaryotes (e.g., a COS or a CHO cell). Mammalian host cells that could be used include human Hela 293, H9 and Jurkat cells, mouse NIH3T3 and C127 cells, Cos 1, Cos 7 and CV 1, quail QC1-3 cells, mouse L cells and Chinese hamster ovary (CHO) cells (e.g., DG44 cells). Any method(s) known to one skilled in the art for the insertion of DNA fragments into a vector may be used to construct expression vectors encoding a multispecific antibody agent of the present disclosure (e.g., a bispecific antibody agent, such as a CD33-BsAb) under control of transcriptional/translational control signals. These methods may include in vitro recombinant DNA and synthetic techniques and in vivo recombination (See Sambrook et al. Molecular Cloning, A Laboratory Manual, Cold Spring Harbor Laboratory; Current Protocols in Molecular Biology, Eds. Ausubel, et al, Greene Publ. Assoc., Wiley-Interscience, NY).

Production of Antibody Agents

Multispecific antibody agents of the present disclosure (e.g., bispecific antibody agents, such as a CD33-BsAb) may be purified by any technique, which allows for the subsequent formation of a stable antibody agent. For example, not wishing to be bound by theory, a multispecific antibody agent (e.g., a bispecific antibody agent, such as a CD33-BsAb) can be recovered and purified from recombinant cell cultures by well-known methods including, but not limited to, protein A purification, protein G purification, ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. High performance liquid chromatography ("HPLC") can also be employed for purification. See, e.g., Colligan, Current Protocols in Immunology, or Current Protocols in Protein Science, John Wiley & Sons, NY, N.Y., (1997-2001), e.g., chapters 1, 4, 6, 8, 9, and 10, each entirely incorporated herein by reference.

Multispecific antibody agents of the present disclosure (e.g., bispecific antibody agents, such as CD33-BsAb) include naturally purified products, products of chemical synthetic procedures, and products produced by recombinant techniques from a eukaryotic host, including, for example, yeast, higher plant, insect and mammalian cells. Depending upon the host employed in a recombinant production procedure, antibody agents of the present disclosure can be glycosylated or can be non-glycosylated, with glycosylated preferred. Such methods are described in many standard laboratory manuals, such as Sambrook, supra, Sections 17.37-17.42; Ausubel, supra, Chapters 10, 12, 13, 16, 18 and 20, Colligan, Protein Science, supra, Chapters 12-14, all entirely incorporated herein by reference.

Purified multispecific antibody agents (e.g., bispecific antibody agents, such as CD33-BsAb) can be characterized by, for example, ELISA, ELISPOT, flow cytometry, immunocytology, BIACORE™ analysis, SAPIDYNE KINEXA™ kinetic exclusion assay, SDS-PAGE and Western blot, or by HPLC analysis as well as by a number of other functional assays disclosed herein. The contents of all cited references (including literature references, issued patents, published patent applications, and co-pending patent applications) cited throughout this application are hereby expressly incorporated by reference.

Antibody Agent Compositions

Compositions of the present disclosure (e.g., compositions that deliver a multispecific antibody agent such as a CD33-BsAb) may include any suitable and effective amount of a composition or pharmaceutical composition comprising at least one multispecific antibody agent (e.g., a CD33-BsAb), for use in delivering the provided multispecific antibody agent (e.g., a CD33-BsAb) to a cell, tissue, organ, animal or patient in need of such modulation, treatment or therapy.

Compositions of the present disclosure (e.g., compositions that deliver a multispecific binding agent such as a CD33-BsAb) can further comprise at least one of any suitable auxiliary, such as, but not limited to, diluent, binder, stabilizer, buffers, salts, lipophilic solvents, preservative, adjuvant or the like. Pharmaceutically acceptable auxiliaries are preferred. Non-limiting examples of, and methods of preparing such sterile solutions are well known in the art, such as, but limited to, Gennaro, Ed., Remington's Pharmaceutical Sciences, $18^{th}$ Edition, Mack Publishing Co. (Easton, Pa.) 1990. Pharmaceutically acceptable carriers can be routinely selected that are suitable for the mode of administration, solubility and/or stability of a multispecific antibody agent (e.g., a bispecific antibody agent, such as a CD33-BsAb), fragment or variant composition as well known in the art or as described herein.

Pharmaceutical excipients and additives useful in the present composition include but are not limited to proteins, peptides, amino acids, lipids, and carbohydrates (e.g., sugars, including monosaccharides, di-, tri-, tetra-, and oligosaccharides; derivatized sugars such as alditols, aldonic acids, esterified sugars and the like; and polysaccharides or sugar polymers), which can be present singly or in combination, comprising alone or in combination 1-99.99% by weight or volume. Exemplary protein excipients include serum albumin such as human serum albumin (HSA), recombinant human albumin (rHA), gelatin, casein, and the like. Representative amino acid/antibody components, which can also function in a buffering capacity, include alanine, glycine, arginine, betaine, histidine, glutamic acid, aspartic acid, cysteine, lysine, leucine, isoleucine, valine, methionine, phenylalanine, aspartame, and the like. One preferred amino acid is glycine.

Carbohydrate excipients suitable for use in the present disclosure include, for example, monosaccharides such as fructose, maltose, galactose, glucose, D-mannose, sorbose, and the like; disaccharides, such as lactose, sucrose, trehalose, cellobiose, and the like; polysaccharides, such as raffinose, melezitose, maltodextrins, dextrans, starches, and the like; and alditols, such as mannitol, xylitol, maltitol, lactitol, xylitol sorbitol (glucitol), myoinositol and the like. In certain embodiments, carbohydrate excipients for use in the present disclosure are mannitol, trehalose, and raffinose.

Compositions (e.g., compositions that deliver a multispecific antibody agent such as a CD33-BsAb) can also include a buffer or a pH adjusting agent; typically, the buffer is a salt prepared from an organic acid or base. Representative buffers include organic acid salts such as salts of citric acid, ascorbic acid, gluconic acid, carbonic acid, tartaric acid, succinic acid, acetic acid, or phthalic acid; Tris, tromethamine hydrochloride, or phosphate buffers. Preferred buffers for use in the present compositions are organic acid salts such as citrate.

Additionally, compositions of the present disclosure (e.g., compositions that deliver a multispecific binding agent such as a CD33-BsAb) can include polymeric excipients/additives such as polyvinylpyrrolidones, ficolls (a polymeric sugar), dextrates (e.g., cyclodextrins, such as 2-hydroxypropyl-β-cyclodextrin), polyethylene glycols, flavoring agents, antimicrobial agents, sweeteners, antioxidants, antistatic agents, surfactants (e.g., polysorbates such as "TWEEN 20" and "TWEEN 80"), lipids (e.g., phospholipids, fatty acids), steroids (e.g., cholesterol), and chelating agents (e.g., EDTA).

These and additional known pharmaceutical excipients and/or additives suitable for use in compositions comprising a multispecific antibody agent (e.g., a CD33-BsAb agent), portions or variants thereof are known in the art, e.g., as listed in "Remington: The Science & Practice of Pharmacy", 19$^{th}$ ed., Williams & Williams, (1995), and in the "Physician's Desk Reference", 52$^{nd}$ ed., Medical Economics, Montvale, N.J. (1998), the disclosures of which are entirely incorporated herein by reference. Preferred carrier or excipient materials are carbohydrates (e.g., saccharides and alditols) and buffers (e.g., citrate) or polymeric agents.

In some embodiments, a composition comprising a multispecific antibody agent (e.g., a CD33-BsAb agent) is stably formulated. In some embodiments, a stable formulation of a multispecific antibody agent (e.g., a CD33-BsAb agent) may comprise a phosphate buffer with saline or a chosen salt, as well as preserved solutions and formulations containing a preservative as well as multi-use preserved formulations suitable for pharmaceutical or veterinary use. Preserved formulations contain at least one known preservative or optionally selected from the group consisting of at least one phenol, m-cresol, p-cresol, o-cresol, chlorocresol, benzyl alcohol, phenylmercuric nitrite, phenoxyethanol, formaldehyde, chlorobutanol, magnesium chloride (e.g., hexahydrate), alkylparaben (methyl, ethyl, propyl, butyl and the like), benzalkonium chloride, benzethonium chloride, sodium dehydroacetate and thimerosal, or mixtures thereof in an aqueous diluent. Any suitable concentration or mixture can be used as known in the art, such as 0.001-5%, or any range or value therein, such as, but not limited to 0.001, 0.003, 0.005, 0.009, 0.01, 0.02, 0.03, 0.05, 0.09, 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.3, 4.5, 4.6, 4.7, 4.8, 4.9, or any range or value therein. Non-limiting examples include, no preservative, 0.1-2% m-cresol (e.g., 0.2, 0.3. 0.4, 0.5, 0.9, 1.0%), 0.1-3% benzyl alcohol (e.g., 0.5, 0.9, 1.1, 1.5, 1.9, 2.0, 2.5%), 0.001-0.5% thimerosal (e.g., 0.005, 0.01), 0.001-2.0% phenol (e.g., 0.05, 0.25, 0.28, 0.5, 0.9, 1.0%), 0.0005-1.0% alkylparaben(s) (e.g., 0.00075, 0.0009, 0.001, 0.002, 0.005, 0.0075, 0.009, 0.01, 0.02, 0.05, 0.075, 0.09, 0.1, 0.2, 0.3, 0.5, 0.75, 0.9, 1.0%), and the like.

As noted above, in some embodiments the present disclosure provides an article of manufacture, comprising packaging material and at least one vial comprising a solution of at least one multispecific antibody agent (e.g., a CD33-BsAb agent) with appropriate buffers and/or preservatives, optionally in an aqueous diluent, wherein said packaging material comprises a label that indicates that such solution can be held over a period of 1, 2, 3, 4, 5, 6, 9, 12, 18, 20, 24, 30, 36, 40, 48, 54, 60, 66, 72 hours or greater. The present disclosure further provides an article of manufacture, comprising packaging material, a first vial comprising lyophilized at least one multispecific antibody agent (e.g., a CD33-BsAb agent), and a second vial comprising an aqueous diluent of prescribed buffer or preservative, wherein said packaging material comprises a label that provides instructions to reconstitute the at least one multispecific antibody agent (e.g., a CD33-BsAb agent) in the aqueous diluent to form a solution that can be held over a period of twenty-four hours or greater.

In some embodiments, an aqueous diluent further comprises a pharmaceutically acceptable preservative. In some embodiments, preservatives may be selected from the group consisting of phenol, m-cresol, p-cresol, o-cresol, chlorocresol, benzyl alcohol, alkylparaben (methyl, ethyl, propyl, butyl and the like), benzalkonium chloride, benzethonium chloride, sodium dehydroacetate and thimerosal, or mixtures thereof. The concentration of preservative used in the formulation is a concentration sufficient to yield an antimicrobial effect. Such concentrations are dependent on the preservative selected and are readily determined by the skilled artisan.

Other excipients, e.g. isotonicity agents, buffers, antioxidants, preservative enhancers, can be optionally added to the diluent. An isotonicity agent, such as glycerin, is commonly used at known concentrations. A physiologically tolerated buffer can be added to provide improved pH control. The formulations can cover a wide range of pHs, such as from about pH 4 to about pH 10, and preferred ranges from about pH 5 to about pH 9, and a most preferred range of about 6.0 to about 8.0. In some embodiments, formulations of the present disclosure have pH between about 6.8 and about 7.8. In some embodiments, buffers include phosphate buffers, such as sodium phosphate, particularly phosphate buffered saline (PBS).

Other additives, such as a pharmaceutically acceptable solubilizers like Tween 20 (polyoxyethylene (20) sorbitan monolaurate), Tween 40 (polyoxyethylene (20) sorbitan monopalmitate), Tween 80 (polyoxyethylene (20) sorbitan monooleate), Pluronic F68 (polyoxyethylene polyoxypropylene block copolymers), and PEG (polyethylene glycol) or non-ionic surfactants such as polysorbate 20 or 80 or poloxamer 184 or 188, PLURONIC® polyls, other block co-polymers, and chelators such as EDTA and EGTA can optionally be added to the formulations or compositions to reduce aggregation. These additives may be particularly useful if a pump or plastic container is used to administer the formulation. The presence of pharmaceutically acceptable surfactant may mitigate the propensity for protein (e.g. CD33-BsAb agent) in a composition to aggregate.

In some embodiments, formulations of the present disclosure can be prepared by a process that comprises mixing at least one multispecific antibody agent (e.g., a CD33-BsAb agent) and a preservative selected from the group consisting of phenol, m-cresol, p-cresol, o-cresol, chlorocresol, benzyl alcohol, alkylparaben, (methyl, ethyl, propyl, butyl and the like), benzalkonium chloride, benzethonium chloride, sodium dehydroacetate and thimerosal or mixtures thereof in an aqueous diluent. Mixing at least one multispecific antibody agent (e.g., a CD33-BsAb agent) and preservative in an aqueous diluent can be carried out using conventional dissolution and mixing procedures. In some embodiments, preparation of a suitable formulation may comprise, for example, combining a measured amount of at least one antibody agent (e.g., a CD33-BsAb agent) in buffered solution with a desired preservative in a buffered solution in quantities sufficient to provide the protein and preservative at the desired concentrations. Variations of this process would be recognized by one of ordinary skill in the art. For example, the order the components are added, whether additional additives are used, the temperature and pH at which the formulation is prepared, are all factors that can be optimized for the concentration and means of administration used.

In some embodiments, formulations are provided to patients as clear solutions or as dual vials comprising a vial of lyophilized at least one multispecific antibody agent (e.g., a CD33-BsAb agent) that is reconstituted with a second vial containing water, a preservative and/or excipients, such as a phosphate buffer and/or saline and a chosen salt, in an aqueous diluent.

In some embodiments, an article of manufacture, comprising a multispecific antibody agent (e.g., a CD33-BsAb agent) includes packaging material. In some embodiments, packaging material provides, in addition to the information required by the regulatory agencies, the conditions under which the product can be used. In some embodiments, packaging material provides instructions for reconstitution of a multispecific antibody agent (e.g., a CD33-BsAb agent).

In some embodiments, compositions are formulated for parenteral administration. In some embodiments, a multispecific antibody agent (e.g., a CD33-BsAb agent) is formulated as a solution, suspension, emulsion or lyophilized powder in association, or separately provided, with a pharmaceutically acceptable parenteral vehicle. Examples of such vehicles are water, saline, Ringer's solution, dextrose solution, and 1-10% human serum albumin. Liposomes and nonaqueous vehicles such as fixed oils can also be used. A vehicle or lyophilized powder can contain additives that maintain isotonicity (e.g., sodium chloride, mannitol) and chemical stability (e.g., buffers and preservatives). In some embodiments, a formulation is sterilized by known or suitable techniques.

The present disclosure also provides, among other things, technologies for characterizing multispecific antibody agents (e.g., bispecific antibody agents, such as CD33-BsAb) and/or compositions comprising said multispecific antibody agents. In some embodiments, multispecific antibody agents (e.g., bispecific antibody agents, such as CD33-BsAb) and/or compositions comprising said multispecific antibody agents are characterized by binding to AML cells (e.g., HL60). In some embodiments, multispecific antibody agents (e.g., bispecific antibody agents, such as CD33-BsAb) and/or compositions comprising said multispecific antibody agents are characterized by in vivo retention (e.g., an in vivo serum half life of at least 6 hours, 12 hours, 18 hours, 24 hours, 36 hours, 48 hours, 60 hours, 72 hours, or more). In some embodiments, multispecific antibody agents (e.g., bispecific antibody agents, such as CD33-BsAb) and/or compositions comprising said multispecific antibody agents are characterized by ELISA, immunohistochemistry, Biacore binding assays, mass spectrometry, isoelectric focusing (IEF) chromatography, western blot, etc.

Applications

The present disclosure provides technologies for modulating, treating, or diagnosing at least one CD33 related disease, in a cell, tissue, organ, animal, or patient, as known in the art or as described herein, using at least one multispecific antibody agent of the present disclosure (e.g., a CD33-BsAb).

Any of the multispecific antibody agents (e.g., CD33-BsAbs) provided herein may be used in therapeutic methods. For example, multispecific antibody agents (e.g., CD33-BsAbs) of the present disclosure can be used as immunotherapeutic agents, for example in the treatment of cancers.

The present disclosure includes methods for modulating, treating, or diagnosing at least one malignant disease in a cell, tissue, organ, animal or patient, including, but not limited to, at least one of: multiple myeloma, leukemia, acute leukemia, acute lymphoblastic leukemia (ALL) (including B-cell ALL and T-cell ALL), acute myeloid leukemia (AML), chromic myelocytic leukemia (CML), chronic lymphocytic leukemia (CLL), hairy cell leukemia, myelodysplastic syndrome (MDS), a lymphoma, Hodgkin's disease, a malignant lymphoma, non-hodgkin's lymphoma, Burkitt's lymphoma, multiple myeloma, Kaposi's sarcoma, colorectal carcinoma, renal cell carcinoma, pancreatic carcinoma, prostatic carcinoma, nasopharyngeal carcinoma, malignant histiocytosis, paraneoplastic syndrome/hypercalcemia of malignancy, solid tumors, adenocarcinomas, sarcomas, malignant melanoma, hemangioma, metastatic disease, cancer related bone resorption, cancer related bone pain; the suppression of cancer metastasis; the amelioration of cancer cachexia; and the treatment of inflammatory diseases such as mesangial proliferative glomerulonephritis and the like. In some certain embodiments, provided compositions and methods can be used to treat extramedullary (EM) manifestations of leukemia. Such methods can optionally be used in combination with, by administering before, concurrently or after administration of such multispecific antibody agents (e.g., CD33-BsAbs), radiation therapy, an anti-angiogenic agent, a chemotherapeutic agent, a farnesyl transferase inhibitor or the like.

For use in therapeutic methods, multispecific antibody agents (e.g., CD33-BsAbs) of the present disclosure would be formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners.

In some embodiments, the present disclosure provides a method for treating a disease. In some embodiments, the method comprises administering to an individual having such disease a therapeutically effective amount of a multispecific antibody agent of the disclosure (e.g., a CD33-BsAbs). In some embodiments, a composition is administered to said individual, comprising a multispecific antibody agent of the present disclosure (e.g., a CD33-BsAbs) in a pharmaceutically acceptable form. In some embodiments, the disease to be treated is a proliferative disorder. In some embodiments, the disease is cancer. In some embodiments the method further comprises administering to the individual a therapeutically effective amount of at least one additional therapeutic agent, e.g., an anti-cancer agent if the disease to be treated is cancer. An "individual" may be a mammal, including a human.

In some embodiments, a multispecific antibody agent of the present disclosure (e.g., a CD33-BsAb) may be used in a method of diagnosing a medical condition characterized by CD33 expression in a subject.

Any of such methods can optionally comprise administering an effective amount of at least one composition or pharmaceutical composition comprising at least one multispecific antibody agent (e.g., a CD33-BsAb) to a cell, tissue, organ, animal or patient in need of such modulation, treatment, diagnosis, and/or therapy.

In some embodiments are provided are therapeutic methods comprising administering an effective amount of a composition that comprises and/or delivers a multispecific antibody agent (e.g., a bispecific antibody agent, such as a CD33-BsAb) to a subject that has been administered or will be administered IL2, such that the subject receives both. In some embodiments are provided methods comprising administering a composition that comprises and/or delivers IL2 to a subject that has been administered or will be administered a multispecific antibody agent (e.g., a bispecific antibody agent, such as a CD33-BsAb), such that the subject receives both.

Any method of the present disclosure can comprise a method for treating a CD33-mediated disorder or a disorder characterized by CD33 expression, comprising administering an effective amount of a composition or pharmaceutical composition comprising at least one a multispecific antibody agent of the present disclosure (e.g., a CD33-BsAb) to a cell, tissue, organ, animal or patient in need of such modulation, treatment or therapy. Such a method can optionally further comprise co-administration or combination therapy for treating such immune diseases, wherein the administering of said at least one a multispecific antibody agent of the present disclosure (e.g., a CD33-BsAb), specified portion or variant thereof, further comprises administering, before concurrently, and/or after, at least one additional agent.

Any method of the present disclosure can comprise a method for diagnosing a disease or disorder characterized by CD33 expression, comprising administering an effective amount of a composition or pharmaceutical composition comprising at least one a multispecific antibody agent of the present disclosure (e.g., a CD33-BsAb) to a cell, tissue, organ, animal, or patient.

T Cell-Based Therapies

Methods for destruction of tumor cells include inducing an immune response that selectively targets immune effector cells such as natural killer (NK) cells or cytotoxic T lymphocytes (CTLs) attack and destroy tumor cells. CTLs constitute the most potent effector cells of the immune system, however they cannot be activated by the effector mechanism mediated by the Fc domain of conventional therapeutic antibodies.

In some embodiments, multispecific antibody agents of the disclosure (e.g., CD33-BsAbs) can bind with a first binding domain a surface antigen on target cells, and with a second binding domain to an activating, invariant component of the T cell receptor (TCR) complex, have become of interest in recent years. Without wishing to be bound by theory, it is envisioned that simultaneous binding of such an antibody agent to both of its targets will force a temporary interaction between target cell and T cell, causing activation of any cytotoxic T cell and subsequent lysis of the target cell. Hence, an immune response may be re-directed to the target cells and is independent of peptide antigen presentation by the target cell or the specificity of the T cell as would be relevant for normal MHC-restricted activation of CTLs. In some embodiments, multispecific antibody agents of the disclosure (e.g., CD33-BsAbs) activate T cells present in a patient.

CTLs are ideal effectors for targeting tumors because they can traffic to the tumor sites where they can proliferate and release cytokines with subsequent recruitment of innate inflammatory or immune cells to trigger additional in vivo immune responses, including development of new clones of anti-tumor CTLs and B cells (in vivo vaccination effect), most evident from immune evaluations of adult patients receiving adoptive T cell therapies in the past. (Thakur A, et al., Cancer Immunol Immunother 60:1707-20, 2011). For example, following treatment with ATC armed with HER2-BsAb, a vaccination effect was detected against breast cancer and lymphoma in patients, including anti-breast cancer CTLs, anti-breast cancer antibodies, serum Th1 cytokine patterns, and IL-12 levels above the baseline. (Lum L G, et al., Bone Marrow Transplant 49:73-9, 2014; Lum L G, et al., Biol Blood Marrow Transplant 19:925-33, 2013; Grabert R C, et al., Clin Cancer Res 12:569-76, 2006).

BsAb Armed T Cells

In some embodiments are provided methods of activating and/or arming activated T cells (ATC) with multispecific antibody agents of the present disclosure (e.g., anti-CD3× anti-target antigen, including BsAb and BiTE antibody agents). Such armed ATC combine the targeting specificity of MoAb (e.g. huM195) with the non-MHC-restricted perforin/granzyme mediated cytotoxicity of T cells. BsAb or BiTE can arm ex vivo expanded activated T cells before infusion into a patient. This strategy converts every ATC into a specific CTL (Thakur and Lum, 2010, Curr Opin Mol Ther 12, 340-349; Grabert et al., 2006, Clin Cancer Res 12, 569-576).

Bispecific antibody agents permit the targeted engagement of T-cells and exploitation of their effector functions through HLA-non-restricted CD3-mediated activation rather than their antigen-specific HLA-restricted TCRs. Studies of certain bifunctional monoclonal antibodies specific for CD3 and a tumor antigen such as CD-19, HER-2 NEU, or CEA have demonstrated the capacity of these antibodies to link cytotoxic T-cells to tumor cells expressing the other targeted antigen (Bargou et al., 2008, Science 321, 974-977; Topp et al., 2009, Blood (ASH Annual Meeting Abstracts) 114, 840; Kiewe et al., 2006, Clin Cancer Res 12, 3085-3091; Lutterbuese et al., 2009, J Immnother 32, 341-352). Once both antibody receptors are engaged, a cytotoxic T-cell response is initiated against the tumor cells. The T-cell response involves formation of a cytotoxic synapse between the T-cell receptor and the tumor cell as well as perforin and granzyme mediated induction of tumor cell apoptosis (Offner et al., 2006, Mol Immunol 43, 763-771; Brischwein et al., 2006, Mol Immunol 43, 1129-1143). Engagement of CD3 also activates the T-cells, inducing proliferation and generation of effector cytokines that potentiate the antitumor effect (Brischwein et al., 2006, supra; Brischwein et al., 2007, J Immunother 30, 798-807). Strikingly, the activated T-cells upregulate an anti-apoptotic protein c-FLIP which protects them from the cytotoxic effects of TNF and Fas ligand generated during T-cell activation (Dreir et al., 2002, Int J Cancer 100, 690-697). As a result, the T-cell response is magnified. As a consequence, picogram levels of the bifunctional antibody can exert significant antitumor effects in vitro (Lutterbuese et al., 2009, supra; Brandl et al., 2007, Cancer Immunol Immunother 56, 1551-1563) and in vivo, as shown in preclinical animal models and particularly in the results of initial clinical trials of the CD3/CD19 bispecific in the treatment of B-cell lymphomas and ALL (Topp et al., 2009, supra; Kiewe et al., 2006, supra). It has been hypothesized that the T-cell responses induced can also recruit naïve T-cells and stimulate the generation of tumor-specific T-cells at tumor sites (Koehne et al., 2002, Blood 99, 1730-1740). Bispecific antibody agents can also be used to retarget other effector cells besides T-lymphocytes. These effector cells include NK cells, B-lymphocytes, dendritic cells, monocytes, macrophages, neutrophils, mesenchymal stem cells, neural stem cells and other stem cells to cells, tissues or organs that express CD33. When the tissue is tumor, these effector cells can be exploited to kill or to deposit proteins (e.g. cytokines, antibodies, enzymes, or toxins), radioactive isotopes for diagnosis or for therapy. When the tissue is a normal organ, the effector cells can be similarly exploited to deliver proteins or isotopes for diagnosis or for therapy.

The present disclosure encompasses the recognition that particular multispecific antibody agents of the disclosure (e.g., a CD33-BsAbs) may be useful for arming activated T-cells (ATCs). In some embodiments, a multispecific antibody agent (e.g., CD33-BsAbs) for use in arming ATCs may further comprise a domain that binds to an epitope of a T-cell antigen. In some embodiments, a T-cell antigen is CD3. In some embodiments, a domain that binds an epitope of a T-cell antigen is a humanized OKT3 scFv.

In some embodiments are provided methods for producing an armed population T cells with a multispecific antibody agent of the present disclosure (e.g., a CD33-BsAb). Standard methods for arming T-cells known in the art may be used in the context of the present disclosure. Biological activity of a multispecific antibody agent of the disclosure (e.g., a CD33-BsAbs) can be measured by various assays known in the art. Biological activities may include, for example, induction of proliferation of T cells, induction of signaling in T cells, induction of expression of activation markers in T cells, induction of cytokine secretion by T cells, induction of lysis of target cells such as tumor cells, induction of tumor regression and/or the improvement of survival. In some embodiments, a population of T cells includes an arming dose of a multispecific antibody agent of the present disclosure (e.g., a CD33-BsAb) in a range of 0.001 ng to 100 ng per $10^6$ cytotoxic immune cells.

In some embodiments, are provided a composition comprising a population of T cells armed with a multispecific antibody agent of the present disclosure (e.g., a CD33-BsAb). Without wishing to be bound by theory, it is envisioned that administration of a multispecific antibody agent of the present disclosure in combination with administration of activated T cells (ATCs) may enhance therapeutic response. In some embodiments, multispecific antibody agents (e.g., a CD33-BsAb) of the disclosure is administered in combination with ATCs. In some embodiments, treatment with a multispecific antibody agent (e.g., a CD33-BsAb) includes administration of a composition that delivers a multispecific antibody agent (e.g., a CD33-BsAb) and administration of a composition that delivers ATCs.

PBMC-Based Therapies

In some embodiments, multispecific antibody agents (e.g., a CD33-BsAb) of the present disclosure is administered in combination with a preparation of peripheral blood mononuclear cells (PBMCs). In some embodiments, PBMCs are allogeneic. In some embodiments, PBMCs are syngeneic. In some embodiments, treatment with a multispecific antibody agent (e.g., a CD33-BsAb) includes administration of a composition that delivers a multispecific antibody agent (e.g., a CD33-BsAb) and administration of a composition that delivers PBMCs.

CD33-Chimeric Antigen Receptor (CAR) Modified T Cells

The advent of chimeric antigen receptor technology (Sadelain M, et al., Cancer Discov 3:388-98, 2013) is rapidly expanding the therapeutic investigations of anti-CD33 redirected gene-modified T cells. At least three clinical trials are currently investigating the therapeutic potential of CD33-Targeted CAR-T: NCT02958397 (myeloid malignancies), NCT02944162 (AML), NCT01864902 (AML). However, a number of concerns are associated with CAR-T therapies. For example, for a HER-2 CAR-T therapy, toxicity from off target effects was initially observed. (Morgan R A, et al., Mol Ther 18:843-51, 2010). One consistent advantage with HER2-CAR modified T cells was that it was observed that it overcame the low levels of antigen expression. Osteosarcoma is a good example where the expression level has been controversial, (Thomas D G, et al., Clin Cancer Res 8:788-93, 2002) and CAR-modified T cells were found to be highly efficient against locoregional and metastatic xenografts, (Ahmed N, et al., Mol Ther 17:1779-87, 2009) and against osteosarcoma tumor initiating cells. (Rainusso N, et al., Cancer Gene Ther 19:212-7, 2012). Like in the case of BsAb-armed T cells, a cytoreductive high dose chemotherapy prior to T cell infusion is necessary for meaningful clinical responses to CAR-modified T cells.

While the use of cytoreduction definitely encourages engraftment and expansion of infused T cells, repeat cytoreduction in order to re-attempt T cell infusion is not feasible, and defeats the purpose of targeted therapy. Toxicity aside, cell harvest, processing, storage, transport and product release regulations for lymphocyte therapy remain a challenge both logistically and financially, especially when the cells have to be gene-modified. The current price tag of $20K per patient needs to be substantially reduced in order for this to be viable in the current drug market, in light of the shrinking budgets in healthcare. Even when cost is not the limiting factor, T cell survival and homing is suboptimal despite the infusion of billions of these cells. The cytolytic efficiency of BsAb-armed T cells is also not optimal given the turnover of the CD3 antigen on the T cell surface, continual shredding of the BsAb and exhaustion of T cells before seeing the tumor. Both BsAb-armed and CAR-modified T cells are no exceptions to the immunosuppressive tumor microenvironment, where Tregs, tumor associated macrophages and myeloid suppressor cells are in collusion to derail their anti-tumor properties. For chemically conjugated BsAb used in arming T cells, drug manufacture is a challenge because of product heterogeneity, aggregate formation and subsequent immunogenicity especially if mouse OKT3 is used. Furthermore, CAR modified T-cells are subject to the same immunosuppressive constrains that circulating T-cells, including anregy from PD-L1 expression, a limitation not found by BsAb.

However, to the extent that a CAR-T therapy is deemed useful and/or appropriate, it is envisioned that such a therapy could be augmented by multispecific antibody agents of the present disclosure (e.g., a CD33-BsAb, such as an anti-CD33 Ig anti-CD3 scFv agent).

In some embodiments, provided are chimeric antigen receptor (CAR) comprising a binding domain that comprises a multispecific antibody agent of the present disclosure (e.g., a bispecific antibody agent, such as a CD33-BsAb). In some embodiments, a CAR is a first generation, second generation or third generation CAR. In some embodiments, a CAR further comprises a transmembrane domain, a costimulatory signaling region, and a CD3 zeta signaling domain. In some embodiments, a CAR includes binding domain that comprises a CD33-bispecific antibody agent of the present disclosure, a transmembrane domain, a costimulatory signaling region, and a CD3 zeta signaling domain. Also provided herein are T cells that express a CAR of the present disclosure, i.e., a CAR-T cell. In some embodiments, provided are a population of CAR-T cells that express a CAR that includes a binding domain that comprises a multispecific antibody agent of the present disclosure (e.g., a bispecific antibody agent, such as a CD33-BsAb).

Other features of the invention will become apparent in the course of the following descriptions of exemplary embodiments which are given for illustration of the invention and are not intended to be limiting thereof.

EXAMPLES

The invention will be further illustrated by the following non-limiting examples. These Examples are set forth to aid in the understanding of the invention but are not intended to, and should not be construed to, limit its scope in any way. The Examples do not include detailed descriptions of conventional methods that would be well known to those of ordinary skill in the art (molecular cloning techniques, etc.). Unless indicated otherwise, parts are parts by weight, molecular weight is average molecular weight, temperature is indicated in Celsius, and pressure is at or near atmospheric.

Example 1—Construction of an Exemplary CD33-BsAb

This example describes the production of an exemplary bispecific antibody agent that has specificity for CD33 and CD3 and is in an IgG-scFv format. A humanized M195 monoclonal antibody was produced by grafting the CDRs of the heavy and light chains of M195 onto human IgG1 frameworks based on their homology with human frameworks IGHV1-3*01-IGHJ4*01 for VH, IGKV3D-11*02-IGKJ4*01 for VL, respectively. From two heavy chain and two light chain designs, four versions of huM195 were gene synthesized and expressed in DG44 cells. Exemplary heavy chain and light chain variable domain amino acid sequences include SEQ ID NOs: 1-2 and 3-4, respectively.

An exemplary CD33-BsAb (BiClone 133) antibody agent with a IgG-scFv format (FIG. 1A) was constructed. A humanized anti-CD33 heavy chain corresponding to SEQ ID NO: 9 and a humanized anti-CD33 light chain corresponding to SEQ ID NO: 10 were used in the construction of an exemplary CD33-BsAb agent. Exemplary CD33-BsAb agents can include a constant region comprising an hIgG1 Fc with N297A mutation. A N297A mutation is proposed to remove glycosylation of the Fc region. DNA and protein sequences for a heavy chain from an exemplary CD33-BsAb are provided below.

```
BiClone133 Heavy Chain DNA Sequence: (leader
sequence heavy chain underlined)
                                     SEQ ID NO: 23
ATGGGCTGGTCCTGCATCATCCTGTTTCTGGTGGCTACCGCCACCG

GCGAGGTGCAGCTGGTGCAGTCTGGACCCGAGGTCGTGAAGCCTG

GCGCCTCCGTGAAGATCTCCTGCAAGGCCTCCGGCTACACCTTCAC

CGACTACAACATGCACTGGGTGCGACAGGCCCACGGCCAGTCCCT

GGAATGGATCGGCTACATCTACCCCTACAACGGCGGCACCGGCTA

CAACCAGAAGTTCAAGTCTCGGGCCACCCTGACCGTGGACAACTCT

GCCTCTACCGCCTACATGGAAGTGTCCTCCCTGAGATCCGAGGACA

CCGCCGTGTACTACTGCGCCAGAGGCAGACCCGCCATGGACTATTG

GGGCCAGGGCACCCTCGTGACCGTGTCTAGCGCTTCTACCAAGGGC

CCCTCTGTGTTTCCTCTGGCCCCCTCCAGCAAGTCCACCTCTGGTGG

AACAGCCGCCCTGGGCTGCCTCGTGAAGGACTACTTTCCCGAGCCC

GTGACCGTGTCCTGGAACTCTGGCGCTCTGACCTCTGGCGTGCACA

CCTTCCCTGCTGTGCTGCAGTCTAGCGGCCTGTACTCCCTGTCCTCC

GTCGTGACAGTGCCCTCCAGCTCTCTGGGCACCCAGACCTACATCT

GCAACGTGAACCACAAGCCCTCCAATACCAAGGTGGACAAGCGGG

TGGAACCCAAGTCCTGCGACAAGACCCACACCTGTCCCCCTTGTCC
```

```
TGCCCCTGAACTGCTGGGCGGACCTTCCGTGTTCCTGTTCCCCCCA

AAGCCCAAGGACACCCTGATGATCTCCCGGACCCCCGAAGTGACC

TGCGTGGTGGTGGATGTGTCCCACGAGGACCCTGAAGTGAAGTTCA

ATTGGTACGTGGACGGCGTGGAAGTGCACAACGCCAAGACCAAGC

CTAGAGAGGAACAGTACGCCTCCACCTACCGGGTGGTGTCCGTGCT

GACAGTGCTGCACCAGGACTGGCTGAACGGCAAAGAGTACAAGTG

CGCCGTGTCCAACAAGGCCCTGCCTGCCCCCATCGAAAAGACCATC

TCCAAGGCCAAGGGCCAGCCCCGGGAACCCCAGGTGTACACACTG

CCCCCTAGCAGGGACGAGCTGACCAAGAACCAGGTGTCCCTGACC

TGTCTCGTGAAAGGCTTCTACCCCTCCGATATCGCCGTGGAATGGG

AGTCCAACGGCCAGCCTGAGAACAACTACAAGACCACCCCCCCTG

TGCTGGACTCCGACGGCTCATTCTTCCTGTACAGCAAGCTGACCGT

GGACAAGTCCCGGTGGCAGCAGGGCAACGTGTTCTCCTGCTCCGTG

ATGCACGAGGCCCTGCACAACCACTACACCCAGAAGTCCCTGTCCC

TGAGCCCCGGCAAA

BiClone133 Heavy Chain Amino Acid Sequence:
(leader sequence heavy chain underlined)
                                     SEQ ID NO: 24
MGWSCIILFLVATATGEVQLVQSGPEVVKPGASVKISCKASGYTFTDY

NMHWVRQAHGQSLEWIGYIYPYNGGTGYNQKFKSRATLTVDNSAST

AYMEVSSLRSEDTAVYYCARGRPAMDYWGQGTLVTVSSASTKGPSV

FPLAPSSKSTSGGTAALGCLVKDYFPEPVTVSWNSGALTSGVHTFPAV

LQSSGLYSLSSVVTVPSSSLGTQTYICNVNHKPSNTKVDKRVEPKSCD

KTHTCPPCPAPELLGGPSVFLFPPKPKDTLMISRTPEVTCVVVDVSHED

PEVKFNWYVDGVEVHNAKTKPREEQYASTYRVVSVLTVLHQDWLN

GKEYKCAVSNKALPAPIEKTISKAKGQPREPQVYTLPPSRDELTKNQV

SLTCLVKGFYPSDIAVEWESNGQPENNYKTTPPVLDSDGSFFLYSKLT

VDKSRWQQGNVFSCSVMHEALHNHYTQKSLSLSPGK
```

An exemplary CD33-BsAb antibody agent was constructed that included a fusion polypeptide with a humanized anti-CD33 light chain that was extended to include a C-terminal Gly-Ser linker (e.g., $(G_4S)_3$) followed by scFv with affinity to a second moiety, for example CD3 by including humanized OKT3 scFv. DNA and protein sequences for a fusion polypeptide from an exemplary CD33-BsAb are provided below.

```
BiClone133 Light Chain DNA Sequence (leader
sequence light chain underlined)
                                     SEQ ID NO: 25
ATGGGCTGGTCCTGCATCATCCTGTTTCTGGTGGCTACCGCCACCG

GCGAGATCGTGCTGACTCAGTCTCCTGCCACCCTGTCCGTGTCCCT

GGGCGAGAGAGCCACCATCTCTTGCAGAGCCTCCGAGTCCGTGGA

CAACTACGGCATCTCCTTCATGAACTGGTTCCAGCAGAAGCCCGGC

CAGCCTCCTCGGCTGCTGATCTACGCCGCTTCCAATCAGGGCTCTG

GCGTGCCCGCTAGATTCTCCGGATCTGGCCCTGGCACCGACTTTAC

CCTGACCATCTCCTCCATGGAACCCGAGGACTTCGCCATGTACTTT
```

```
TGCCAGCAGTCCAAAGAGGTGCCCTGGACCTTTGGCGGAGGCACC

AAGCTGGAAATCAAGCGGACCGTGGCCGCTCCCTCCGTGTTCATCT

TCCCACCTTCCGACGAGCAGCTGAAGTCCGGCACCGCTTCTGTCGT

GTGCCTGCTGAACAACTTCTACCCCCGCGAGGCCAAGGTGCAGTG

GAAGGTGGACAACGCCCTGCAGTCCGGCAACTCCCAGGAATCCGT

GACCGAGCAGGACTCCAAGGACAGCACCTACTCCCTGTCCTCCACC

CTGACCCTGAGCAAGGCCGACTACGAGAAGCACAAGGTGTACGCC

TGCGAAGTGACCCACCAGGGCCTGTCTAGCCCCGTGACCAAGTCTT

TCAACCGGGGCGAGTGCACTAGTGGCGGCGGAGGATCTGGCGGAG

GTGGAAGCGGAGGGGGAGGATCTCAGGTGCAGCTGGTGCAGAGCG

GAGGCGGAGTGGTGCAGCCTGGCAGATCCCTGAGACTGTCCTGCA

AGGCCTCCGGCTACACCTTCACCCGGTACACCATGCACTGGGTGCG

ACAGGCCCCTGGCAAGTGCCTGGAATGGATCGGCTACATCAACCC

CTCCCGGGGCTACACCAACTACAACCAGAAGTTCAAGGACCGGTT

CACCATCTCCCGGGACAACTCCAAGAACACCGCCTTTCTGCAGATG

GACTCCCTGCGCCTGAGGATACCGGCGTGTACTTCTGCGCCCGGT

ACTACGACGACCACTACTCCCTGGACTACGGGGCCAGGGAACCC

CTGTGACAGTGTCATCTGGTGGCGAGGAAGTGGGGAGGCGGAT

CAGGTGGTGGTGGATCAGGCGGGGAGGTTCAGGGGGTGGCGGTT

CTGGGGGAGGGGGCTCTGATATTCAGATGACTCAGAGCCCTTCCAG

CCTGAGCGCCTCCGTGGGAGATCGCGTGACAATTACCTGCTCTGCC

TCCTCCTCCGTGTCTTACATGAATTGGTATCAGCAGACCCCTGGGA

AGGCTCCTAAGCGGTGGATCTACGACACCTCCAAGCTGGCCTCTGG

CGTGCCCAGCAGGTTTTCTGGCTCCGGCAGCGGCACAGATTATACC

TTCACCATCAGCTCCCTGCAGCCAGAAGATATCGCTACCTATTATT

GTCAGCAGTGGTCCTCCAACCCTTTCACCTTCGGCTGCGGCACAAA

GCTGCAGATCACAAGA

BiClone133 Light Chain Amino Acid Sequence
(leader sequence light chain underlined)
                                   SEQ ID NO: 26
MGWSCIILFLVATATGEIVLTQSPATLSVSLGERATISCRASESVDNYG

ISFMNWFQQKPGQPPRLLIYAASNQGSGVPARFSGSGPGTDFTLTISSM

EPEDFAMYFCQQSKEVPWTFGGGTKLEIKRTVAAPSVFIFPPSDEQLKS

GTASVVCLLNNFYPREAKVQWKVDNALQSGNSQESVTEQDSKDSTY

SLSSTLTLSKADYEKHKVYACEVTHQGLSSPVTKSFNRGECTSGGGGS

GGGGSGGGGSQVQLVQSGGGVVQPGRSLRLSCKASGYTFTRYTMHW

VRQAPGKCLEWIGYINPSRGYTNYNQKFKDRFTISRDNSKNTAFLQM

DSLRPEDTGVYFCARYYDDHYSLDYWGQGTPVTVSSGGGGSGGGGS

GGGGSGGGGSGGGGSGGGGSDIQMTQSPSSLSASVGDRVTITCSASSS

VSYMNWYQQTPGKAPKRWIYDTSKLASGVPSRFSGSGSGTDYTFTISS

LQPEDIATYYCQQWSSNPFTFGCGTKLQITR
```

DNA encoding both an exemplary heavy chain and exemplary fusion polypeptide was codon optimized and inserted into a mammalian expression vector, transfected into CHO-S cells, and stable clones of highest expression were selected. Supernatants were collected from shaker flasks and purified on protein-A affinity chromatography.

Figure 1B:
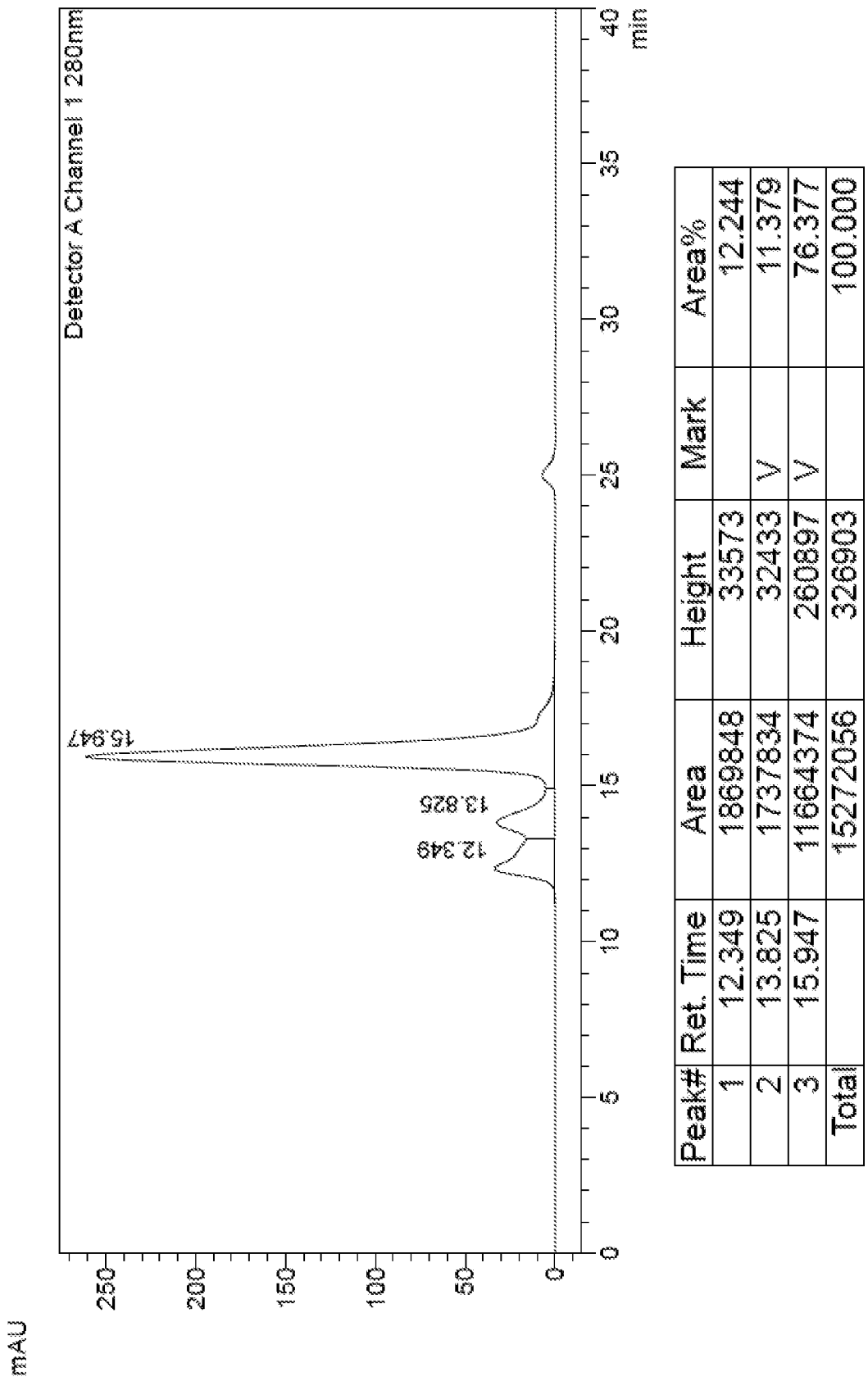
FIG. 1B illustrates purification of an exemplary CD33-CD3 bispecific antibody agent, depicted is a SE-HPLC chromatogram for a sample of a CD33-CD3 IgG-scFv, with the x-axis representing retention time in minutes and the y-axis representing absorbance at 280 nm in mAU.

Biochemical purity analysis of an exemplary CD33 BsAb was shown in FIG. 1B. An exemplary CD33 BsAb remained stable by SDS-PAGE and SEC-HPLC after multiple freeze and thaw cycles (data not shown).

Some advantages of an exemplary CD33-BsAb include:

Avoidance of trogocytosis and nonspecific retinculoendothelial removal: an exemplary CD33-BsAb is aglycosylated by point mutation in its Fc domain (N297A). Nonspecific binding to CD16 (FcγRIIA, FcγRIIB, and FcγRIIIA) are therefore abrogated. It is envisioned that this avoids CD3 trogocytosis which may be harmful for T cells. Without FcR binding, there is less competition for BsAb, and hence more quantitative delivery of BsAb to T cells and tumor cells. Together with K322A mutation, complement binding is also eliminated. With no binding to Fc and no complement activation, cytokine release syndrome will be substantially reduced.

Ease of affinity purification: an exemplary CD33-BsAb has intact affinity for protein A and protein G, hence ease of purification during manufacture.

Example 2—In Vitro Activity of an Exemplary CD33-BsAb

This example describes the in vitro activity of an exemplary CD33-BsAb in the IgG-scFv format. Specifically, this example describes the ability of an exemplary CD33-BsAb antibody agent to specifically bind CD33 expressing cells and to mediate cell-specific T cell killing.

CD33-BsAb (Biclone 133) Binding T Cells

Figure 2:
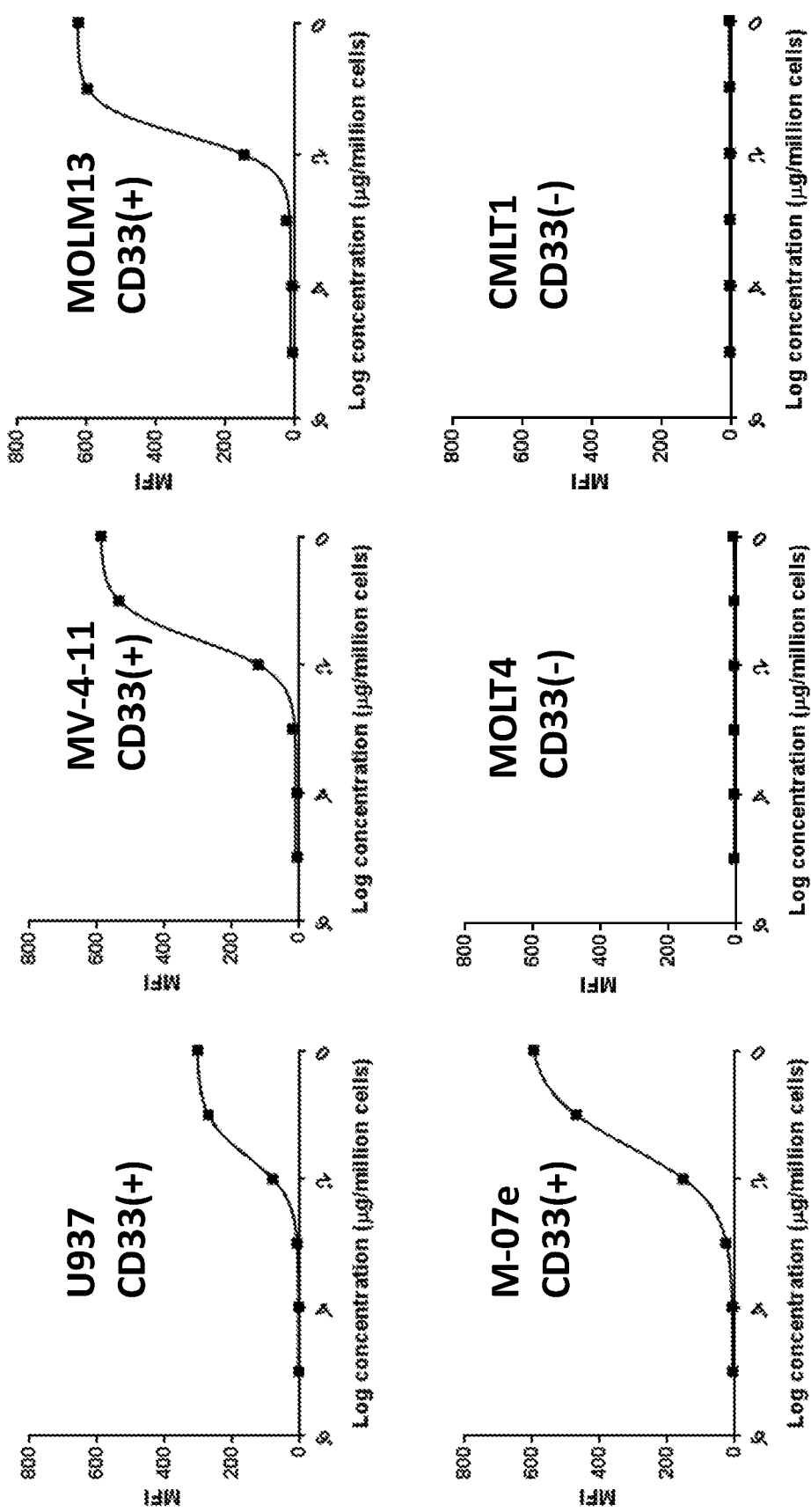
FIG. 2 depicts graphical results of FACS immunostaining of an exemplary CD33-CD3 IgG-scFv to target cells. The x-axis represents log concentration of antibody (μg antibody/million cells) and the y-axis represents MFI. Binding was observed on cells from numerous CD33(+) cell lines: U937, MV-4-11, MOLM13, M-07e, but binding was not observed on cell lines which do not express CD33, CD33(−), such as MOLT4 and CMLT1 cells.

Binding of an exemplary CD33-BsAb antibody agent to target cells tested by FACS immunostaining. CD33-BsAb (Biclone 133) bound to CD33(+) AML cell lines U937, MV-4-11, MOLM13, and M-07e while sparing CD33(−) leukemic cell lines MOLT4 and CMLT1 (FIG. 2).

CD33-BsAb Mediates Leukemia Antigen Specific T-Cell Cytotoxicity

Figure 3:
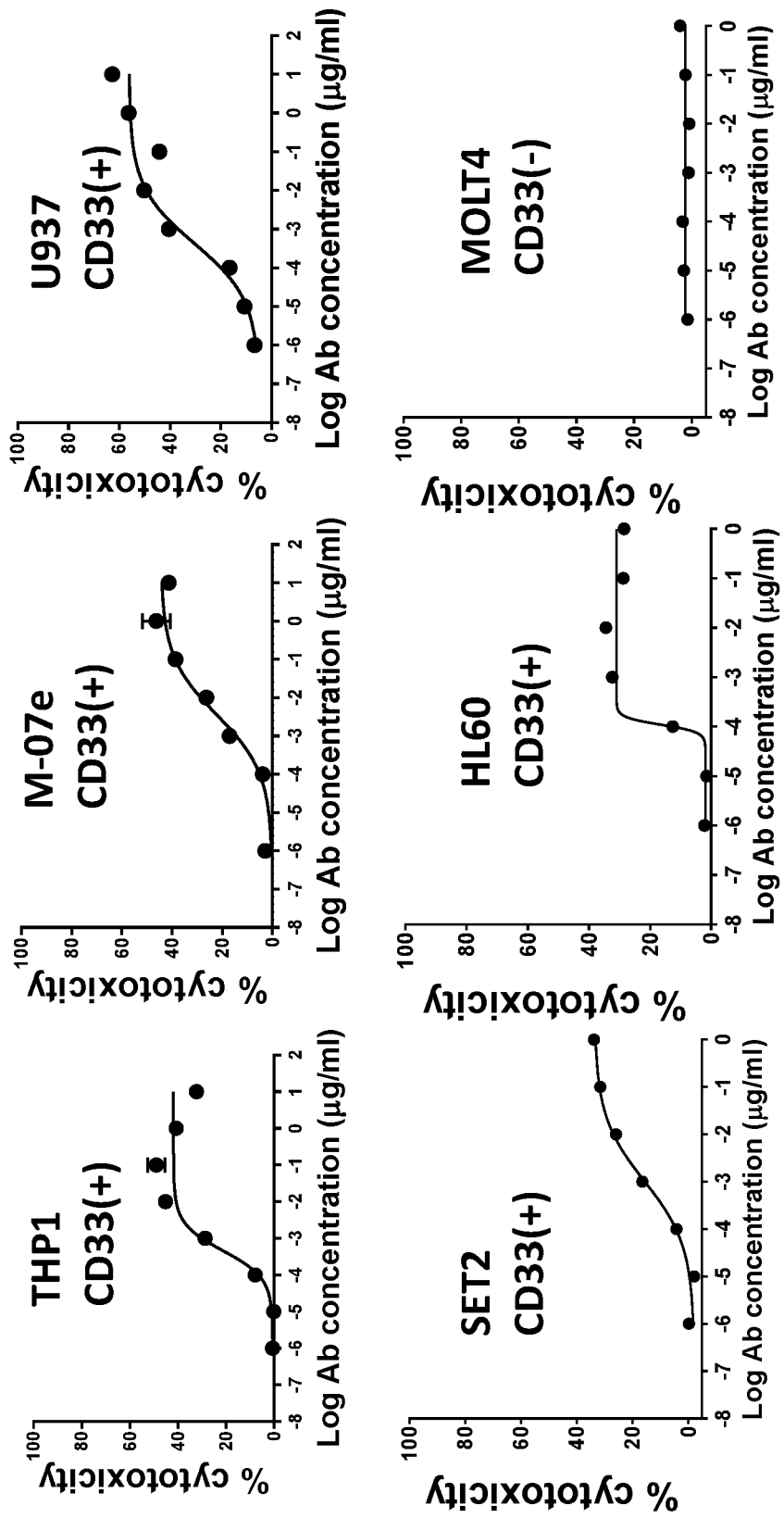
FIG. 3 depicts graphical results of T cell cytotoxicity assays with an exemplary CD33-CD3 IgG-scFv in various cell lines. AML cell lines were tested in a standard 4-hour $^{51}$CR release assay. The x-axis represents log concentration of antibody (μg antibody/ml) and the y-axis represents % cytotoxicity. Substantial killing was observed in numerous CD33(+) cell lines: THP1, M-07e, U937, SET2 and HL60, but CD33(−) MOLT4 cells were unaffected.

To evaluate whether an exemplary CD33-BsAb antibody agent could redirect T cells to kill leukemic cells, T cell cytotoxicity on CD33(+) AML cells was tested in a standard 4-hour $^{51}$Cr release assays. When CD33-BsAb (Biclone 133) was present, substantial killing of AML cell lines was observed with $EC_{50}$ of as low as 1.1 pM (for HL60 AML cells). CD33(−) leukemic cells were unaffected (FIG. 3).

Figure 4:
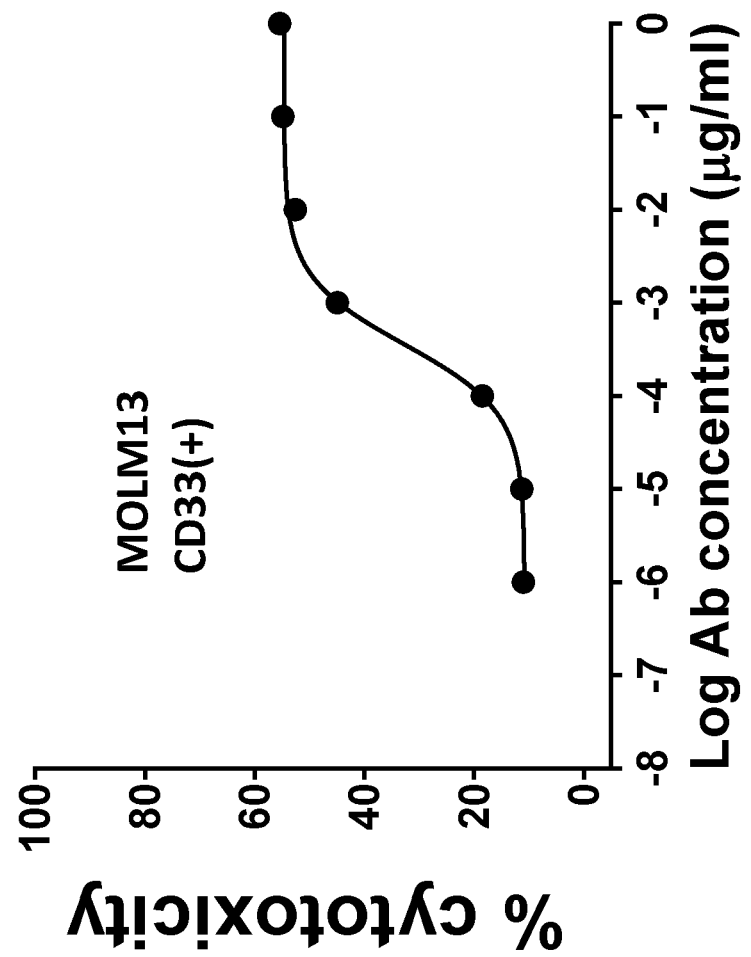
FIG. 4 depicts a graphical representation of T cell cytotoxicity with an exemplary CD33-CD3 IgG-scFv in a MOLM13 AML cell line. MOLM13 cells contain the FMS-like tyrosine kinase-3 (FLT3) internal tandem duplication (ITD) mutation (FLT3/ITD). The x-axis represents log concentration of antibody (μg antibody/ml) and the y-axis represents % cytotoxicity. Substantial killing was observed, with CD33-specific BsAb lysing MOLM13 cells with an $EC_{50}$ of 2.4 pM.

CD33-BsAb Redirected T Cell Killing of Human Leukemic Cell Lines with FLT3/ITD Mutation It is well documented that the prognosis of patients with the FMS-like tyrosine kinase-3 (FLT3) internal tandem duplication (ITD) mutations (FLT3/ITD) is poor. In pediatric AML, the negative consequences of these mutations are more prominent (Levis M, Leukemia 17:1738-52, 2003). To evaluate whether an exemplary CD33-BsAb antibody agent can redirect T cells to AMLs with FLT3/ITD mutations, MOLM13 AML cell line that contains this mutation was used. As shown in FIG. 4, CD33-specific BsAb lysed MOLM13 cells with EC50 of 2.4 pM.

Example 3—In Vivo Activity of an Exemplary CD33-BsAb

The example describes the in vivo activity of an exemplary CD33-BsAb in the IgG-scFv format. Specifically, this example describes the efficacy of an exemplary CD33-BsAb antibody agent in a xenograft model of AML.

Figure 5:
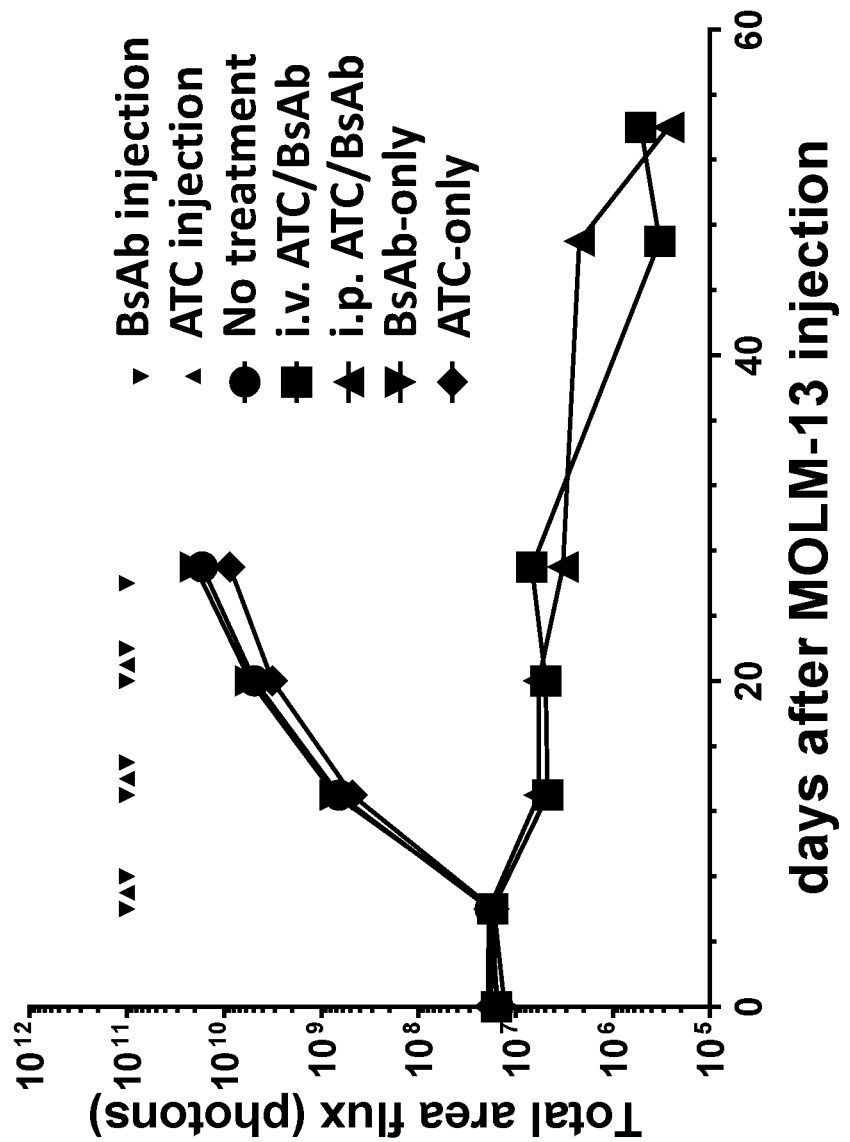
FIG. 5 depicts a graphical representation of in vivo efficacy of treatment with an exemplary CD33-CD3 IgG-scFv in a xenograft mouse model for AML. All mice received 1 million MOLM13 cells containing a firefly luciferase gene. The x-axis represents time after MOLM13 injection (in days) and the y-axis represents "total area flux" of luciferase gene expression as an indicator for MOLM13 cells burden. Downward facing triangles indicate timing of CD33-specific BsAb injections and upward triangles indicate timing of ATC injections.

Efficacy of CD33-BsAb Against Human AML Cells Containing the FLT3/ITD Mutations in Humanized Mice For in vivo therapy studies, NOD.Cg-Prkdc$^{scid}$ Il2rg$^{tm1Wjl}$ (NSG) mice were used. Mice were randomized in 5 groups and all received 1 million MOLM13 cells containing the firefly luciferase gene: 1. No treatment; 2. CD33-BsAb only; 3. Activated T cell (ATC) only; 4. ATC (iv, intravenous injection)/CD33-BsAb; and 5. ATC (ip, intraperitoneal injection)/CD33-BsAb. Treatment started at day 6, when the leukemia was established. For three weeks, mice received weakly injection of 10 million ATC. BsAb (100 ug/mouse) was administered one day before and one day after the T cell injection. To support T cell growth in vivo, 1000 IU of interleukin-2 was administered subcutaneously twice per week. Bioluminescence imaging was performed weekly to evaluate the leukemia burden. As shown in FIG. 5, administration of ATCs in the presence of the BsAb treated the leukemic mice. Both intraperitoneal and intravenous administration of ATCs was effective. Importantly, separate administration of ATCs or the BsAb failed to suppress tumor growth. When the tumor signal was no longer detectable by imaging, the mice were assessed by full necropsy. No remaining leukemic cells were detected.

Efficacy of CD33-BsAb Against Advanced Human AML in Humanized Mice

Figure 6:
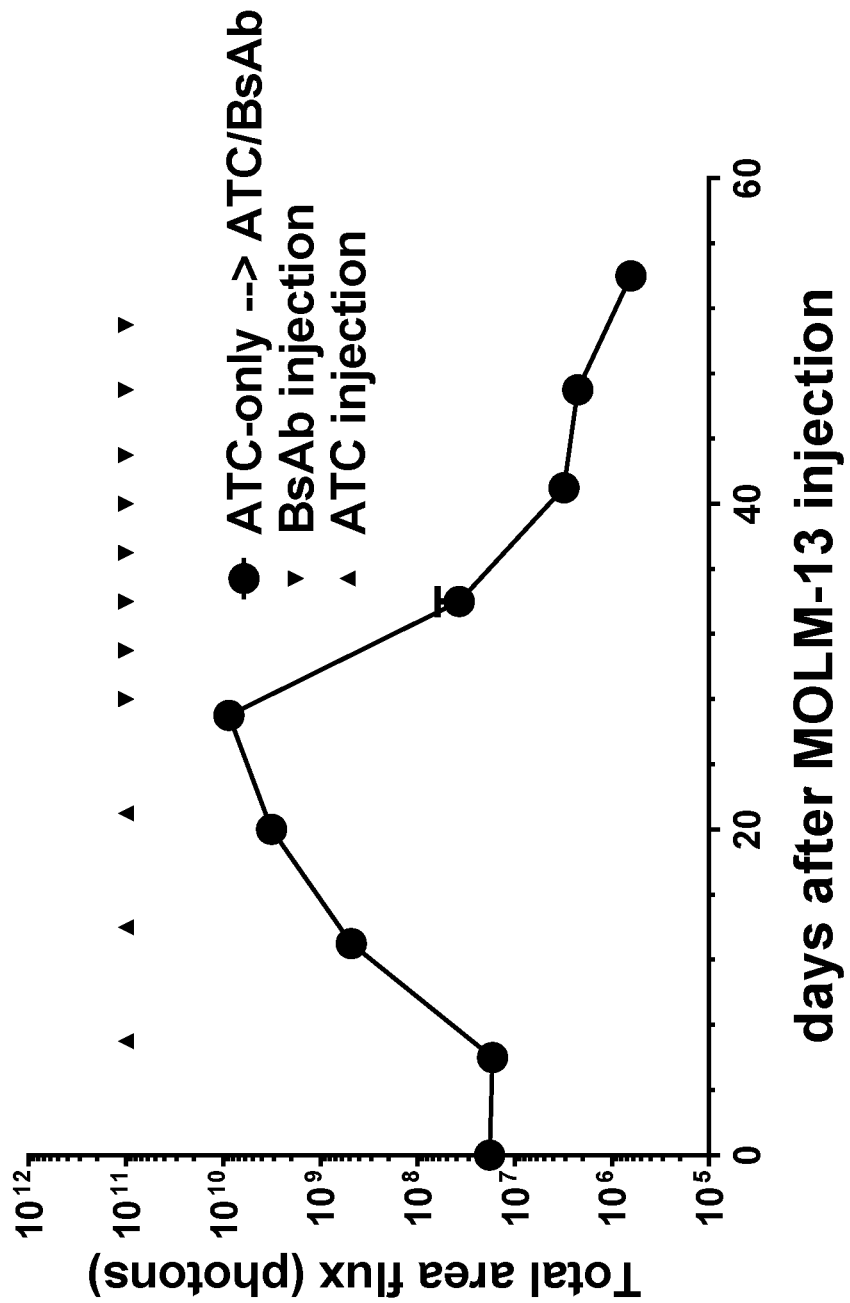
FIG. 6 depicts a graphical representation of in vivo efficacy of an exemplary CD33-CD3 IgG-scFv in a xenograft mouse model for advanced AML. Following inoculation with MOLM13 cells containing a firefly luciferase gene, mice were treated with weekly intravenous injections of 10 million human ATC for 3 weeks, followed by biweekly dosing of CD33-CD3 IgG-scFv for four weeks. The x-axis represents time after MOLM13 injection (in days) and the y-axis represents "total area flux" of luciferase gene expression as an indicator for MOLM13 cells burden. Downward facing triangles indicate timing of CD33-CD3 IgG-scFv injections and upward triangles indicate timing of ATC injections.

To investigate if the CD33-BsAb could treat advanced AML, NSG mice inoculated with 1 million MOLM13 leukemic cells. Starting from 7 days after leukemia injection, mice were treated with weekly injections of 10 million human ATC intravenously for 3 weeks. 28 days after leukemia injection, mice were treated with 2 injections of 100 ug/dose per week of the BsAb for four weeks. As shown in FIG. 6, leukemia was rapidly treated after administration of the BsAb.

Efficacy of Lower Doses of CD33-BsAb Against Human AML in Humanized Mice

Figure 7:
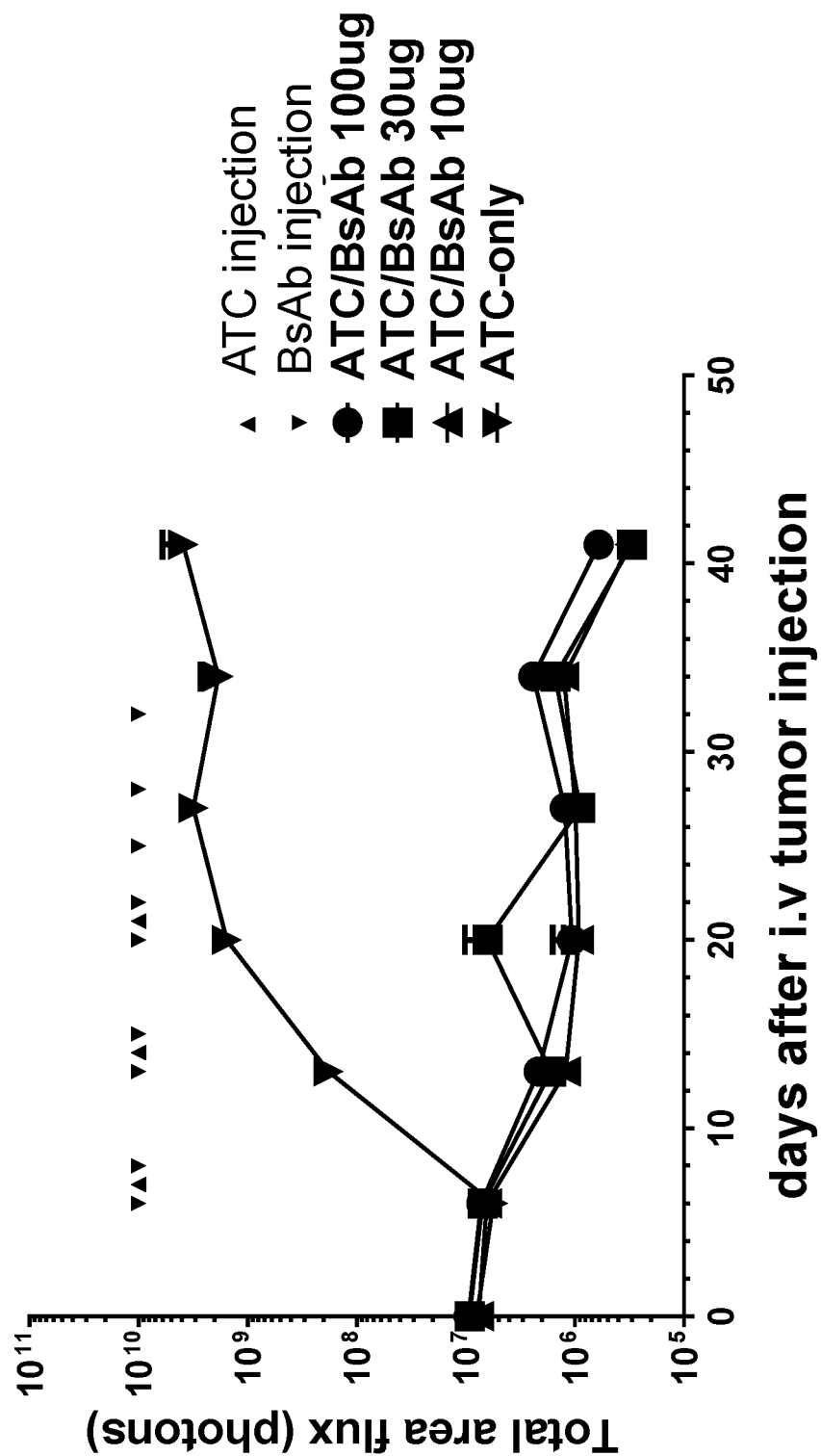
FIG. 7 depicts a graphical representation of in vivo efficacy of 3 different doses of an exemplary CD33-CD3 IgG-scFv in xenograft mouse model for AML. All mice received 1 million MOLM13 cells containing a firefly luciferase gene. Mice were treated with CD33-CD3 IgG-scFv at 100 μg, 30 μg and 10 μg. The x-axis represents time after MOLM13 injection (in days) and the y-axis represents "total area flux" of luciferase gene expression as an indicator for MOLM13 cells burden. Downward facing triangles indicate timing of CD33-CD3 IgG-scFv injections and upward triangles indicate timing of ATC injections.

To investigate the therapeutic effect of lower doses of the BsAb, NSG mice received 1 million MOLM13 AML cells. 6 days later, mice were randomized in 4 groups: 1. ATC only; 2. ATC/BsAb 100 μg/mouse; 3. ATC/BsAb 30 μg/mouse; and 4. ATC/BsAb 10 μg/mouse. ATC was injected intraperitoneally. To support T cell growth in vivo, 1000 IU of interleukin-2 was administered subcutaneously twice per week. Treatment started at day 6, when the leukemia was established. For three weeks, mice received weekly injections of 10 million ATC. BsAb (at different doses as mentioned above) was administered one day before and one day after the T cell injection. Bioluminescence imaging was performed weekly to evaluate the leukemia burden. As shown in FIG. 7, only mice who received both BsAb and ATC were treated, while leukemia grew in the ATC-only group. Importantly, even bug of the BsAb was as effective as 100 ug of the antibody.

Therefore, an exemplary CD33-BsAb demonstrated surprising efficacy in vivo. For example, an exemplary CD33-BsAb achieved cures in animals bearing human leukemic cell lines in vivo even when the leukemia burden was large. Moreover, PK of an exemplary CD33-BsAb is similar to that of IgG. This may permit lower treatment doses and less frequent injections (see, FIG. 7).

An Exemplary CD33-BsAb Against Human AML is Effective In Vivo at Very Low Doses

Figure 8A:
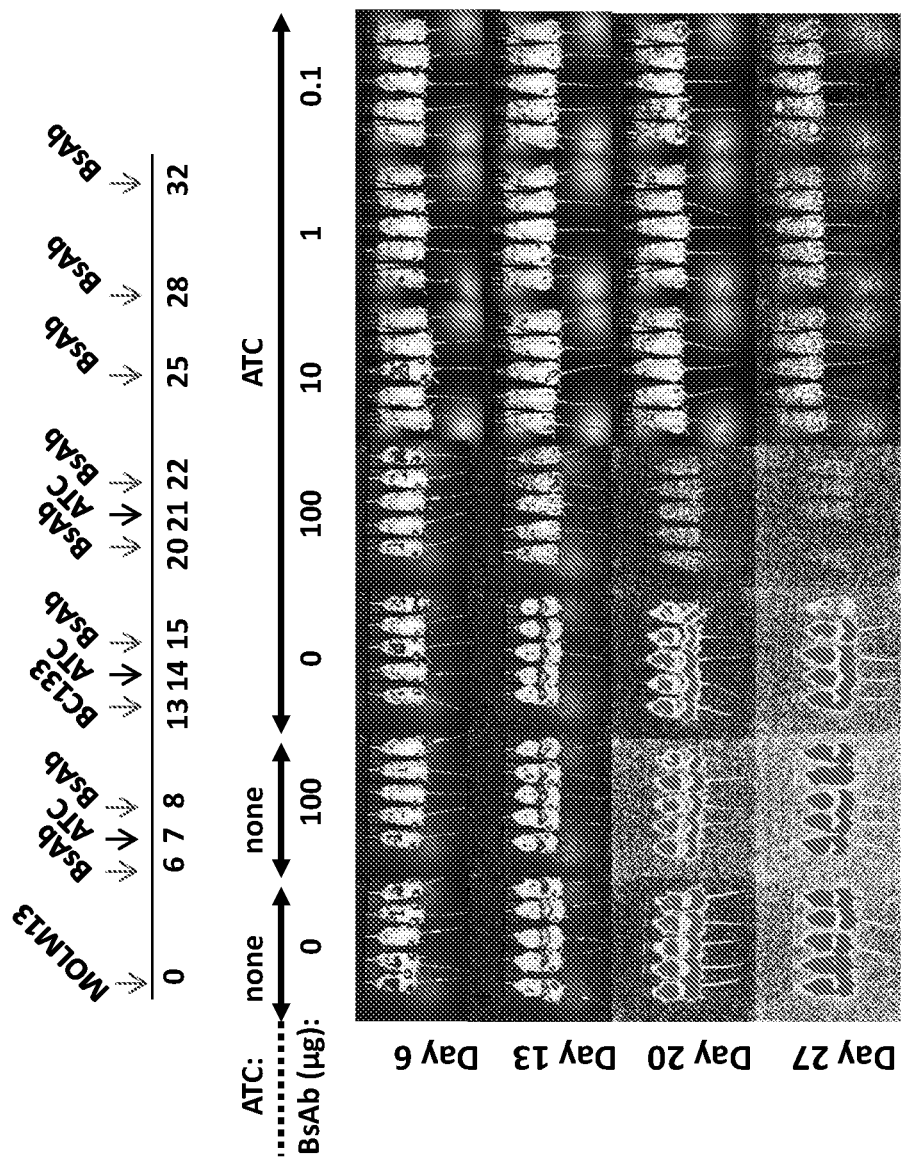
FIG. 8A and FIG. 8B depict in vivo potency of an exemplary CD33-CD3 IgG-scFv in T-cell mediated eradication of established in xenograft mouse model for human AML. Female NSG mice were implanted intravenously with 1 million MOLM13 AML cells. Tumor growth was monitored by bioluminescence imaging expressed as total flux in p/s. Starting 7 days after leukemia implantation, activated T cells (ATC, 5-10 million/dose) were injected once weekly for three weeks. The dose of exemplary CD33-CD3 IgG-scFv was titrated down (100 μg to 0.1 μg), administered one day before and one day after each T cell administration. To support T cell survival in vivo, 1000 IU IL2 was injected subcutaneously 2-3 time per week. Data from two independent experiments were pooled.
Figure 8B:
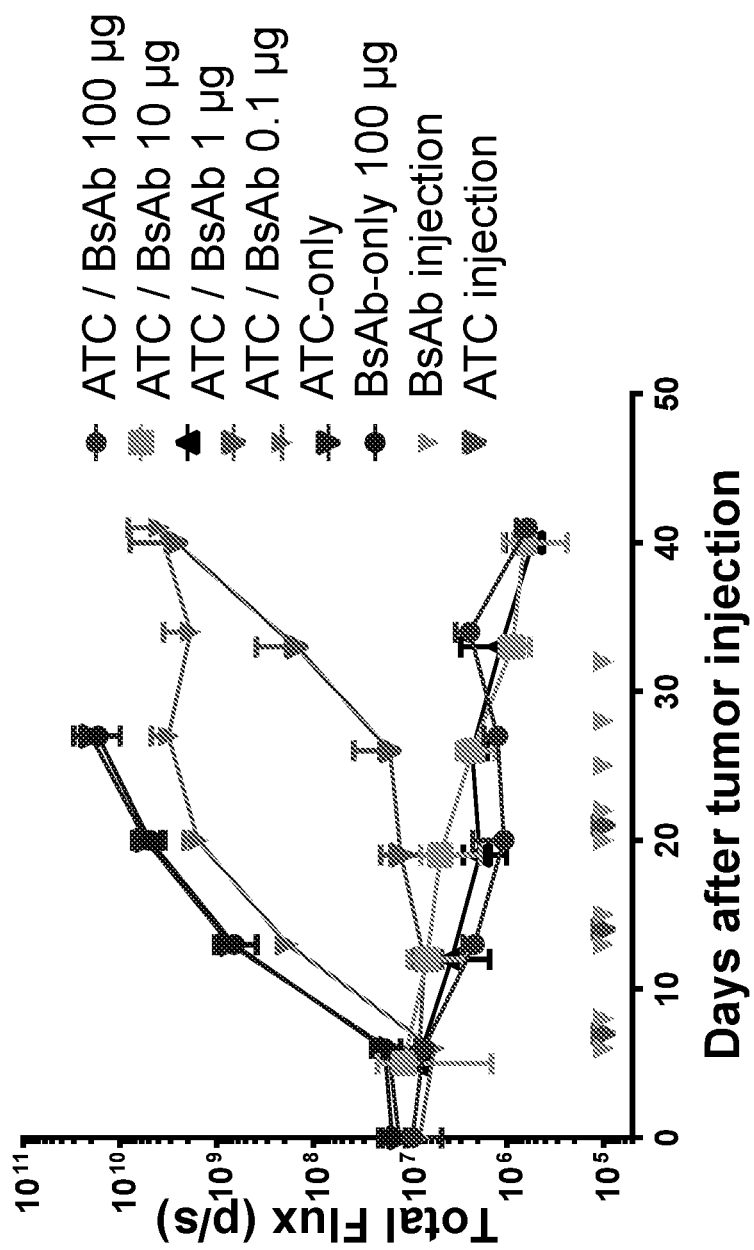

To test the in vivo potency of an exemplary CD33-BsAb antibody agent (CD33-CD3 IgG-scFv), xenografts in NSG mice were established by intravenous injection of luciferase (+) MOLM13 AML cells bearing fms-like tyrosine kinase internal tandem duplications (FLT3-ITD) mutations. Human peripheral blood T cells were activated with anti-CD3/CD28 coated microbeads for 7 days and injected once weekly for three weeks starting seven days after leukemia implantation. The dose of exemplary CD33-CD3 IgG-scFv, injected one day before and one day after each T cell administration, was titrated down from 100 μg per dose to 0.01 μg per dose. While injection of either exemplary CD33-CD3 IgG-scFv (BsAb) or T cells alone did not elicit a significant anti-tumor effect, all concentration tested of exemplary CD33-BsAb antibody agent (BsAb) in combination of human T cells inhibited leukemia growth, including the lowest concentration of 0.1 μg/dose BsAb with human T cells. Remarkably, a 1 μg/dose of BsAb was curative in the presence of human T cells (as were higher concentrations) (see, FIG. 8A and FIG. 8B). Thus, these data confirm that an exemplary CD33-BsAb antibody agent (CD33-CD3 IgG-scFv) administered in combination with T cells can effectively reduce cancer burden in vivo over a wide range of concentrations. While dosing is depicted using a mouse model, standard methods known to those of skill in the art can be used to scale animal studies to humans, for example, methods to calculate adjusted dose, etc.

Example 4—Tetravalency of CD33-BsAb Improves Potency

Figure 9:
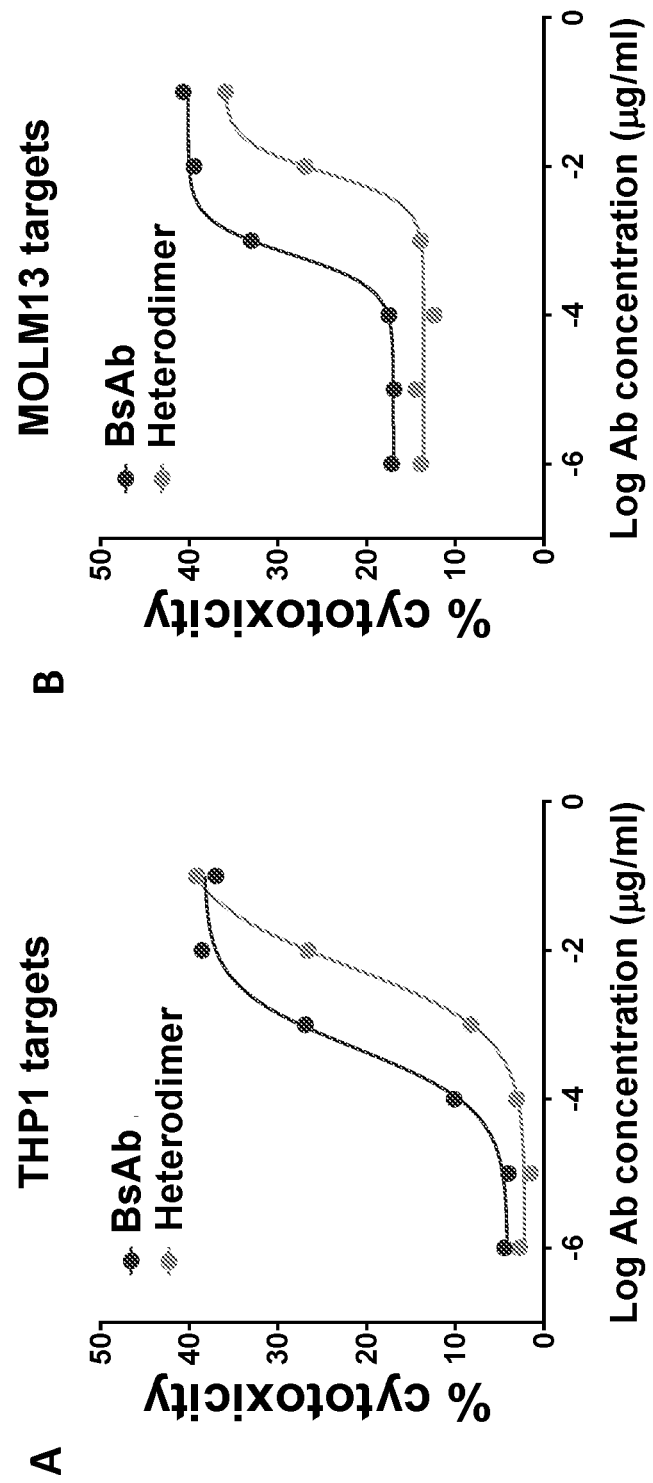
FIG. 9 depicts potency of a tetravalent exemplary CD33-CD3 IgG-scFv (BsAb) compared to a bivalent heterodimeric IgG platform (heterodimer) against human AML cells in vitro. TDCC in the presence of tetravalent CD33-CD3 IgG-scFv versus bivalent heterodimer against CD33(+) in human AML cell lines was assessed by a 4 h chromium release assay.
Figure 10:
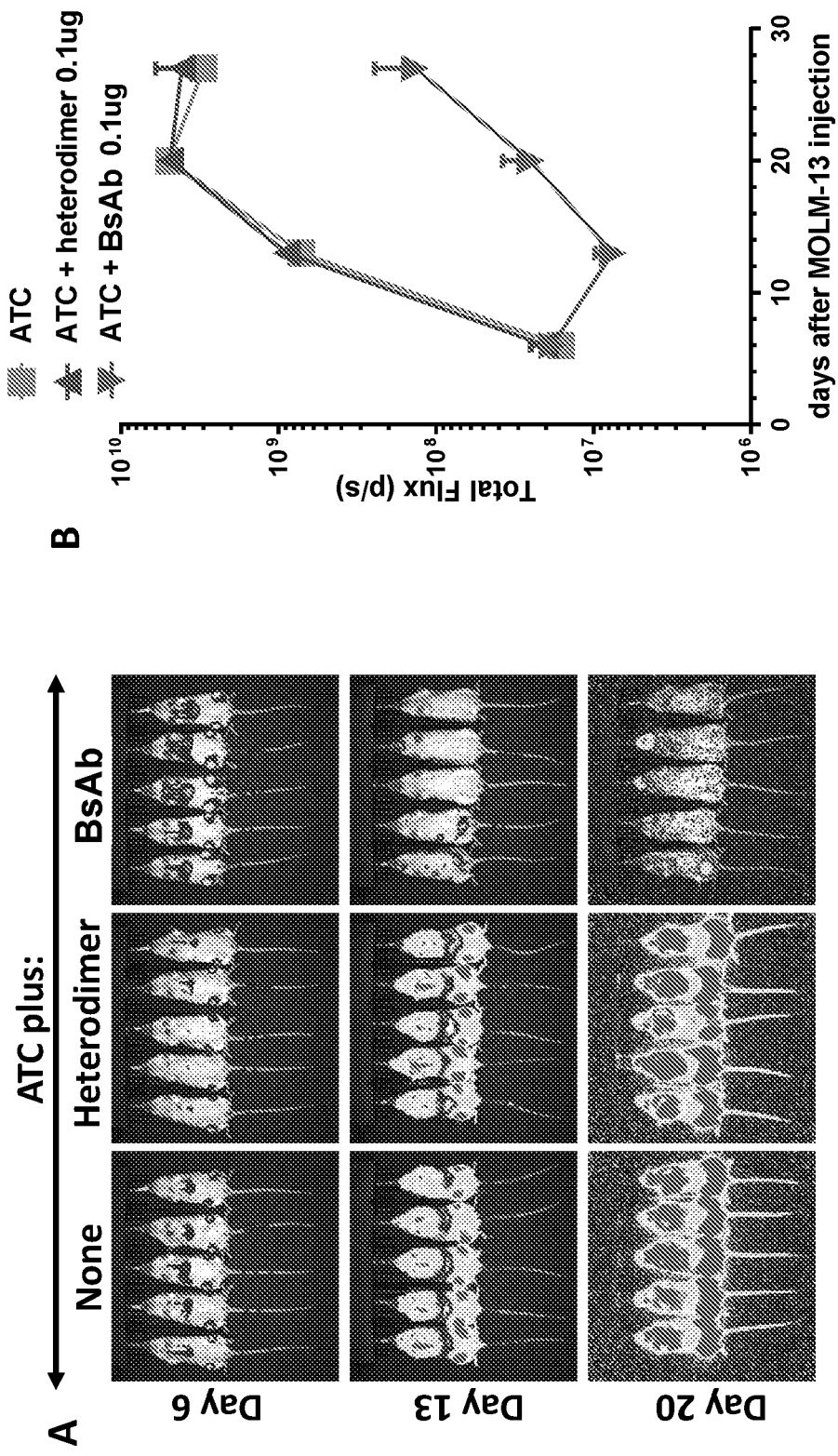
FIG. 10 depicts in vivo efficacy of a tetravalent exemplary CD33-CD3 IgG-scFv (BsAb) compared to a bivalent heterodimeric IgG platform (heterodimer). Female NSG mice were implanted intravenously with 1 million MOLM13 AML cells. Tumor growth was monitored by bioluminescence imaging and expressed as total flux in p/s. Activated T cells (ATC, 5-10 million/dose) were injected once weekly for three weeks starting seven days after leukemia implantation. exemplary CD33-CD3 IgG-scFv (BsAb) or the heterdimeric BsAb (each at 0.1 μg) were injected one day before and one day after each T cell administration. To support T cell persistence in vivo, 1000 IU IL2 was administered subcutaneously two times per week.

This example analyzes the effect of valency on potency of an exemplary bispecific antibody agent, CD33-CD3 IgG-scFv. While bispecific antibody platforms with different biologic properties have been designed, and some have even entered the clinic, there is a continuing need for effective T cell engaging therapeutics (Wu Z, Cheung N V. T cell engaging bispecific antibody (T-BsAb): from technology to therapeutics. Pharmacol Ther. 2017). However, unlike most bispecific antibody platforms, the present disclosure encompasses the recognition that a tetravalent (2+2) IgG(L)-scFv bispecific antibody may has beneficial characteristics. An exemplary CD33-CD3 IgG-scFv has two binding arms directed to CD33 on target cells and two directed to CD3 on T cells. To investigate the relevance of valency, a bivalent (1+1) IgG-based CD33-CD3 bispecific antibody agent ("heterodimer") was generated using a controlled Fab arm exchange method. (Labrijn A F, Meesters J I, Priem P, et al. Controlled Fab-arm exchange for the generation of stable bispecific IgG1. Nat Protoc. 2014; 9(10):2450-2463). ENREF 2 This CD33-CD3 heterodimer was composed of two half-IgG molecules against CD3 (huOKT3) and CD33 (huM195) that were preferentially paired to make an IgG heterodimer bispecific antibody. To compare the potency of an exemplary CD33-CD3 IgG-scFv (BsAb) and the heterodimer, THP1 and MOLM13 cells were used in a killing assay. As shown in FIG. 9, an exemplary CD33-CD3 IgG-scFv mediated TDCC of THP1 and MOLM13 AML cells 12-fold more potently than that mediated by the heterodimer. Next, an exemplary CD33-CD3 IgG-scFv (BsAb) and the corresponding heterodimer were compared in vivo. MOLM13 cells were implanted intravenously in NSG mice and on day six, treated with very low doses of BsAb (0.1 μg/mouse/dose) plus activated T cells. Tumor growth was monitored by bioluminescence (expressed as total flux in p/s). While the combination of T cells and the heterodimer was relatively ineffective in tumor suppression, being highly similar to the T cells alone group, the exemplary CD33-CD3 IgG-scFv (BsAb) plus T cells slowed down leukemia growth markedly (FIGS. 10, A and B). Collectively, these data support that a tetravalent IgG(L)-scFv has increased potency relative to a corresponding bivalent IgG heterodimer.

Example 5—Co-Administration of Exemplary CD33-BsAb with IL2 Improves Efficacy

Figure 11:
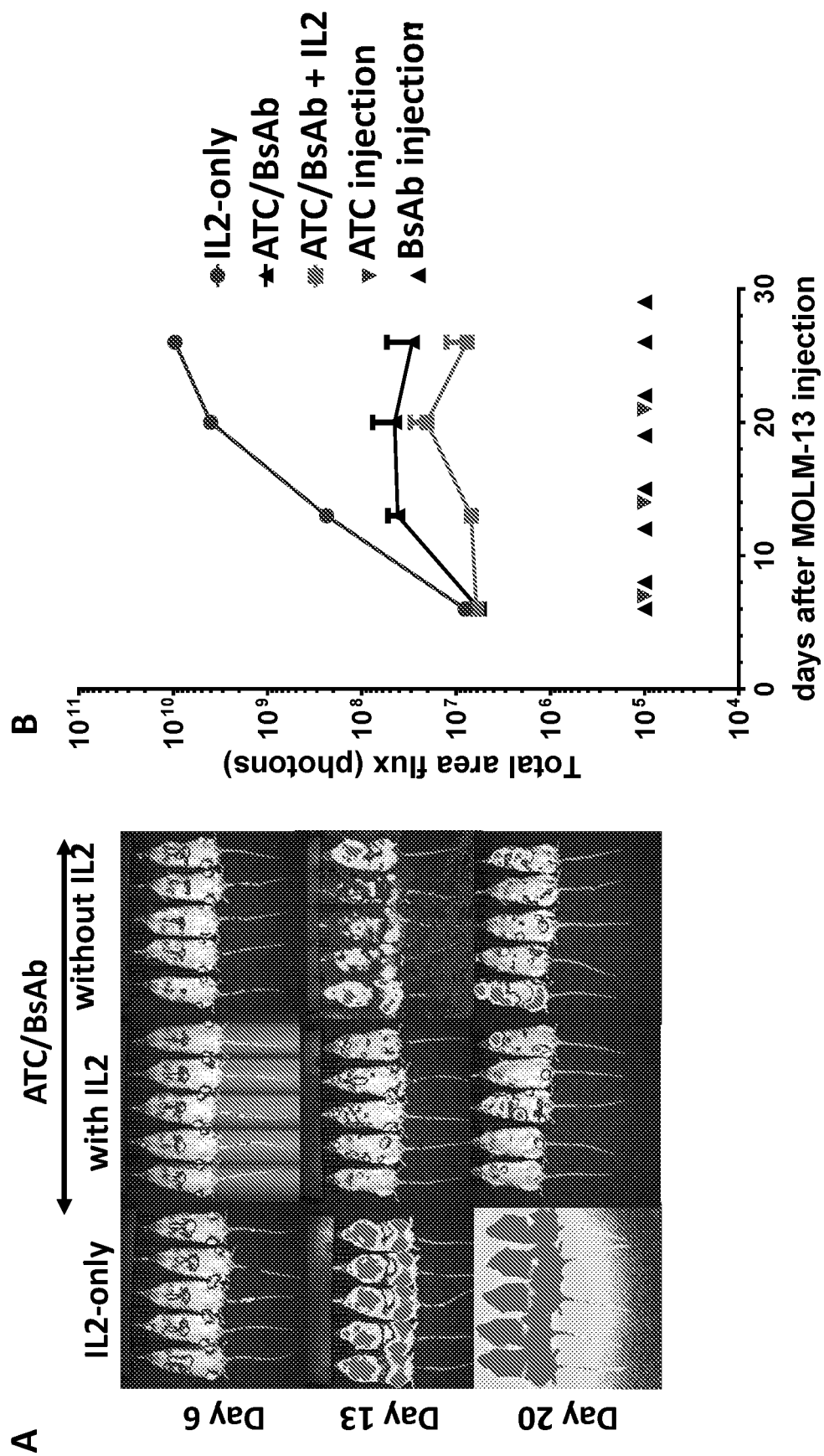
FIG. 11 depicts in vivo efficacy of combination treatment of IL2 and CD33-CD3 IgG-scFv (BsAb) redirected T cells. Female NSG mice were implanted intravenously with 1 million MOLM13 AML cells. Tumor growth was monitored by bioluminescence imaging expressed as total flux in p/s. Starting 7 days after leukemia implantation, activated T cells (ATC, 5-10 million/dose) were injected once weekly for three weeks. CD33-CD3 IgG-scFv (BsAb) (10 μg), administered one day before and one day after each T cell administration. One group of ATC/BsAb recipients were administered IL2 (1000 IU subcutaneously) 2-3 times per week while the "without IL2" group did not receive any IL2.

This example analyzes the effect of administering an exemplary bispecific antibody agent, CD33-CD3 IgG-scFv, in combination with the cytokine IL2. Since activated T cells were cultured in the presence of IL2, it was tested if further administration of IL2 after T cell administration improved efficacy. The results showed that T cells redirected via an exemplary CD33-CD3 IgG-scFv had improved anti-leukemic effect in the presence of IL2 suggesting a beneficial role of this cytokine for in vivo T cell function (FIG. 11).

Example 6—Efficacy of an Exemplary CD33-BsAb on Extramedullary Leukemias

This example confirms efficacy of an exemplary bispecific antibody agent in treating even difficult to treat tumors. Extramedullary leukemias (EM-leukemias) are currently very challenging to effectively treat. EM-leukemias include a wide variety of clinically significant phenomena that often pose therapeutic dilemmas. Myeloid sarcoma (MS) and leukemia cutis (LC) represent two EM-leukemia manifestations. The molecular mechanisms underlying EM involvement are not well defined, and the prognostic significance of EM involvement is not fully understood. Therefore, it has been difficult to define the optimal treatment of patients with EM-leukemias, such as MS or LC.

Figure 12A:
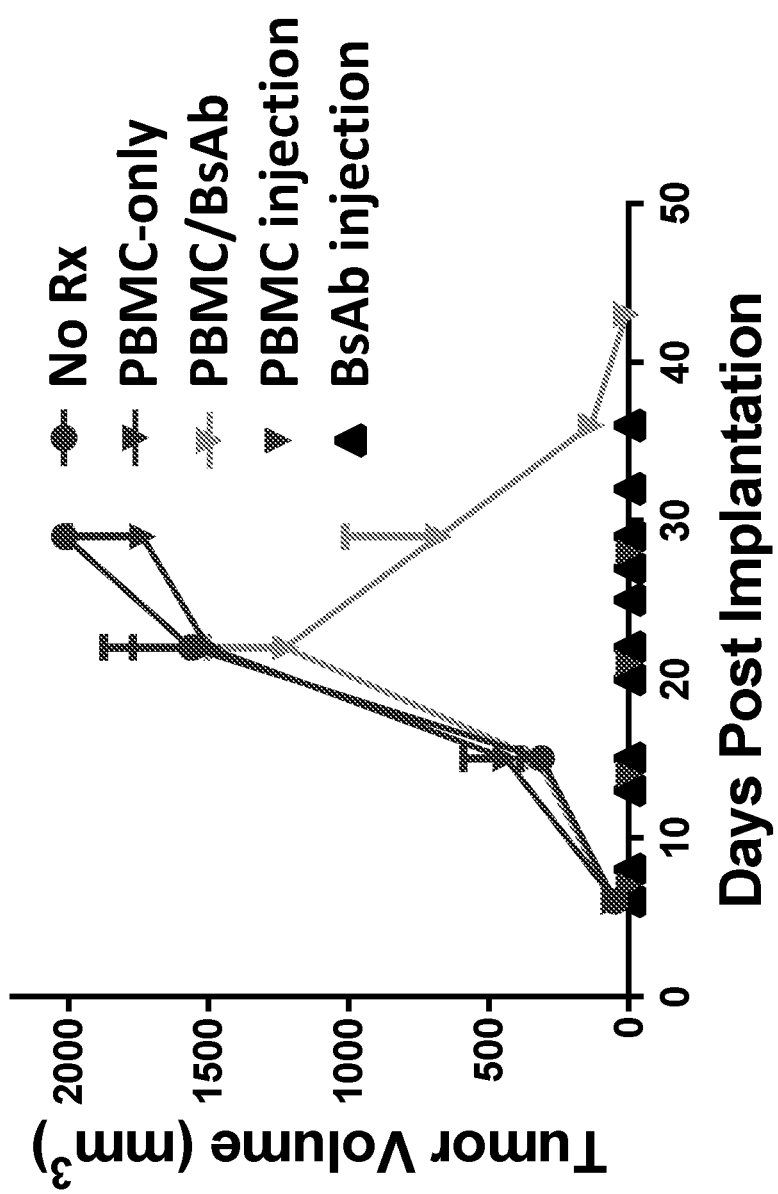
FIG. 12A, FIG. 12B, and FIG. 12C depict efficacy of an exemplary CD33-CD3 IgG-scFv (BsAb) in CD33(+) AML in lymphoma models.
Figure 12B:
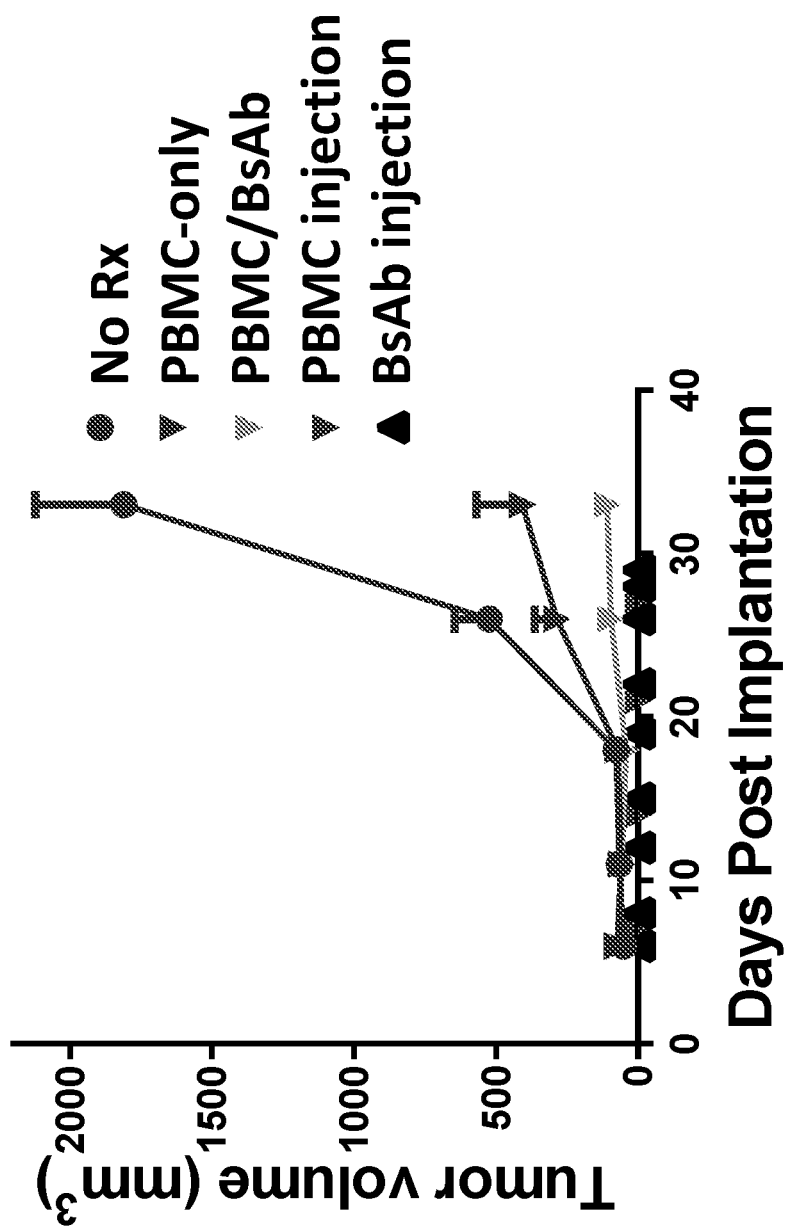
Figure 12C:
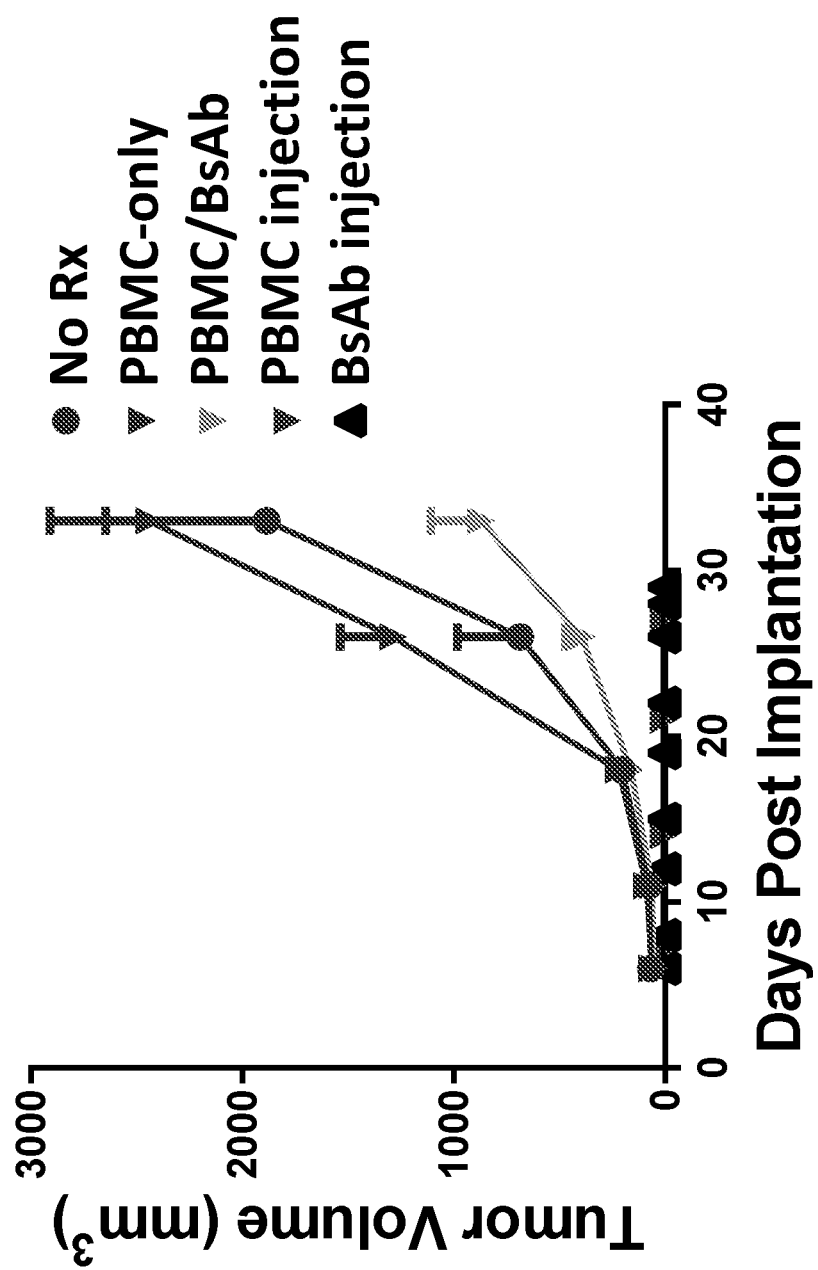

A model of EM-leukemia was generated by implanting MOLM13 cells subcutaneously. Fresh human PBMCs were injected intraperitoneally once weekly starting seven days after leukemia implantation and an exemplary bispecific antibody agent was injected one day before and one day after each T cell administration. In this model, PBMCs had to traffic from the peritoneal cavity, through the blood stream, before infiltrating the subcutaneous tumor site. In the untreated or PBMC alone control groups, tumors grew rapidly surpassing the 2000 mm$^3$ volume that required the animals to be euthanized within the first four weeks after leukemia implantation. Among the treatment groups, after the initial growth spurt, there was a rapid regression in the animals treated with both PBMCs and an exemplary bispecific antibody agent (PBMC/BsAb group) (FIG. 12A). To test the efficacy of an exemplary bispecific antibody agent against other AML xenografts, THP1 and HL60 cell lines were injected subcutaneously and after one week, treatment with PBMCs with or without the exemplary bispecific antibody agent (BsAb) was performed. Exemplary bispecific antibody agent-redirected PBMCs significantly slowed down leukemia growth while PBMCs alone had minimal or no anti-tumor effect (FIG. 12B and FIG. 12C).

Example 7—CD33 Internalization Did not Compromise CD33-BsAb Function

The present Example documents surprising internalization, efficacy, and (limited) side effect characteristics of certain CD33-BsAb provided herein.

Figure 13:
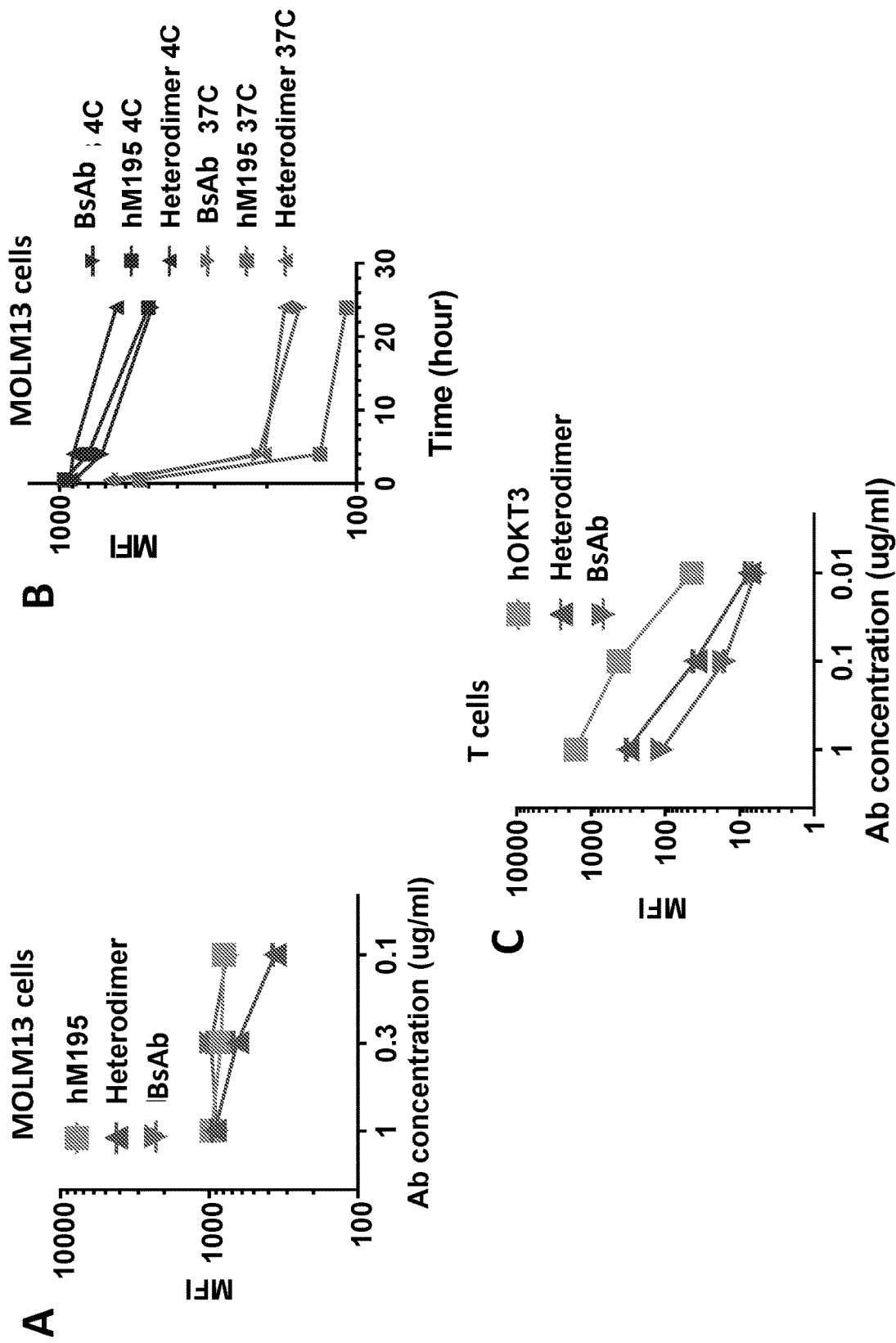
FIG. 13 depicts binding properties of an exemplary CD33-CD3 IgG-scFv (BsAb) to CD33 and CD3. (A) MOLM13 cells were reacted for 30 min at 4 C.° using decreasing doses of hM195 (anti-CD33 IgG), the heterodimeric BsAb, and an exemplary CD33-CD3 IgG-scFv. Cells were washed and immunostained with a fluorochrome-conjugated secondary antibody and mean fluorescence intensity (MFI) assayed by flow cytometry. (B) MOLM13 cells were reacted for 30 min, 4 h or 24 h at 37 C.° or 4 C.° with 1 μg/ml of hM195 (anti-CD33 IgG), the heterodimeric IgG BsAb, and exemplary CD33-CD3 IgG-scFv. Cells were washed and immunostained with a fluorochrome-conjugated secondary antibody at 4 C.°. After washing the unbound antibody, MFI was analyzed by flow cytometry. (C) Activated T cells were reacted for 30 min at 4 C.° with decreasing doses of hOKT3 (anti-CD3 IgG), the heterodimeric BsAb, and exemplary CD33-CD3 IgG-scFv. Cells were washed and immunostained with a fluorochrome-conjugated secondary antibody and MFI analyzed measured by flow cytometry.

CD33 is internalized and will compromise engagement of effector cells following antibody binding. While this phenomenon is beneficial for antibody-drug conjugates, it could render a CD33-bispecific antibody agent ineffective. Moreover, it is generally assumed that monovalency has to be maintained towards CD33 (e.g. BiTE or heterodimer) since crosslinking of CD33 could accelerate its endocytosis. Thus, the effect of valency was assessed on rate of endocytosis. MOLM13 AML cells were stained with huM195 (bivalent towards CD33), an exemplary CD33-CD3 IgG-scFv (bivalent towards CD33) or heterodimer at 37 C.° or 4 C.° (retarding internalization). At 4 C.°, whereas binding of CD33-CD3 IgG-scFv to CD33 and binding of huM195 to CD33 were comparable, heterodimer binding was almost two fold less avid to CD33 (FIG. 13, A). At 37 C.°, both huM195 and heterodimer led to internalization of CD33 within the first 4 hours after staining, although internalization was stronger with huM195 than with the heterodimer (FIG. 6B). Under the same conditions an exemplary CD33-CD3 IgG-scFv behaved identically to the heterodimer, results that were entirely unexpected. Interestingly, binding of an exemplary CD33-CD3 IgG-scFv to CD3 was 27 and 2.5 fold weaker than the binding of huOKT3 and heterodimer to CD3 (FIG. 13, C). While this lower binding of an exemplary CD33-CD3 IgG-scFv to CD3 would be expected to reduce the likelihood of cytokine release syndrome, unexpectedly, an exemplary tetravalent CD33-CD3 IgG-scFv was found to be more potent than the heterodimer in TDCC (FIG. 9). Exemplary CD33-CD3 IgG-scFv was injected one day before T cell administration in in vivo. Under these conditions internalization was expected; yet, in vivo anti-AML effect was still substantial suggesting that residual CD33 surface expression (20% for the MOLM13 cell line) was enough for anti-leukemia function of an exemplary CD33-CD3 IgG-scFv.

Example 8—CD33 was not Expressed on Cord Blood Hematopoietic Stem Cells (HSC)

Figure 14:
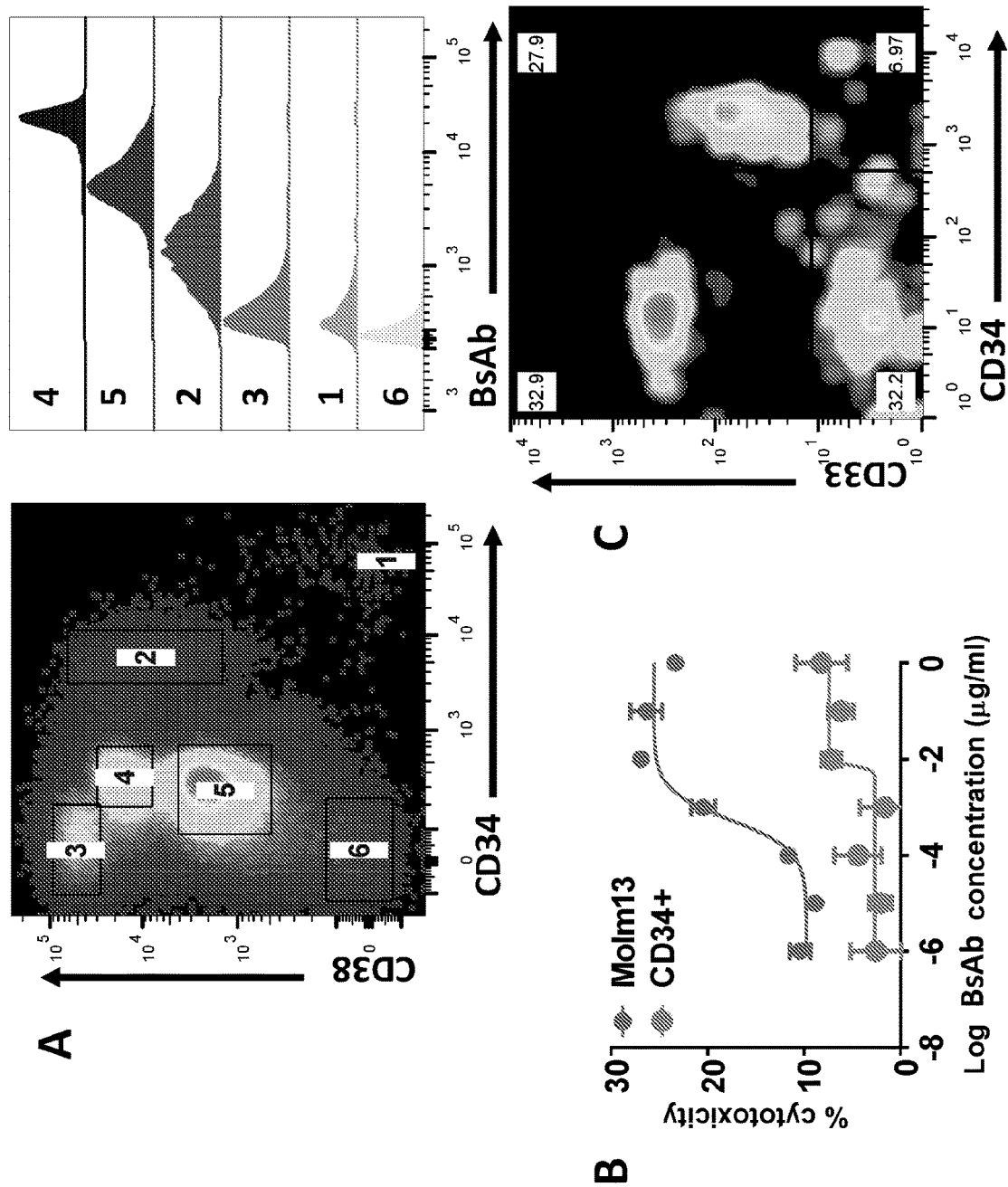
FIG. 14 depicts cross-reactivity of an exemplary CD33-CD3 IgG-scFv with CD34(+)CD38(−) hematopoietic stem cells. (A) Cord blood mononuclear cells were purified using Ficoll-Paque density gradient centrifugation and immunostained with anti-human CD3 antibody, CD19 antibody, CD38 antibody, CD34 antibody, and exemplary CD33-CD3 IgG-scFv. To exclude T cells and B cells from analysis, cells were gated on CD3(−) and CD19(−) populations. Different populations (labeled 1 to 6) of cells were assessed for their binding to exemplary CD33-CD3 IgG-scFv. (B) Hematopoietic stem and progenitor cells were isolated from cord blood mononuclear cells using Miltenyi CD34 Microbeads. (C) TDCC by ATC (E:T ratio=10) in the presence of exemplary CD33-CD3 IgG-scFv against the purified CD34+ cells and MOLM13 AML cells was tested using chromium release assay.

CD33 is considered to be a myeloid lineage specific marker and treatment with anti-CD33 antibodies may compromise long-term hematopoiesis, which could limit the therapeutic potential. (Hauswirth A W, Florian S, Printz D, et al. Eur J Clin Invest. 2007; 37(1):73-82 & Taussig D C, Pearce D J, Simpson C, et al. Blood. 2005; 106(13):4086-4092). When cord blood CD34+ cells were stained with an exemplary anti-CD33 BsAb (FIG. 14, A), almost all of the CD34(+)CD38(−) HSCs were negative, while all CD34(+)CD38(+) hematopoietic progenitor cells (HPC) were positive. Even for HPCs, the expression of CD33 was more than 20-fold lower than that on myeloid cells. CD34(+) cells isolated from cord blood were tested for sensitivity to TDCC in a standard chromium release assay. In contrast to the exemplary CD33-CD3 IgG-scFv lysed MOLM13 cells, the CD34(+) population was relatively insensitive to TDCC (FIG. 14, B). The low level killing (<5%) seen at high concentrations (1 μg/ml) of exemplary CD33-CD3 IgG-scFv could be accounted for by the residual CD34(−)CD33(+) population (CD33 expression on this population was higher than that on CD34(+)CD38(+) hematopoietic progenitor cells (FIG. 14, C).

Thus, these data confirm that an exemplary CD33-CD3 IgG-scFv of the present disclosure exhibits robust in vitro and in vivo efficacy, with unexpected characteristics and properties that may be therapeutically beneficial.

EQUIVALENTS

The articles "a" and "an" as used herein in the specification and in the claims, unless clearly indicated to the contrary, should be understood to include the plural referents. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention also includes embodiments in which more than one, or the entire group members are present in, employed in, or otherwise relevant to a given product or process. Furthermore, it is to be understood that the invention encompasses all variations, combinations, and permutations in which one or more limitations, elements, clauses, descriptive terms, etc., from one or more of the listed claims is introduced into another claim dependent on the same base claim (or, as relevant, any other claim) unless otherwise indicated or unless it would be evident to one of ordinary skill in the art that a contradiction or inconsistency would arise. Where elements are presented as lists, (e.g., in Markush group or similar format) it is to be understood that each subgroup of the elements is also disclosed, and any element(s) can be removed from the group. It should be understood that, in general, where the invention, or aspects of the invention, is/are referred to as comprising particular elements, features, etc., certain embodiments of the invention or aspects of the invention consist, or consist essentially of, such elements, features, etc. For purposes of simplicity those embodiments have not in every case been specifically set forth in so many words herein. It should also be understood that any embodiment or aspect of the invention can be explicitly excluded from the claims, regardless of whether the specific exclusion is recited in the specification. The publications, websites and other reference materials referenced herein to describe the background of the invention and to provide additional detail regarding its practice are hereby incorporated by reference.

What is claimed is:

1. A bispecific antibody agent comprising two identical immunoglobulin heavy chains and two identical fusion polypeptides, wherein each heavy chain comprises a heavy chain variable domain sequence that is SEQ ID NO:1 or 2, and wherein each fusion polypeptide comprises:
   (i) an immunoglobulin light chain comprising a light chain variable domain sequence that is SEQ ID NO:3 or 4, and
   (ii) a single chain variable fragment (scFv),
   wherein the heavy chain and the fusion polypeptide light chain bind to CD33, and wherein the fusion polypeptide scFv binds to CD3.

2. The bispecific antibody agent of claim 1, wherein:
   (i) the heavy chains each comprise a sequence identified as any one of SEQ ID NO:9, 20-22 and 24; and/or
   (ii) the fusion polypeptide light chain comprises a light chain sequence identified as SEQ ID NO:10; and/or
   (iii) the scFv is fused to the C-terminus of the immunoglobulin light chain.

3. The bispecific antibody agent of claim 1, wherein the fusion polypeptide further comprises a linker.

4. The bispecific antibody agent of claim 1, wherein:
   (i) the fusion polypeptide comprises an scFv comprising a sequence identified as any of SEQ ID NOs: 11-17 and 27; or
   (ii) the fusion polypeptides each comprise a sequence identified as SEQ ID NO: 26.

5. The bispecific antibody agent of claim 1, wherein:
   (i) the heavy chain comprising an Fc region with one or more mutations selected from K322A and D265A; or
   (ii) the heavy chains each comprise a sequence identified as SEQ ID NO: 24.

6. An isolated nucleic acid molecule encoding a bispecific antibody agent of claim 1.

7. A host cell comprising the isolated nucleic acid molecule of claim 6.

8. A method for the production of a bispecific antibody agent comprising a step of culturing the host cell according to claim 7 in a culture medium under conditions allowing the expression of the antibody or fragment thereof and separating the antibody or fragment thereof from the culture medium.

9. A composition comprising the bispecific antibody agent of claim 1.

10. A pharmaceutical composition comprising the composition of claim 9, and further comprising a pharmaceutically acceptable carrier or diluent.

11. A T cell or a population of T cells armed with the bispecific binding agent of claim 1.

12. A chimeric antigen receptor (CAR) comprising a bispecific binding agent of claim 1.

13. A CAR-T cell, a population of CAR-T cells, a CAR-NK cell, or a population of CAR-NK cells expressing a CAR of claim 12.

14. A composition comprising the population of CAR-NK cells of claim 13.

15. The bispecific antibody agent of claim 1, wherein the fusion polypeptide comprises an scFv that is a humanized OKT3 scFv.

16. The bispecific antibody agent of claim 1, wherein the heavy chain variable domain comprises a sequence of SEQ ID NO:1 or 2, and wherein each fusion polypeptide comprises:

(i) an immunoglobulin light chain comprising a light chain variable domain sequence of SEQ ID NO:3 or 4, and (ii) a single chain variable fragment (scFv) comprising a sequence of any one of SEQ ID NOs: 11-17 and 27.

17. The bispecific antibody agent of claim 1, wherein:

(i) the heavy chains each comprise a sequence identified as SEQ ID NO: 24; and (ii) the fusion polypeptides each comprise a sequence identified as SEQ ID NO: 26.

18. The isolated nucleic acid molecule of claim 6, wherein the isolated nucleic acid comprises:

(i) a sequence encoding a heavy chain identified as SEQ ID NO: 23; and/or (ii) a sequence encoding a fusion polypeptide identified as SEQ ID NO: 25.

19. A recombinant vector encoding the bispecific antibody agent of claim 1.

* * * * *